US008470971B2

(12) United States Patent
Jo et al.

(10) Patent No.: US 8,470,971 B2

(45) Date of Patent: Jun. 25, 2013

(54) CELL PERMEABLE P53 RECOMBINANT PROTEIN, POLYNUCLEOTIDE ENCODING THE SAME, AND ANTI-CANCER COMPOSITION CONTAINING THE SAME AS ACTIVE INGREDIENT

(75) Inventors: Daewoong Jo, Seoul (KR); Jung-Hee Lim, Gwangmyeong-si (KR)

(73) Assignee: Procell Therapeutics Inc., Seoul (KR)

( * ) Notice: Subject to any disclaimer, the term of this patent is extended or adjusted under 35 U.S.C. 154(b) by 194 days.

(21) Appl. No.: 13/132,202

(22) PCT Filed: Dec. 2, 2009

(86) PCT No.: PCT/KR2009/007142

§ 371 (c)(1), (2), (4) Date: Aug. 18, 2011

(87) PCT Pub. No.: WO2010/064838

PCT Pub. Date: Jun. 10, 2010

(65) Prior Publication Data

US 2012/0122796 A1 May 17, 2012

Related U.S. Application Data

(60) Provisional application No. 61/193,463, filed on Dec. 2, 2008.

(51) Int. Cl.
*C07K 7/00* (2006.01)

(52) U.S. Cl.
USPC .......................................... 530/350; 536/23.1

(58) Field of Classification Search
None
See application file for complete search history.

(56) References Cited

FOREIGN PATENT DOCUMENTS

KR 100887266 B1 2/2009

OTHER PUBLICATIONS

Chang, et al., 'Dissecting intracellular signaling pathways with membrane-permeable peptides', Science's STKE, vol. 2000(47), p. PL. 1 (Aug. 29, 2000).

Scheller, et al., 'Evidence for an amphipathicity independent cellular uptake of amphipathic cell-penetrating peptides', European Journal of Biochemistry, vol. 267, pp. 6043-6049 (2000).

Wang, et al., 'Targeting p53 by PTD-mediated transduction', Trends in Biotechnology, vol. 22(9), pp. 431-434 (Sep. 2004).

Yoshikawa, et al., 'Organelle-targeted delivery of biological macromolecules using the protein transduction domain: potential applications for peptide aptamer delivery into the nucleus', J. Mol. Biol., vol. 380, pp. 777-782 (May 29, 2008, published on web).

Bassett, et al., 'Structural and functional basis for therapeutic modulation of p53 Signaling', Clin. Cancer Res., vol. 14(20), pp. 6376-6386 (Oct. 16, 2008 published on web).

International Search Report for PCT/KR2009/007142 dated on Jul. 20, 2010.

*Primary Examiner* — Sheela J Huff

(74) *Attorney, Agent, or Firm* — Lucas & Mercanti, LLP

(57) ABSTRACT

Disclosed are a cell-permeable p53 recombinant protein in which a macromolecule transduction domain (MTD) is fused to the tumor suppressor p53, a polynucleotide encoding the same, a recombinant expression vector for producing the same, and a pharmaceutical composition of the treatment of cancer, comprising the same. Having high cell permeability, the p53 recombinant protein is effectively transduced into cells so that the tumor suppressor p53 can be translocated into cell nuclei. Within nuclei, p53 inhibits the formation of cyclin-CDK complexes to halt the cell cycle, thus suppressing excessive cell proliferation and inducing apoptosis of tumor cells. Therefore, the p53 recombinant protein can be useful as an anticancer agent in the treatment of various cancers.

30 Claims, 15 Drawing Sheets

PCR Amplification of p53 & Δp53

| Clone # | A/a # | ORF Length | Construct Structure |
|---|---|---|---|
| P1 | 416 | 1248 | HNp53 |
| P2 | 426 | 1278 | $HNM_{39}p53$ |
| P3 | 424 | 1272 | $HNM_{41}p53$ |
| P4 | 426 | 1278 | $HNp53M_{39}$ |
| P5 | 424 | 1272 | $HNp53M_{41}$ |
| P6 | 436 | 1308 | $HNM_{39}p53M_{39}$ |
| P7 | 432 | 1296 | $HNM_{41}p53M_{41}$ |

| Clone # | A/a # | ORF Length | Construct Structure |
|---|---|---|---|
| NP1 | 126 | 378 | HNΔp53 |
| NP2 | 136 | 408 | $HNM_{39}\Delta p53$ |
| NP3 | 134 | 402 | $HNM_{41}\Delta p53$ |
| NP4 | 136 | 408 | $HN\Delta p53M_{39}$ |
| NP5 | 134 | 402 | $HN\Delta p53M_{41}$ |
| ΔP1 | 121 | 363 | HΔp53 |
| ΔP2 | 131 | 393 | $HM_{39}\Delta p53$ |
| ΔP3 | 129 | 387 | $HM_{41}\Delta p53$ |
| ΔP4 | 131 | 393 | $H\Delta p53M_{39}$ |
| ΔP5 | 129 | 387 | $H\Delta p53M_{41}$ |

CELL PERMEABLE P53 RECOMBINANT PROTEIN, POLYNUCLEOTIDE ENCODING THE SAME, AND ANTI-CANCER COMPOSITION CONTAINING THE SAME AS ACTIVE INGREDIENT

CROSS-REFERENCE TO RELATED APPLICATIONS

This application is a 371 of PCT/KR2009/007142 filed Feb. 12, 2009, which claims the benefit of United States Provisional Patent Application No. 61/193,463 filed Feb. 12, 2008, the contents of each of which are incorporated herein by reference.

BACKGROUND OF THE INVENTION

1. Field of the Invention

The present invention relates to a cell-permeable p53 recombinant protein in which a macromolecule transduction domain (MTD) is fused to the tumor suppressor p53, a polynucleotide encoding the same, a recombinant expression vector for producing the same, and a pharmaceutical composition of the treatment of cancer caused by p53 deficiency or by the loss of p53 function, comprising the same.

2. Description of the Related Art

The tumor suppressor p53 is a potent transcription factor that plays a central role in large networks of proteins that integrate a variety of signal transduction pathways including cell cycle regulation, apoptosis initiation, DNA repair, senescence and other anticancer functions. In light of the finding that approximately 50% of primary tumors have mutations in the p53 gene, with the observation of mutant p53 regulators in the remainder, p53 can be seen to be responsible for the effective suppression of human tumors. In fact, the repair of p53 in p53-mutant tumor cells was found to lead to apoptosis of the cells.

In normal cells, p53 levels are kept low because p53 proteins are inactivated by association with MDM2 (Murine double minute 2) and because they are degraded rapidly on synthesis. In response to various stresses including DNA damage, the expression of the p53 protein increases and becomes activated to prevent malignant transformation by inducing cell cycle arrest and apoptosis. The cell cycle is the series of events that take place in a cell leading to its division and duplication and consists of four distinct phases: the G1 phase, the S phase for DNA replication, the G2 phase, and the M phase for cell division. The cell cycle is regulated at various checkpoints therein. p21 is activated by the transcription factor p53 and halts the cell cycle in the G1 phase. When activated by p53, p21 binds to and inactivates cyclin-CDK (cyclin-dependent kinase) complexes.

MDM2 (Murine double minute 2) is a representative p53 inhibitor that binds to the p53 transactivation domain to prevent p53 from inducing the expression of target genes. Further, acting as a ubiquitin ligase targeting p53, MDM2 induces the ubiquitination of p53 and mediates the degradation of p53 by the 26S proteasome pathway. The p53 transcription factor induced in damaged cells activates the transcription of MDM2 while MDM2 promotes the degradation of p53, which, in turn, increases the expression of MDM2. As such, there is an autoregulatory feedback loop between p53 and MDM2.

Mutant or inactivated p53 is found in most human tumor cells. p53-mediated signal transduction pathways exhibit very complicated tissue specificity. In some cell types such as fibroblasts and epithelial cells, p53 acts to induce permanent or transient cell cycle arrest in the G1 and G2 phases of the cell cycle to prevent the cells from proliferating or growing when the DNA is in a state of damage and repair. Human p53 is 393 amino acids long and has a modular structure comprised of four main functional domains. Of them, the DNA binding domain (DBD, residues 102-292) is known to play a core role in the functions of p53. Approximately 90% of the known mutations that deactivate p53 in cases of cancer occur in this domain. As for the regulation and activation of p53, it is achieved mainly by posttranslational modifications including ATM (ataxia-telangiectasia mutated)/ATR (ataxia telangiectasia and Rad3 related)-mediated phosphorylation at the Ser/Thr residues, the up-regulation of p53 transcriptional activity by histone acetylase, ubiquitination at carboxyl-terminal lysine residues, and sumoylation.

One of the most effective approaches to the molecular therapy of cancer is to rehabilitate the function of wild-type p53. For this, a lot of effort has been conventionally focused on gene delivery so that wild-type p53 will be expressed in tumor cells having mutant p53 or on the finding of small molecules that can activate p53 in tumor cells. Despite all attempts, the suggestions made thus far remain at the stage of mere possibility, with the appearance of inadequate physical and chemical properties, and thus have not yet culminated in characteristic cancer therapeutics.

To overcome the problems encountered with conventional attempts, p53 was imparted with cell permeability by fusion into a macromolecule transduction domain (MTD), which facilitates the transduction of macromolecules into cells. As a result, recombinant p53, called cell permeable-p53 (CP-p53), has been developed for anti-cancer therapeutics.

The macromolecule transduction domain (MTD) developed by the present inventors is capable of cell-to-cell delivery so that it allows the systemic transduction of macromolecules upon administration upon any route. Hence, CP-p53, when fused to the MTD, can be effectively transduced into cells, which might certainly result in the development of protein-based bio-drugs that could cure diseases caused by p53 deficiency or by the loss of p53 function. Under the conviction that the overexpression within cells or direct delivery into cells of p53 could suppress the formation and growth of a tumor, the present inventors have put a lot of effort into developing novel anticancer agents using MTD.

Synthetic compounds or natural small molecules can be transduced into cells, but macromolecules such as proteins, peptides, nucleic acids, etc. cannot due to their large sizes. It is difficult for macromolecules with a molecular weight of 500 or more to pass through a plasma membrane, that is, the lipid bilayer structures, of viable cells. To overcome this problem, macromolecule intracellular transduction technology (MITT) was developed (Korean Patent Application No. 10-2009-7017564, U.S. patent application Ser. No. 12/524,935, Canadian Patent Application No. 2,676,797, Chinese Patent Application No. 00880003468.9, Australian Patent Application No. 2008211854, Indian Patent Application No. 5079/CHENP/2009, EU Patent Application No. 08712219.8, Japanese Patent Application No. not yet assigned (priority based on USPP: 60/887,060)). MITT facilitates the transverse of therapeutic macromolecules across membranes into cells, thus making it possible to develop peptides, proteins and genes themselves as bio-drugs, which is impossible using conventional techniques. According to MITT, macromolecules are fused to hydrophobic macromolecule transduction domains and other various intracellular vehicles, expressed and purified as recombinant proteins. When administered into the body, the recombinant proteins are transduced into cells and delivered to intracellular target sites where the macromolecules functionally operate. As described, MTD allows the conveyance into cells of various molecules which are incapable of permeating into cells, such as peptides, proteins, DNA, RNA, synthetic molecules, etc.

Culminating in the present invention, intensive and thorough research into the use of p53 in the treatment of cancer, conducted by the present inventors, resulted in the finding that when imparted with cell permeability by fusion into MTD, the tumor suppressor p53 can be effectively translocated into cell nuclei in vivo as well as in vitro and that the p53 recombinant protein can be used as an anticancer agent for treating cancers caused by p53 deficiency or by the loss of p53 function.

SUMMARY OF THE INVENTION

It is therefore an object of the present invention to provide a p53 recombinant protein that can effectively permeate cells and that is useful as an anticancer agent for treating various cancers caused by p53 deficiency or by the loss of p53 function.

In accordance with an aspect thereof, the present invention provides a cell permeable p53 recombinant protein, comprising the tumor suppressor p53 fused into a macromolecule transduction domain (MTD), which allows p53 to effectively penetrate into cells.

In accordance with another aspect thereof, the present invention provides a polynucleotide encoding the cell permeable p53 recombinant protein.

In accordance with a further aspect thereof, the present invention provides an expression vector carrying the polynucleotide and a microorganism transformed with the expression vector.

In accordance with still a further aspect thereof, the present invention provides a method for producing the cell permeable p53 recombinant protein by culturing the transformed microorganism.

In accordance with still another aspect thereof, the present invention provides a pharmaceutical composition for the treatment of cancer caused by p53 deficiency or loss of p53 function, comprising the p53 recombinant protein as an active ingredient.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
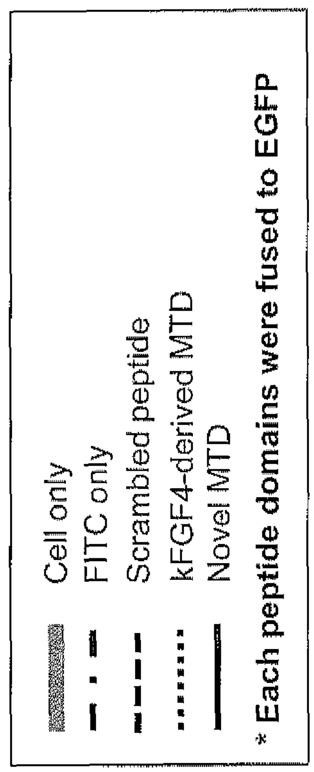
FIG. 1 is of graphs illustrating the results of quantitative flow cytometric analysis of the cell permeability of JO-39 and JO-41 MTDs of the present invention
Figure 1:
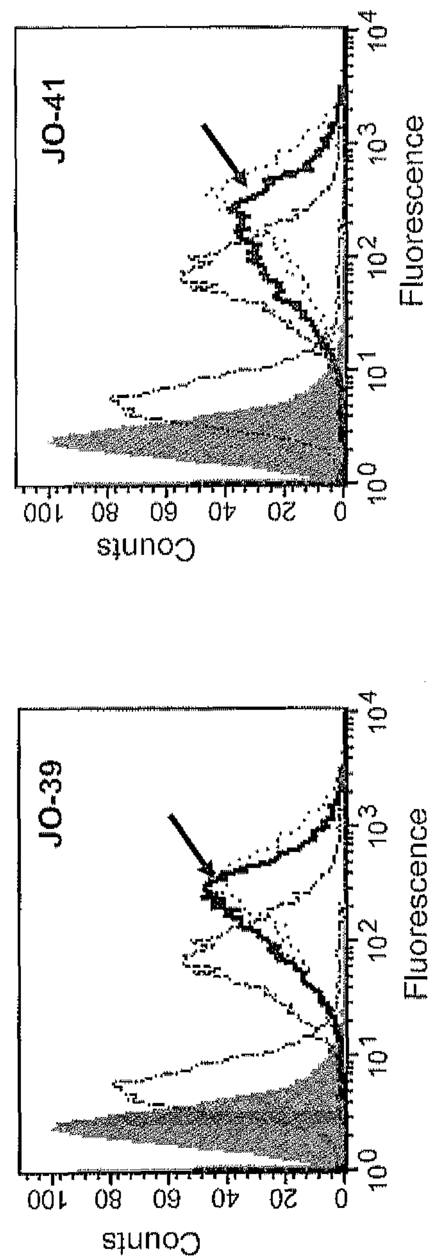

In an aspect thereof, the present invention addresses a cell permeable p53 recombinant protein (CP-p53) in which the tumor suppressor p53 is imparted with cell permeability thanks to being fused to a macromolecule transduction domain (MTD) and that is highly efficient at transporting p53 into cells, and a polynucleotide encoding the same.

In the present invention, the tumor suppressor p53 can penetrate into cells because it is fused into a macromolecule transduction domain.

To send p53 to the cell nucleus, a nuclear localization sequence (NLS) is added to full-length p53 in accordance with an embodiment, and the resulting recombinant is named NLS-p53 (Np53), which has an amino acid sequence of SEQ ID NO: 12, encoded, for example, by a polynucleotide having a nucleotide sequence of SEQ ID NO: 11.

In this context, full-length p53 is fused with JO-39 MTD ($MTD_{39}$) to afford full-length forms of recombinant proteins, named:

NLS-$MTD_{39}$-p53 ($NM_{39}$p53), having an amino acid of SEQ ID NO: 14, encoded, for example, by a polynucleotide having a nucleotide sequence of SEQ ID NO: 13;

NLS-p53-$MTD_{39}$ ($Np53M_{39}$), having an amino acid of SEQ ID NO: 16, encoded, for example, by a polynucleotide having a nucleotide sequence of SEQ ID NO: 15;

NLS-$MTD_{39}$-p53-$MTD_{39}$ ($NM_{39}p53M_{39}$), having an amino acid of SEQ ID NO: 18, encoded, for example, by a polynucleotide having a nucleotide sequence of SEQ ID NO: 17.

According to another embodiment, full-length p53 is fused with JO-41 MTD ($MTD_{41}$) to afford a recombinant protein, named:

NLS-$MTD_{41}$-p53 ($NM_{41}p53$), having an amino acid of SEQ ID NO: 20, encoded, for example, by a polynucleotide having a nucleotide sequence of SEQ ID NO: 19;

NLS-p53-$MTD_{41}$ ($Np53M_{41}$), having an amino acid of SEQ ID NO: 22, encoded, for example, by a polynucleotide having a nucleotide sequence of SEQ ID NO: 21; and NLS-$MTD_{41}$-p53-$MTD_{41}$ ($NM_{41}p53M_{41}$), having an amino acid of SEQ ID NO: 24, encoded, for example, by a polynucleotide having a nucleotide sequence of SEQ ID NO: 23.

Also, p53 may be in a truncated form (Δp53) for use in the construction of a recombinant protein and may have an amino acid sequence of SEQ ID NO: 26, encoded, for example, by a polynucleotide having a nucleotide sequence of SEQ ID NO: 25.

In this context, an NLS may be added to the truncated p53 and the resulting recombinant protein is named NLS-Δp53 (NΔp53), which has an amino acid of SEQ ID NO: 36, encoded, for example, by a polynucleotide having a nucleotide sequence of SEQ ID NO: 35.

According to a further embodiment, the truncated p53 is fused with JO-39 MTD ($MTD_{39}$) to afford truncated forms of p53 recombinant proteins, named:

$MTD_{39}$-Δp53 ($M_{39}$Δp53), having an amino acid of SEQ ID NO: 28, encoded, for example, by a polynucleotide having a nucleotide sequence of SEQ ID NO: 27;

Δp53-$MTD_{39}$ (Δp53$M_{39}$), having an amino acid of SEQ ID NO: 30, encoded, for example, by a polynucleotide having a nucleotide sequence of SEQ ID NO: 29;

NLS-$MTD_{39}$-Δp53 ($NM_{39}$Δp53), having an amino acid of SEQ ID NO: 38, encoded, for example, by a polynucleotide having a nucleotide sequence of SEQ ID NO: 37;

NLS-Δp53-$MTD_{39}$ (NΔp53$M_{39}$), having an amino acid of SEQ ID NO: 40, encoded, for example, by a polynucleotide having a nucleotide sequence of SEQ ID NO: 39.

According to still a further embodiment, the truncated p53 is fused with JO-41 MTD ($MTD_{41}$) to afford truncated forms of recombinant proteins, named:

$MTD_{41}$-Δp53 ($M_{41}$Δp53), having an amino acid of SEQ ID NO: 32, encoded, for example, by a polynucleotide having a nucleotide sequence of SEQ ID NO: 31;

Δp53-$MTD_{41}$ (Δp53$M_{41}$), having an amino acid of SEQ ID NO: 34, encoded, for example, by a polynucleotide having a nucleotide sequence of SEQ ID NO: 33;

NLS-$MTD_{41}$-Δp53 ($NM_{41}$Δp53), having an amino acid of SEQ ID NO: 42, encoded, for example, by a polynucleotide having a nucleotide sequence of SEQ ID NO: 41;

NLS-Δp53-$MTD_{41}$ (NΔp53$M_{41}$), having an amino acid of SEQ ID NO: 44, encoded, for example, by a polynucleotide having a nucleotide sequence of SEQ ID NO: 43.

For feasible isolation and purification, His-tag may be added to the p53 recombinant proteins.

In this context, full-length p53 is fused to JO-39 MTD ($MTD_{39}$) to afford full-length forms of p53 recombinant proteins, named:

His-NLS-$MTD_{39}$-p53 ($HNM_{39}p53$), having an amino acid of SEQ ID NO: 48, encoded, for example, by a polynucleotide having a nucleotide sequence of SEQ ID NO: 47;

His-NLS-p53-$MTD_{39}$ ($HNp53M_{39}$), having an amino acid of SEQ ID NO: 50, encoded, for example, by a polynucleotide having a nucleotide sequence of SEQ ID NO: 49;

His-NLS-$MTD_{39}$-p53-$MTD_{39}$ ($HNM_{39}p53M_{39}$), having an amino acid of SEQ ID NO: 52, encoded, for example, by a polynucleotide having a nucleotide sequence of SEQ ID NO: 51.

Also, full-length p53 is fused to JO-41 MTD ($MTD_{41}$) to afford full-length forms of p53 recombinant proteins, named:

His-NLS-$MTD_{41}$-p53 ($HNM_{41}p53$), having an amino acid of SEQ ID NO: 54, encoded, for example, by a polynucleotide having a nucleotide sequence of SEQ ID NO: 53;

His-NLS-p53-$MTD_{41}$ ($HNp53M_{41}$), having an amino acid of SEQ ID NO: 56, encoded, for example, by a polynucleotide having a nucleotide sequence of SEQ ID NO: 55;

His-NLS-$MTD_{41}$-p53-$MTD_{41}$ ($HNM_{41}p53M_{41}$), having an amino acid of SEQ ID NO: 58, encoded, for example, by a polynucleotide having a nucleotide sequence of SEQ ID NO: 57.

Also, truncated p53 is fused to JO-39 MTD ($MTD_{39}$) to afford truncated forms of p53 recombinant proteins, named:

His-$MTD_{39}$-Δp53 ($HM_{39}$Δp53), having an amino acid of SEQ ID NO: 64, encoded, for example, by a polynucleotide having a nucleotide sequence of SEQ ID NO: 63;

His-Δp53-$MTD_{39}$ (HΔp53$M_{39}$), having an amino acid of SEQ ID NO: 66, encoded, for example, by a polynucleotide having a nucleotide sequence of SEQ ID NO: 65;

His-NLS-$MTD_{39}$-Δp53 ($HNM_{39}$Δp53), having an amino acid of SEQ ID NO: 68, encoded, for example, by a polynucleotide having a nucleotide sequence of SEQ ID NO: 67;

His-NLS-Δp53-$MTD_{39}$ (HNΔp53$M_{39}$), having an amino acid of SEQ ID NO: 70, encoded, for example, by a polynucleotide having a nucleotide sequence of SEQ ID NO: 69.

When truncated p53 is fused to JO-41 MTD ($MTD_{41}$), the following truncated forms of p53 recombinant proteins are produced as named:

His-$MTD_{41}$-Δp53 ($HM_{41}$Δp53), having an amino acid of SEQ ID NO: 72, encoded, for example, by a polynucleotide having a nucleotide sequence of SEQ ID NO: 71;

His-Δp53-$MTD_{41}$ (HΔp53$M_{41}$), having an amino acid of SEQ ID NO: 74, encoded, for example, by a polynucleotide having a nucleotide sequence of SEQ ID NO: 73;

His-NLS-$MTD_{41}$-Δp53 ($HNM_{41}$Δp53), having an amino acid of SEQ ID NO: 76, encoded, for example, by a polynucleotide having a nucleotide sequence of SEQ ID NO: 75;

His-NLS-Δp53-$MTD_{41}$ (HNΔp53$M_{41}$), having an amino acid of SEQ ID NO: 78, encoded, for example, by a polynucleotide having a nucleotide sequence of SEQ ID NO: 77.

The present invention is featured by having MITT in which the tumor suppressor p53, a macromolecule difficult to transport into cells, is increased in cell permeability because it has been fused with a macromolecular transduction domain (hereinafter referred to as "MTD") and is delivered into cells with great efficiency. In this regard, the MTD may be fused to either or both ends of p53. The MITT using an MTD, which is a secreted protein-derived hydrophobic peptide, allows the real-time quantitative regulation of p53 in cells, so that it can mediate the delivery of p53 into cancerous tissue and distribute p53 to cancer cells.

This effect recovers the activity of the p53 suppressed in cancer cells, providing an environment that induces cancer cells to undergo cell cycle arrest and apoptosis.

In the present invention, a peptide domain is used as an MTD fusible to the tumor suppressor p53 to develop a cell permeable p53 recombinant protein.

As used herein the term "cell permeable p53 recombinant protein" refers to a complex in which a macromolecule transduction domain is covalently bonded to the tumor suppressor p53 by genetic fusion or chemical linkage. Herein, the term "genetic fusion" means a linear covalent linkage established by the genetic expression of a DNA sequence coding for the recombinant protein of interest.

p53, which suppresses unnecessary cell proliferation in the body by inhibiting the cell cycle of cancer cells, has the nucleotide sequence of SEQ ID NO: 1 and the amino acid sequence of SEQ ID NO: 2. Functionally, it is a tumor suppressor that halts the cell cycle at the G1 phase. The tumor suppressor p53 consists of 393 amino acid residues as can be seen by the amino acid sequence of SEQ ID NO: 2.

The truncated p53 (Δp53) has a nucleotide sequence of SEQ ID NO: 3 and an amino acid sequence of SEQ ID NO: 4, and consists of 101 amino acid residues as can be seen by SEQ ID NO: 4, also acting as a tumor suppressor useful in the present invention.

As for the macromolecule transduction domain fusible to the tumor suppressor p53, it may be a cell-permeable polypeptide which has the nucleotide sequence of SEQ ID NO: 5 and the amino acid sequence of SEQ ID NO: 6.

In another embodiment, the macromolecule transduction domain which can be fused to the tumor suppressor p53 may be a cell-permeable polypeptide which has the nucleotide sequence of SEQ ID NO: 7 and the amino acid sequence of SEQ ID NO: 8.

The macromolecule transduction domain having the amino acid sequence of SEQ ID NO: 6 or SEQ ID NO: 8 is a cell-permeable polypeptide which mediates the transport of biologically active molecules such as polypeptides, protein domain, or full length protein, etc., into the cytoplasm through the cell membrane. The macromolecule transduction domain has a signal peptide which consists of an N-terminal region, a hydrophobic region for targeting the cell membrane, and a C-terminal, secreted protein cleavage site, forming a helix. Such macromolecule transduction molecules are capable of traversing across the cell membrane without damaging cells, thus transporting target proteins into cells.

The macromolecule transduction domains, having amino acid sequences respectively represented by SEQ ID NOS: 6 and 8, which can be fused to the tumor suppressors p53 and Δp53, are summarized in Table 1, below.

9, may be used as an NLS fusible to p53, but the present invention is not limited thereto. Other NLSs known in the art may be employed.

In accordance with an embodiment of the present invention, the MTD fusible to the tumor suppressor p53 may be JO-39 MTD (hereinafter referred to as "$MTD_{39}$"), derived from an amyloid beta A4 protein precursor (ABPP), having the amino acid sequence of SEQ ID NO: 6, or JO-41 MTD (hereinafter referred to as "$MTD_{41}$"), a secreted protein derived from *Streptomyces coelicolor*, having the amino acid sequence of SEQ ID NO: 8.

In a preferred embodiment of the present invention, the cell-permeable p53 recombinant protein comprises full-length p53 and one or two copies of JO-39 MTD or JO-41 MTD, with fusion being carried out therebetween.

As used herein, the term "full-length p53" refers to an intact p53 protein having the entire amino acid sequence of SEQ ID NO: 2, which has had no deletions, additions, insertions or substitutions occurring at any of the amino acid residues thereof. However, a p53 derivative with various modifications caused by the deletion, addition, insertion or substitution of at least one amino acid residue of the amino acid sequence thereof may be also used in the present invention so long as it retains the anticancer activity of p53.

Figure 4:
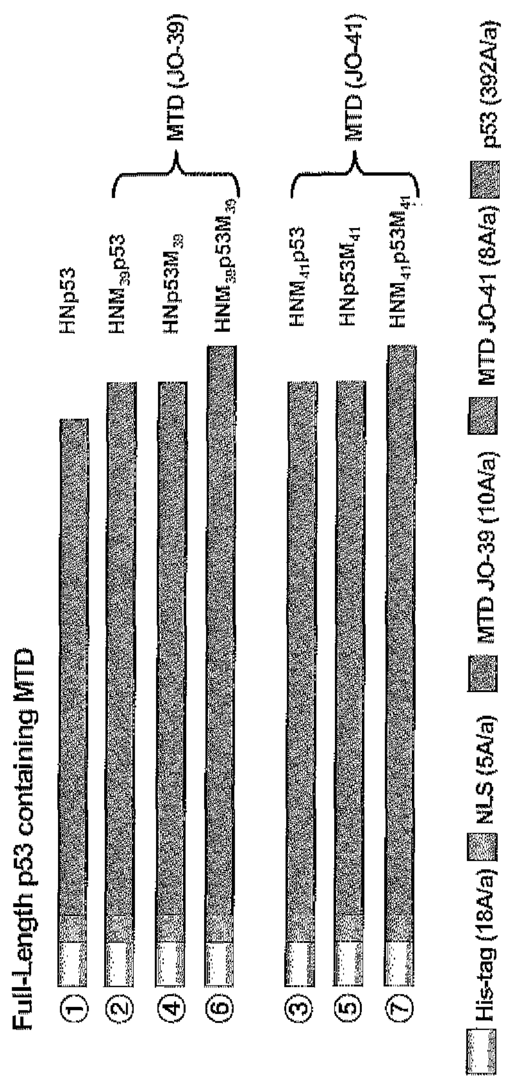
FIG. 4 is a schematic diagram illustrating the structures of the p53 recombinant proteins in which JO-39 MTD or JO-41 MTD is fused to full-length p53 in accordance with the present invention.

With reference to FIG. 4, the p53 recombinant protein useful in the present invention may be in the form of:

1) His-NLS-$MTD_{39}$-p53 ($HNM_{39}p53$) in which a set of His-NLS and JO-39 MTD is fused to the N-terminus of full-length p53;

2) His-NLS-p53-$MTD_{39}$ ($HNp53M_{39}$) in which His-NLS and JO-39 MTD are fused to the N- and C-terminus of full-length p53, respectively;

3) His-NLS-$MTD_{39}$-p53-$MTD_{39}$ ($HNM_{39}p53M_{39}$) in which His-NLS-JO-39 MTD and JO-39 MTD are fused to the N- and C-terminus of full-length p53;

4) His-NLS-$MTD_{41}$-p53 ($HNM_{41}p53$) in which a set of His-NLS and JO-41 MTD is fused to the N-terminus of full-length p53;

5) His-NLS-p53-$MTD_{41}$ ($HNp53M_{41}$) in which His-NLS and JO-41 MTD are fused to the N- and C-terminus of full-length p53, respectively;

6) His-NLS-$MTD_{41}$-p53-$MTD_{41}$ ($HNM_{41}p53M_{41}$) in which His-NLS-JO41 MTD and JO-41 MTD are fused to the N- and C-terminus of full-length p53.

Alternatively, the p53 recombination protein of the present invention may be in the same form of 1) to 6) recombinant proteins minus the His-Tag.

TABLE 1

| ID | Origin | Sequence | Length | Induction | Purification | Cell Permeability |
|---|---|---|---|---|---|---|
| JO-39 | *StrePtomyces coelicolor* | PLVLAIAAVL | 10 | ++++ | ++++ | 0.5 |
| JO-41 | *StrePtomyces coelicolor* | AAALLAVA | 8 | ++++ | ++++ | 0.4 |

The cell permeable p53 recombinant protein of the present invention has a structure in which one of the two MTDs is fused to either or both terminal ends of the tumor suppressor p53, with the optional recruitment of an SV40 large T antigen-derived nuclear localization sequence (NLS), together with a histidine-tag (His-Tag) affinity domain for feasible purification, to one end of the fusion construct.

The polypeptide having an amino acid sequence of SEQ ID NO: 10, encoded by the nucleotide sequence of SEQ ID NO:

In another preferred embodiment of the present invention, the cell-permeable p53 recombinant protein comprises truncated p53, and JO-39 MTD or JO-41 MTD, with fusion made therebetween.

As used herein, the term "truncated p53" refers to a p53 derivative having the amino acid sequence of SEQ ID NO: 4, composed of 101 amino acid residues, with the retention of the anticancer activity of p53 therein. In addition to Δp53, its derivatives made by making various modifications by means of deletion, addition, insertion or substitution of at least one amino acid residue of the amino acid sequence thereof may be also used in the present invention so long as they retain the anticancer activity of Δp53.

Figure 5:
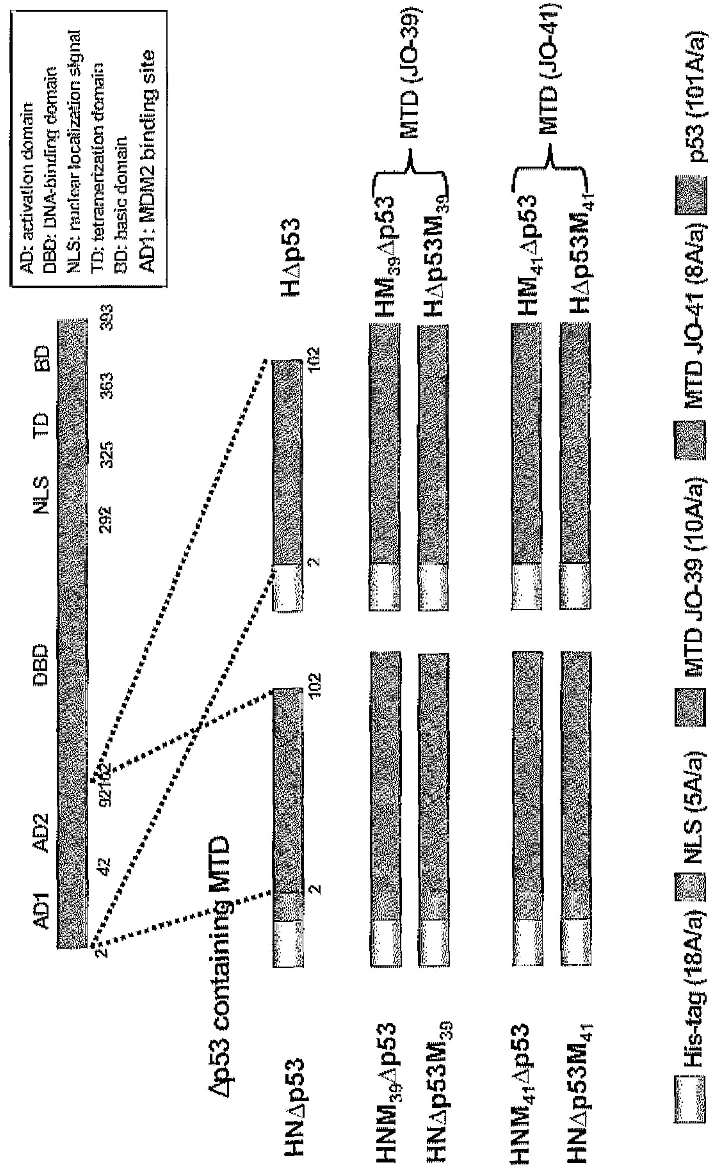
FIG. 5 is a schematic diagram illustrating the structures of the p53 recombinant proteins in which JO-39 MTD or JO-41 MTD has been fused to truncated p53 in accordance with the present invention.

With reference to FIG. 5, the p53 recombinant protein useful in the present invention may be in the form of:

7) His-NLS-$MTD_{39}$-Δp53 ($HNM_{39}$Δp53) in which a set of His-NLS and JO-39 MTD is fused to the N-terminus of truncated p53;

8) His-NLS-Δp53-$MTD_{39}$ (HNΔp53$M_{39}$) in which His-NLS and JO-39 MTD are fused to the N- and C-terminus of truncated p53, respectively;

9) His-NLS-$MTD_{41}$-Δp53 ($HNM_{41}$Δp53) in which a set of His-NLS and JO-41 MTD is fused to the N-terminus of truncated p53;

10) His-NLS-Δp53-$MTD_{41}$ (HNΔp53$M_{41}$) in which His-NLS and JO-41 MTD are fused to the N- and C-terminus of truncated p53, respectively;

11) His-$MTD_{39}$-Δp53 ($HM_{39}$Δp53) in which His-Tag and JO-39 MTD are fused to the N-terminus of truncated p53, respectively;

12) His-Δp53-$MTD_{39}$ (HΔp53$M_{39}$) in which His-Tag and JO-39 MTD are fused to the N- and C-terminus of truncated p53, respectively;

13) His-$MTD_{41}$-Δp53 ($HM_{41}$Δp53) in which a set of His-Tag and JO-41 MTD is fused to the N-terminus of truncated p53;

14) His-Δp53-$MTD_{41}$ (HΔp53$M_{41}$) in which His-Tag and JO-41 MTD are fused to the N- and C-terminus of truncated p53, respectively.

Alternatively, the p53 recombination protein of the present invention may be in the same form of 7) to 14) recombinant proteins minus the His-Tag.

For use as a control in the present invention, a p53 recombinant protein, named His-NLS-p53 (HNp53), in which the His-Tag and NLS, but not MTD, are fused to p53, is constructed. The control protein has the amino acid sequence of SEQ ID NO: 46, encoded by the polynucleotide having the nucleotide sequence of SEQ ID NO: 45.

Another control used in the present invention is the Δp53 recombinant protein His-Δp53 (HΔp53) in which His-Tag only, but not MTD, are fused to Δp53. This control protein has an amino acid sequence of SEQ ID NO: 60, encoded by a polynucleotide having a nucleotide sequence of SEQ ID NO: 59.

Another control used in the present invention is the Δp53 recombinant protein His-NLS-Δp53 (HNΔp53) in which His-Tag and NLS, but not MTD, are fused to Δp53. This control protein has an amino acid sequence of SEQ ID NO: 62, encoded by a polynucleotide having a nucleotide sequence of SEQ ID NO: 61.

Further, the present invention provides a recombinant expression vector carrying a polynucleotide encoding the cell permeable p53 recombinant protein, and a microorganism transformed with the recombinant expression vector.

The term “recombinant expression vector,” as used herein, refers to a genetic construct in which a gene of interest is operably linked to regulatory elements necessary for the expression of the gene and that permits the expression of the gene within a suitable host cell.

The term “operably linked,” as used herein, means a functional linkage between a regulatory sequence and a nucleic acid sequence of interest whereby the gene of interest can be expressed without functional problems. For example, when operably linked to a nucleic acid sequence coding for a protein or RNA, a promoter can have an influence on the expression of the gene. The functional linkage in a recombinant expression vector can be achieved using typical genetic engineering techniques. For site-specific DNA cleavage and ligation, enzymes known in the art may be employed.

Examples of the expression vector useful in the present invention include, but are not limited to, plasmid vectors, cosmid vectors, bacteriophage vectors, and viral vectors, but are not limited thereto. A suitable expression vector may be constructed in such a way to comprise a signal sequence for membrane targeting or secretion or a leader sequence as well as regulatory sequences such as a promoter, an operator, an initiation codon, a termination codon, a polyadenylation signal, an enhancer, etc., depending on the purpose. In an expression vector, a promoter may be constitutive or inducible. In addition, an expression vector may comprise a selection marker for selecting host cells transformed with the expression vector, and a replicable vector comprises a replication origin.

As such, the recombinant expression vector of the present invention may be, for example, pET28a(+)-$HM_{39}$p53. The recombinant expression vector pET28a(+)-$HM_{39}$p53 is constructed by inserting into the NdeI restriction site of the multi cloning site of pET-28a(+) (Novagen, Germany) a gene coding for $HM_{39}$p53, which is composed of JO-39 MTD fused to the N-terminus of full-length p53.

In one embodiment of the present invention, the gene is cloned into pET-28a(+) (Novagen, USA), which contains His-Tag such that six tandem histidines are tagged to the cell permeable p53 recombinant protein for the purpose of feasible purification.

Thus, the resulting cell permeable p53 recombinant protein from the recombinant expression vector comprises full-length p53 flanked at either or both sides by JO-39 MTD or JO-41 MTD, with the fusion of His-Tag and NLS to the N-terminus of the construct.

In accordance with another aspect thereof, the present invention addresses a microorganism transformed with the recombinant expression vector. The microorganism may be preferably *E. coli*. When transformed with the recombinant expression vector pET28a(+)-$HM_{39}$p53 carrying a polynucleotide which codes for the recombinant protein $HM_{39}$p53 composed of full-length p53 fused with JO-39 MTD at the N-terminus thereof, *E. coli* can overexpress the cell-permeable p53 recombinant protein. So long as it is known in the art to introduce nucleic acid into host cells, any transformation technique may be employed in the present invention. Examples of useful transformation techniques include microprojectile bombardment, electroporation, $CaHPO_4$ precipitation, $CaCl_2$ precipitation, PEG-mediated fusion, microinjection and a liposome-mediated method, but are not limited thereto.

In a preferred embodiment of the present invention, $HNM_{39}$Δp53 in which NLS and JO-39 MTD are fused to the N-terminus of the truncated p53, and $HM_{39}$Δp53 in which JO-39 MTD is fused to the N-terminus of the truncated p53 were individually transformed into *E. coli* DH5α to produce transformed microorganisms which were then deposited with the Biological Resource Center of the Korea Research Institute of Bioscience and Biotechnology on Nov. 17, 2009, under accession Nos. KCTC 11596BP and KCTC 11595BP, respectively.

In accordance with another aspect thereof, the present invention addresses a method for producing the cell-permeable Δp53 recombinant protein, comprising culturing the transformed microorganism.

In the method, the transformed microorganism is cultured in a suitable medium under conditions such that the polynucleotide encoding the cell-permeable p53 recombinant protein is expressed from the recombinant expression vector introduced into the microorganism. Achieving the expression of a recombinant protein by culturing the transformed microorganism is well known in the art. For example, transformed bacteria is seed cultured in a medium suitable for growth thereof and then inoculated into a culture medium before incubation under conditions suitable for inducing the expression of the target protein, such as in the presence of IPTG (isopropyl-β-D-thiogalactoside). Upon the completion of induction, a substantially pure recombinant protein can be recovered from the culture. The term "substantially pure," as used in the context of a recombinant protein, means that the recombinant protein of the present invention does not substantially contain other proteins originating from within the host cell.

The recovery of the recombinant protein expressed by transformants may be carried out using an isolation and purification method known in the art. Typically, a cell lysate is centrifuged to remove cell debris and culture impurities, followed by precipitation, e.g., salting-out (ammonium sulfate precipitation and sodium phosphate precipitation), solvent sedimentation (protein fraction sedimentation in acetone, ethanol, etc.). Alternatively, dialysis, electrophoresis, and various column chromatography methods may be employed. As for chromatographic purification, ion exchange chromatography, gel-permeation chromatography, HPLC, reverse-phase HPLC, affinity column chromatography, and ultrafiltration may be used alone or in combination (Maniatis et al., *Molecular Cloning*: A Laboratory Manual, Cold Spring Harbor Laboratory, Cold Spring Harbor, N.Y., 1982; Sambrook et al., *Molecular Cloning*: A Laboratory Manual, 2d Ed., Cold Spring Harbor Laboratory Press, 1989; Deutscher, M., *Guide to Protein Purification Methods Enzymology* vol. 182. Academic Press. Inc., San Diego, Calif., 1990).

When expressed from the transformed microorganism, recombinant proteins may be present in the soluble fraction or the insoluble fraction depending on protein properties. In the case of their being present in the soluble fraction, the proteins can be isolated and purified using the above-mentioned methods without significant difficulties. On the other hand, when the expressed protein is in the insoluble fraction, e.g., an inclusion body, for example, the proteins may be dissolved with a denaturation agent such as urea, surfactant, etc., centrifuged and then subjected to dialysis, electrophoresis or column chromatography purification. Because treatment with the denaturation agent causes the protein to lose its activity, the purification of the protein requires desalting and refolding processes. These desalting and refolding processes are typically carried out by performing dialysis against or dilution in a denaturation agent-free solution or by centrifugation against a filter. Also when a solution used for the purification of proteins from the soluble fraction has high salinity, these desalting and refolding processes may be performed.

In one embodiment of the present invention, the cell permeable p53 recombinant protein of the present invention was found to take the form of an inclusion body, and was purified from the insoluble fraction. In this regard, the insoluble fraction was added to a buffer containing a non-ionic surfactant such as Triton X-100, ultrasonicated and centrifuged to give a pellet. This pellet was dissolved in a urea solution, followed by centrifugation. The recombinant protein of the present invention which was dissolved by urea in as large an amount in the supernatant as was possible was purified with the aid of a histidine-tag purification kit, desalted by dialysis against a membrane, and subjected to a refolding process.

In accordance with another aspect thereof, the present invention addresses a pharmaceutical composition for the treatment of cancers caused by p53 deficiency or by the loss of p53 function, comprising the cell-permeable p53 recombinant protein as an active ingredient.

When applied to cells which are deficient in the tumor suppressing p53 or have a p53 that has lost its function, the cell-permeable p53 recombinant protein of the present invention allows the translocation of p53 into the cell nucleus so that the complex formation of cyclin with cyclin-dependent kinase can be inhibited, thereby halting the cell cycle of the cancer cells and suppressing unnecessary cell proliferation in the body. Therefore, the cell-permeable p53 recombinant protein of the present invention induces the apoptosis of cancer cells by cell cycle arrest and reactivation of signal transduction pathways involved in apoptosis, and thus can be useful as an anticancer agent in the prophylaxis and/or treatment of various cancers.

The pharmaceutical composition comprising the recombinant protein according to the present invention may further comprise a pharmaceutically acceptable vehicle suitable, for example, for oral or parenteral administration. Vehicles for use in oral administration include lactose, starch, cellulose derivatives, magnesium stearate, stearic acid and the like. Preparations intended for oral administration may be formulated in the form of enteric-coated tablets, buccal tablets, troches, capsules, elixirs, suspensions, syrups or wafers by mixing with the vehicles. Further, the vehicles for parenteral administration may include water, suitable oil, saline, aqueous glucose, glycol and the like, and may further include stabilizers and preservatives. The stabilizers suitable for the present invention may include antioxidants such as sodium bisulfite, sodium sulfite and ascorbic acid. Suitable preservatives may include benzalconium chloride, methyl-paraben, propyl-paraben and chlorobutanol. For other pharmaceutically acceptable vehicles, reference may be made to the following book (*Remington's Pharmaceutical Sciences,* $19^{th}$ ed., Mack Publishing Company, Easton, Pa., 1995).

The pharmaceutical composition of the present invention may be formulated into various parenteral or oral administration forms. Representative examples of the parenteral formulation include those designed for administration by injection, and preferable are isotonic solutions or suspensions. These injection formulations may be formulated by conventional methods using suitable dispersants, wetting agents and suspending agents. For example, active ingredients may be dissolved in a saline or buffer solution to give an injection preparation. For oral administration, for example, tablets, capsules and the like are used. These formulations may include suitable excipients such as diluents (e.g., lactose, dextrose, sucrose, mannitol, sorbitol cellulose and/or glycin) and lubricants (e.g., colloidal silica, talc, stearic acid, magnesium stearate, calcium stearate, and/or polyethylene glycol) in addition to active ingredients. The tablets may include binders, such as magnesium aluminum silicate, starch paste, gelatin, tragacanth, methyl cellulose, sodium carboxymethylcellulose, and/or polyvinylpyrrolidone (PVP), and optionally disintegrants, such as starch, agar, or alginic acid or sodium alginate, absorbents, colorants, flavoring agents and/or sweeteners. The formulations can be prepared by mixing, granulating or coating according to conventional methods well-known in the art.

If necessary, the pharmaceutical compositions of the present invention may further include pharmaceutical additives, such as preservatives, water dispersants, emulsifiers, salts for regulating osmosis, and/or buffering agents, and can be formulated according to conventional methods known in the art.

In addition, the pharmaceutical composition of the present invention can be administered via oral routes or parenteral routes such as intravenously, subcutaneously, intranasally or intraperitoneally. The oral administration may include sublingual application. The parenteral administration may include injection, such as subcutaneous injection, intramuscular injection, intravenous injection and introtumoral injection, and drip infusion.

The total effective amount of the recombinant protein of the present invention can be administered to patients in a single dose or can be administered by a fractionated treatment protocol, in which multiple doses are administered over a more prolonged period of time. Although the amount of the active ingredient in the pharmaceutical composition of the present invention may vary depending on the severity of a disease, the recombinant protein may be generally administered several times a day at a single effective dose of 5 to 20 mg for adults. However, a suitable dose of the recombinant protein in the pharmaceutical composition of the present invention may depend on many factors, such as age, body weight, health condition, sex, disease severity, diet and excretion rate of patients, as well as the route of administration and the number of treatments to be administered. In view of the above factors, any person skilled in the art may determine the effective dose of the recombinant protein as an anti-cancer agent. No special limitations are imposed on the formulation, administration route and/or administration mode of the pharmaceutical composition of the present invention, insofar as the composition exhibits the effects of the present invention.

A better understanding of the present invention may be obtained through the following examples which are set forth to illustrate, but are not to be construed as limiting the present invention.

Example 1

Cell Permeability of Selected MTD

<1-1> Flow Cytometry

JO-39 MTD ($MTD_{39}$) and JO-41 MTD ($MTD_{41}$), constructed for use as MTD in the present invention, were assayed for cell permeability. In this regard, according to the method described in reports (Yang Y. et al., *FEBS Lett.* 532 (1-2): 36-44, 2002; Motejadded H, et al., *Biotechnol Lett.* 31(4): 543-9, 2009), each MTD was fused to EGFP (enhanced green fluorescent protein) and monitored for intracellular transduction using FACS (fluorescence-activated cell sorting).

For this, the recombinant proteins EGFP-$MTD_{39}$ and EGFP-$MTD_{41}$, purified in soluble forms, were fluorescence labeled with FITC (fluorescein-5-isothiocyanate, Molecular Probe). To 2~20 mg of the recombinant protein was added 1 μL of 333 mg/mL FITC, followed by incubation at room temperature for 2 hours in the absence of light on a shaker. The resulting fluorescence-labeled recombinant proteins EGFP-$MTD_{39}$ and EGFP-$MTD_{41}$ were dialyzed at 4° C. for one day against DMEM to remove unbound FITC. Each of the recombinant proteins thus recovered was found to have a concentration of approximately 1 μg/μL as analyzed by the Bradford method protein assay.

The mouse leukemic monocyte macrophage cell line RAW 264.7 (the Korean Cell Line Bank, Seoul, Korea) was inoculated into DMEM (WelGENE) containing 10% fetal bovine serum (FBS) and 1% penicillin/streptomycin (WelGENE) at a concentration of 500 mg/mL and cultured at 37° C. in a moist, 5% $CO_2$ atmosphere.

Afterwards, the RAW 264.7 cells were treated with 10 μM of each of the FITC-conjugated EGFP-$MTD_{39}$ and EGFP-$MTD_{41}$ recombinant proteins and incubated at 37° C. for 1 hour. Subsequently, to remove free FITC exposed on the cell membrane of the recombinant protein-treated RAW 264.7, the cells were treated with trypsin/EDTA (T/E, Invitrogen) and washed three times with cold PBS (phosphate buffered saline). The cells were analyzed using a FACScan flow cytometer (Becton Dickinson, Calif.) using CellQuest Pro cytometric analysis software. For each sample, the cells were used at a concentration of $1\times10^4$ cells/μL. Two or more independent assays were performed. The cell permeability of the recombinant proteins EGFP-$MTD_{39}$ and EGFP-$MTD_{41}$ of the present invention was determined by comparison with a negative control (scrambled MTD), a positive control (kFGF4-derived MTD), a group treated with FITC alone, and a non-protein-treated group.

As can be seen in FIG. 1, the recombinant proteins fused with JO-39 MTD or JO-41 MTD in accordance with the present invention had higher permeability into cytoplasmic membranes, compared to the controls. In FIG. 1, cells alone are represented by gray filled curve, FITC alone by black dotted line-1 (_ . _ . _), the negative control (scrambled MTD) lacking cell permeability by dotted line-2 (_ _ _ _), the positive control (kFGF4-derived MTD) with cell permeability by dotted line-3 (. . . . . . . . . . .) and JO-39 MTD and JO-41 MTD by solid line (__________)

<1-2> Confocal Laser Scanning Microphotography I

The intracellular localization sites of JO-39 MTD and JO-41 MTD, identified to be permeable into cells as shown in Example 1-1, were visualized. The mouse fibroblast cell line NIH3T3 (the Korean Cell Line Bank, Seoul, Korea) was treated with 10 μM of FITC-conjugated EGFP-$MTD_{39}$ or EGFP-$MTD_{41}$ and incubated at 37° C. for 1 hour before observation by confocal laser scanning microscopy. The NIH3T3 cells were maintained for 24 hours in DMEM containing 10% FBS and 500 mg/mL of 5% penicillin/streptomycin on 8-well chamber slides (LabTek, Nalgen Nunc). The cells were washed three times with PBS and incubated with serum-free DMEM, serum-free DMEM containing FITC, or serum-free DMEM containing 10 μM of the FITC-labeled recombinant protein at 37° C. for 1 hour in a 5% $CO_2$ atmosphere. Then, the cells were fixed at room temperature for 20 min with 4% paraformaldehyde.

To discriminate intracellular localization sites of MTD, that is, to examine nuclear translocation and cell permeability, nuclei of the fixed cells were counterstained with the nuclear fluorescent stain solution PI (propidium iodide, Sigma-Aldrich). After counterstaining for 5 min with 1 μg/mL PI, the cells were washed three times with PBS. In order to preserve the FITC fluorescence of the recombinant protein, the glass slide was fixed in 10 μL of a polyvinyl alcohol mounting medium containing DABCO (Fluca) for 15 min before conducting observation. The intracellular distribution of the fluorescence was visualized with a confocal laser scanning microscope equipped with a normaski filter. Cell morphology, FITC fluorescence and PI fluorescence were observed. FITC was excited at 488 nm and detected by means of a bandpass filter at 530 nm.

Figure 2:
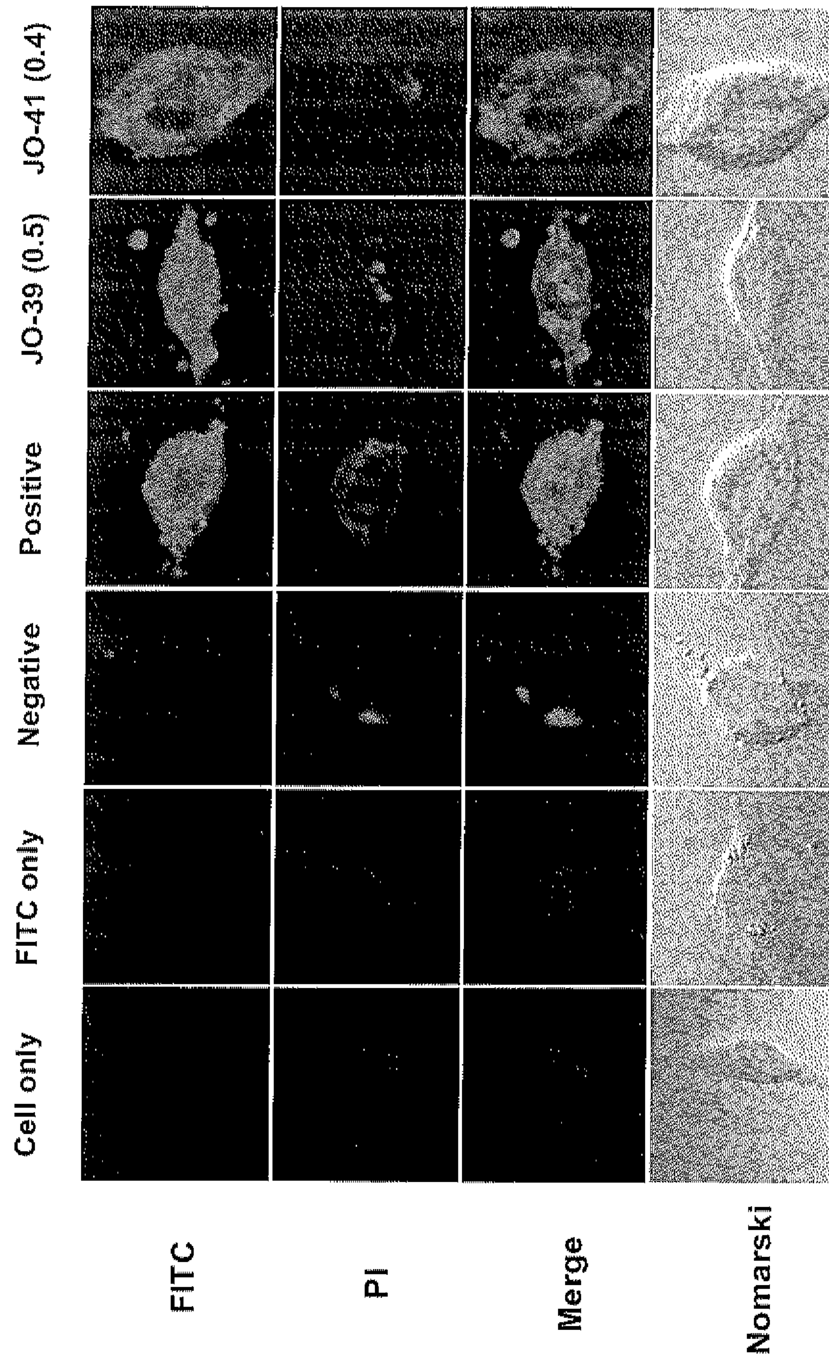
FIG. 2 is of confocal laser scanning microscopy photographs visualizing the cell permeability of JO-39 and JO-41 MTDs in NIH3T3 cells.

As shown in FIG. 2, it was observed that the cell permeable proteins with the macromolecule transduction domain JO-39 MTD or JO-41 MTD were clearly localized in the cell nucleus, as compared with the cell only, FITC only, and the negative control (scrambled MTD) and the positive control (kFGF4-derived MTD). The nuclear localization of the JO-39

MTD and JO-41 MTD recombinant proteins was consistent with the relative cell permeability determined by the above flow cytometry.

Example 2

Tissue Permeability of Selected MTD

<2-1> Confocal Laser Scanning Microscopy

To examine whether JO-39 MTD and JO-41 MTD, identified to be permeable to cells in Example 1, could be permeable to tissues, the following experiment was conducted.

First, the FITC-conjugated EGFP-$MTD_{39}$, or EGFP-$MTD_{41}$ recombinant protein was intraperitoneally injected at a dose of 300 μg into 7-week-old nude mice (Balb/c nu/nu mice, Central Lab. Animal Inc. Seoul) while two controls (negative (scrambled MTD), and positive (kFGF5-derived MTD)) were separately used. After 1.5 hours, the mice of each group were sacrificed and various organs including the liver, the kidney, the spleen, the lung, and the brain were excised from the mice. The tissues were embedded in OCT, frozen, and sliced to a thickness of 14 μm with a microtome. The slices were observed under a confocal laser scanning microscope. In this regard, to preserve the FITC fluorescence of the recombinant protein, the glass slide was fixed in 10 μL of a polyvinyl alcohol mounting medium containing DABCO (Fluca) for 15 min before making observations.

Figure 3:
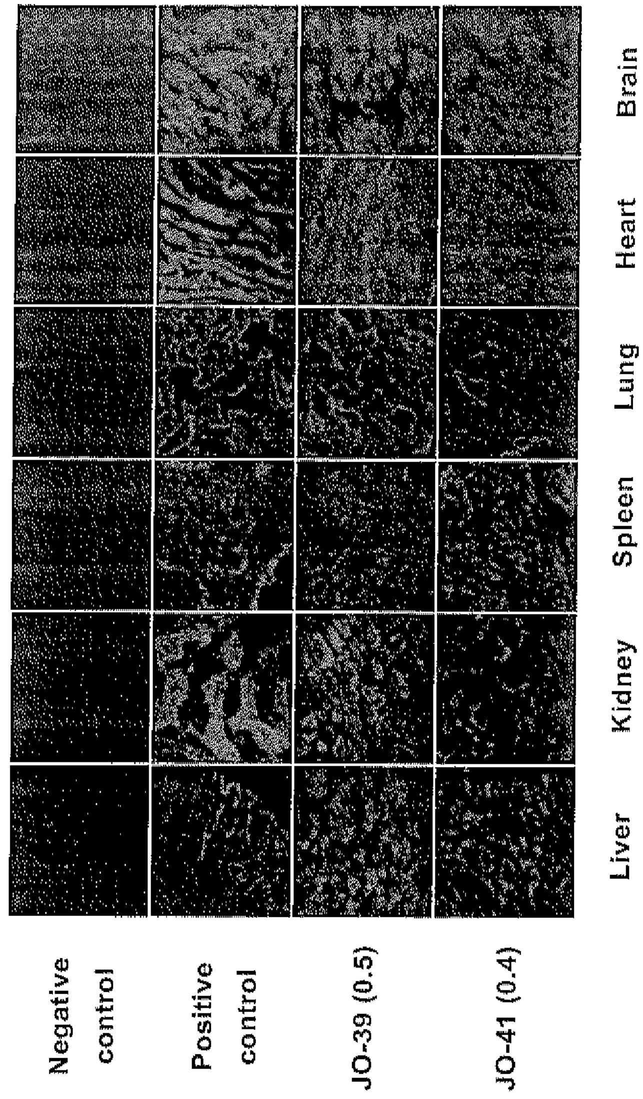
FIG. 3 is of confocal laser scanning microscopy photographs visualizing the tissue permeability of JO-39 and JO-41 MTDs in various murine tissues.

As can be seen in FIG. 3, the FITC fluorescence (light green) was distributed over the tissues, which was consistent with the relative cell permeability determined by flow cytometry above. From these results, it is understood that JO-39 MTD and JO-41 MTD, used as macromolecule transduction domains in the present invention, have excellent tissue permeability so that they can effectively introduce target proteins into tissues.

Example 3

Construction of Cell- and Tissue-Permeable P53 Recombinant Protein (CP-p53)

<3-1> JO-39 MTD ($MTD_{39}$) and JO-41 MTD ($MTD_{41}$), identified for cell and tissue permeability in Examples 1 and 2, was used to prepare cell-permeable p53 recombinant proteins in the following full-length or truncated forms (FIGS. 4 and 5):

1) His-NLS-p53 (HNp53) in which His-NLS is fused to the N-terminus of full-length p53, 2) His-NLS-$MTD_{39}$-p53 ($HNM_{39}$p53) in which His-NLS and JO-39 MTD are fused to the N-terminus of full-length p53, 3) His-NLS-p53-$MTD_{39}$ (HNp53$M_{39}$) in which His-NLS and JO-39 MTD are fused to the N- and C-terminus of full-length p53, respectively, 4) His-NLS-$MTD_{39}$-p53-$MTD_{39}$ ($HNM_{39}$p53$M_{39}$) in which His-NLS-JO39MTD and JO-39 MTD are fused to the N- and C-terminus of full-length p53, respectively, 5) His-NLS-$MTD_{41}$-p53 ($HNM_{41}$p53) in which His-NLS and JO-41 MTD are fused to the N-terminus of full-length p53, 6) His-NLS-p53-$MTD_{41}$ (HNp53$M_{41}$) in which His-NLS and JO-41 MTD are fused to the N- and C-terminus of full-length p53, respectively, 7) His-NLS-$MTD_{41}$-p53-$MTD_{41}$ ($HNM_{41}$p53 $M_{41}$) in which His-NLS-JO41MTD and JO-41 MTD are fused to the N- and C-terminus of full-length p53, 8) His-NLS-Δp53 (HNΔp53) in which His-NLS is fused to the N-terminus of truncated p53, 9) His-Δp53 (HΔp53) in which His-Tag is fused to the N-terminus of truncated p53, 10) His-NLS-$MTD_{39}$-Δp53 ($HNM_{39}$Δp53) in which His-NLS and JO-39 MTD are fused to the N-terminus of truncated p53, 11) His-NLS-Δp53-$MTD_{39}$ (HNΔp53$M_{39}$) in which His-Tag and JO-39 MTD are fused to the N-terminus of truncated p53, 12) His-NLS-$MTD_{41}$-Δp53 ($HNM_{41}$Δp53) in which His-NLS and JO-41 MTD are fused to the N-terminus of truncated p53, 13) His-NLS-Δp53-$MTD_{41}$ (HNΔp53$M_{41}$) in which His-NLS and JO-41 MTD are fused to the N- and C-terminus of truncated p53, respectively, 14) His-$MTD_{39}$-Δp53 ($HM_{39}$Δp53) in which His-Tag and JO-39 MTD are fused to the N-terminus of truncated p53, 15) His-Δp53-$MTD_{39}$ (HΔp53$M_{39}$) in which His-Tag and JO-39 MTD are fused to the N- and C-terminus of truncated p53, respectively, 16) His-$MTD_{41}$-Δp53 ($HM_{41}$Δp53) in which His-Tag and JO-41 MTD are fused to the N-terminus of truncated p53

17) His-Δp53-$MTD_{41}$ (HΔp53$M_{41}$) in which His-Tag and JO-41 MTD are fused to the N- and C-terminus of truncated p53, respectively, To prepare gene constructs corresponding to the recombinant proteins, PCR (polymerase chain reaction) was performed on the template of human p53 cDNA in the presence of pairs of the following specifically designed primers:

Forward and reverse primers for amplifying HNp53, having nucleotide sequences of SEQ ID NO: 79 and 82, respectively;

Forward and reverse primers for amplifying $HNM_{39}$p53, having nucleotide sequences of SEQ ID NO: 80 and 82, respectively;

Forward and reverse primers for amplifying HNp53$M_{39}$, having nucleotide sequences of SEQ ID NO: 79 and 83, respectively;

Forward and reverse primers for amplifying $HNM_{39}$p53$M_{39}$, having nucleotide sequences of SEQ ID NO: 80 and 83, respectively;

Forward and reverse primers for amplifying $HNM_{41}$p53, having nucleotide sequences of SEQ ID NO: 81 and 82, respectively;

Forward and reverse primers for amplifying HNp53$M_{41}$, having nucleotide sequences of SEQ ID NO: 79 and 84, respectively;

Forward and reverse primers for amplifying $HNM_{41}$p53$M_{41}$, having nucleotide sequences of SEQ ID NO: 81 and 84, respectively;

Forward and reverse primers for amplifying HΔp53, having nucleotide sequences of SEQ ID NO: 85 and 88, respectively;

Forward and reverse primers for amplifying $HM_{39}$Δp53, having nucleotide sequences of SEQ ID NO: 86 and 88, respectively;

Forward and reverse primers for amplifying $HM_{41}$Δp53, having nucleotide sequences of SEQ ID NO: 87 and 88, respectively.

The forward and reverse primers used for amplifying the gene constructs are summarized in Table 2, below.

TABLE 2

| Primer | Sequence |
|---|---|
| 5'-HNp53 | 5'-CCG CAT ATG AAG AAG AAG AGG AAG GAG GAG CCG CAG TCA GAT CCT AGC-3' |
| 5'-HNM$_{39}$p53 | 5'-CCG CAT ATG AAG AAG AAG AGG AAG CCG CTG GTG CTG GCG ATT GCG GCG GTG CTG GAG GAG CCG CAG TCA GAT CCT AGC-3' |
| 5'-HNM$_{41}$p53 | 5'-CCG CAT ATG AAG AAG AAG AGG AAG GCG GCG GCG CTG CTG GCG GTG GCG GAG GAG CCG CAG TCA GAT CCT AGC-3' |
| 3'-HNp53 | 5'-CCG CAT ATG TCA GTC TGA GTC AGG CCC TTC TGT CTT-3' |
| 3'-HNp53M$_{39}$ | 5'-CCG CAT ATG TCA CAG CAC CGC CGC AAT CGC CAG CAC CAG CGG GTC TGA GTC AGG CCC TTC TGT CTT-3' |
| 3'-HNp53M$_{41}$ | 5'-CCG CAT ATG TCA CGC CAC CGC CAG CAG CGC CGC CGC GTC TGA GTC AGG CCC TTC TGT CTT-3' |
| 5'-HΔp53 | 5'-CCG CAT ATG GAG GAG CCG CAG TCA GAT CCT AGC-3' |
| 5'-HM$_{39}$Δp53 | 5'-CCG CAT ATG CCG CTG GTG CTG GCG ATT GCG GCG GTG CTG GAG GAG CCG CAG TCA GAT CCT AGC-3' |
| 5'-HM$_{41}$Δp53 | 5'-CCG CAT ATG GCG GCG GCG CTG CTG GCG GTG GCG GAG GAG CCG CAG TCA GAT CCT AGC-3' |
| 3'-HNΔp53 | 5'-CCG CAT ATG TCA GGT TTT CTG GGA AGG GAC AGA AGA-3' |
| 3'-HNΔp53M$_{39}$ | 5'-CCG CAT ATG TCA CAG CAC CGC CGC AAT CGC CAG CAC CAG CGG GGT TTT CTG GGA AGG GAC AGA AGA-3' |
| 3'-HNΔp53M$_{41}$ | 5'-CCG CAT ATG TCA CGC CAC CGC CAG CAG CGC CGC CGC GGT TTT CTG GGA AGG GAC AGA AGA-3' |

Figure 6:
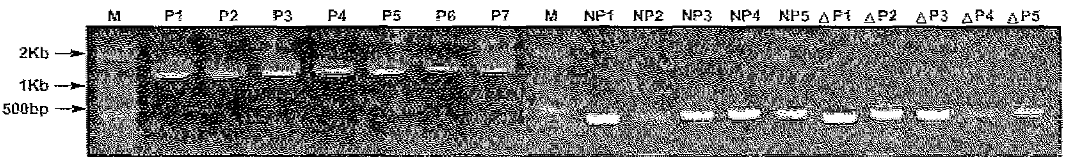
FIG. 6 is a photograph showing PCR-amplified cDNA fragments encoding full-length and truncated forms of the recombinant p53 proteins in which JO-39 and JO-41 MTDs have each been fused to a full-length or truncated p53 protein in accordance with the present invention.

The PCR was performed in a final volume of 100 μL of a reaction mixture containing 100 ng of human p53 cDNA as a template, 0.2 mM dNTP mixture (dGTP, dATP, dTTP, and dCTP, each at 2 mM), 0.5 μM of each primer, 10 μL of 10×Taq buffer, and 0.5 μL of Taq polymerase (Takara, Japan). The PCR was started at 95° C. and 2 min to allow initial denaturation, and then 30 thermal cycles were carried out at 95° C. for 45 sec, at 67° C. for 45 sec and at 72° C. for 45 sec, followed by the final extension at 72° C. for 5 min. After completion of PCR, the PCR products thus obtained were identified on 0.8% agarose gel by electrophoresis. As shown in FIG. 6, MTD-fused recombinant gene constructs were successfully amplified.

Figure 7:
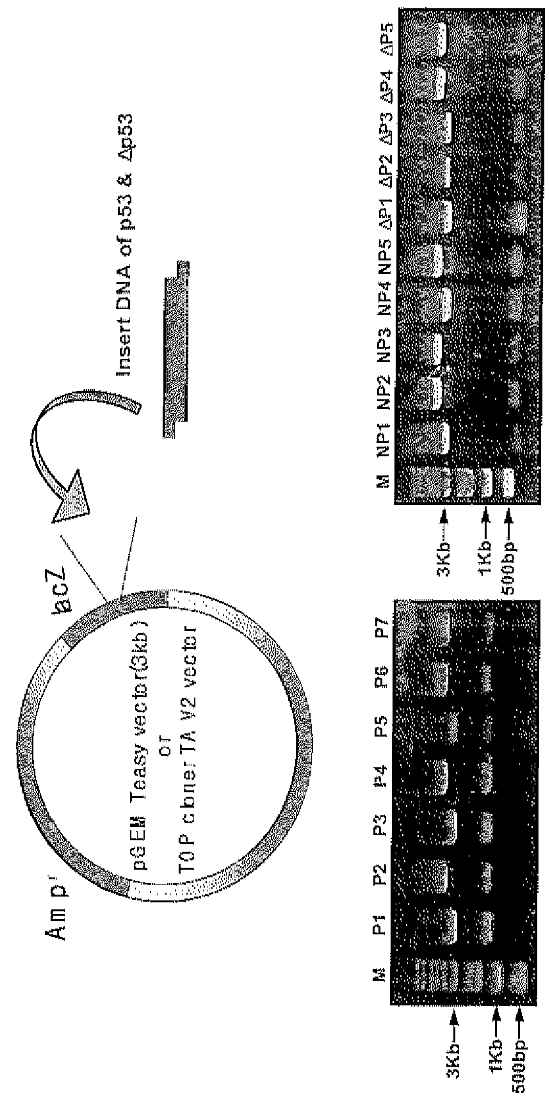
FIG. 7 shows the cloning of the PCR products of FIG. 6 into a pGEM-T Easy vector.

The DNA bands of expected sizes were excised from the gel, eluted, and purified with the aid of a QIAquick Gel extraction kit (Qiagen, USA). The eluted DNA was inserted into pGEM-T Easy (Promega, USA) (FIG. 7). The resulting recombinant pGEM-T Easy vector carrying the MTD-fused p53 recombinant genes was transformed into *E. coli* DH5α competent cells which were then spread over LB plates containing 50 μg/mL ampicillin and cultured overnight at 37° C. After being picked up, transformants were cultured in LB broth, and the recombinant pGEM-T Easy vectors carrying respective genes coding for the p53 recombinant proteins were prepared from the bacteria.

With reference to FIG. 7, there is 0.8% agarose gel in which the DNA fragments isolated by treating the recombinant pGEM-T Easy vector with the restriction enzyme NdeI (Enzynomics, Korea) is separated by electrophoresis, confirming that the DNA constructs were appropriately cloned into the vector.

Digestion of the recombinant pGEM-T Easy vector with the restriction enzyme NdeI at 37° C. for 2 hours produced gene fragments of the p53 recombinant proteins. The DNA bands of desired sizes were excised from the gel, eluted, and purified with the aid of a QIAquick Gel extraction kit (Qiagen, USA). pET-28(+) (Novagen, Madison, Wis.), which bears a histidine-tag and a T7 promoter, was digested with the restriction enzyme NdeI (Enzynomics, Korea) under the same conditions. Each of the DNA fragments was ligated to the digested pET-28a(+) vector in the presence of T4 DNA ligase at 16° C. for 12 hours, followed by transforming *E. coli* DH5α competent cells with the resulting recombinant pET-28a(+) vector.

Figure 8:
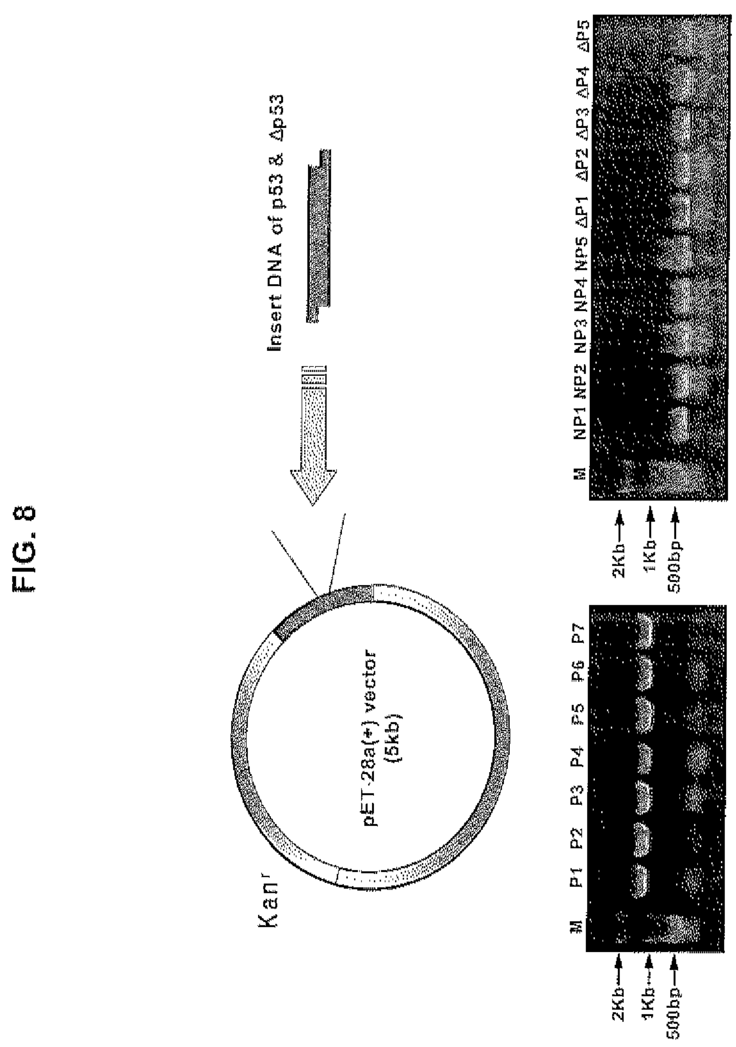
FIG. 8 shows the construction of a recombinant expression vector by cloning the p53 recombinant fragment of the present invention into a pET-28a(+) expression vector.

Referring to FIG. 8, there is 0.8 agarose gel in which digests resulting from the digestion of the recombinant pET-28a(+) vector with the restriction enzyme NdeI are separated by electrophoresis, confirming the appropriate insertion of the DNA fragments into the vector.

The recombinant expression vectors thus constructed were named pET28a(+)-HNp53, pET28a(+)-HNM$_{39}$p53, pET28a (+)-HNM$_{41}$p53, pET28a (+)-HNp53M$_{39}$, pET28a (+)-HNp53M$_{41}$, pET28a (+)-HNM$_{39}$p53M$_{39}$, pET28a (+)-HNM$_{41}$p53M$_{41}$, pET28a(+)-HNΔp53, pET28a(+)-HNM$_{39}$Δp53 and pET28a(+)-HNM$_{41}$Δp53, pET28a(+)-HΔp53, pET28a(+)-HM$_{39}$Δp53, and pET28a(+)-HM$_{41}$Δp53, respectively. Of them, the recombinant expression vectors pET28a(+)-HNM$_{39}$Δp53 and pET28a(+)-HM$_{39}$Δp53 were transformed into DH5α, and the transformants, named DH5α/HNM$_{39}$Δp53 and DH5α/HM$_{39}$Δp53, were deposited on Nov. 17, 2009 with the Biological Resource Center of the Korea Research Institute of Bioscience and Biotechnology, under accession Nos. KCTC 11596BP and KCTC 11595BP, respectively.

Base sequencing identified full-length forms of the p53 recombinant proteins constructed with JO-39 MTD (MTD$_{39}$), which were named:

His-NLS-p53 (HNp53), having the amino acid sequence of SEQ ID NO: 46, encoded by a polynucleotide having the nucleotide sequence of SEQ ID NO: 45;

His-NLS-MTD$_{39}$-p53 (HNM$_{39}$p53), having the amino acid sequence of SEQ ID NO: 48, encoded by a polynucleotide having the nucleotide sequence of SEQ ID NO: 47;

His-NLS-p53-MTD$_{39}$ (HNp53M$_{39}$), having the amino acid sequence of SEQ ID NO: 50, encoded by a polynucleotide having the nucleotide sequence of SEQ ID NO: 49;

His-NLS-MTD$_{39}$-p53-MTD$_{39}$ (HNM$_{39}$p53M$_{39}$), having the amino acid sequence of SEQ ID NO: 52, encoded by a polynucleotide having the nucleotide sequence of SEQ ID NO: 51.

Full-length forms of p53 recombinant proteins constructed with JO-41 MTD (MTD$_{41}$) were named and identified as follows:

His-NLS-MTD$_{41}$-p53 (HNM$_{41}$p53), having the amino acid sequence of SEQ ID NO: 54, encoded by a polynucleotide having the nucleotide sequence of SEQ ID NO: 53;

His-NLS-p53-MTD$_{41}$ (HNp53M$_{41}$), having the amino acid sequence of SEQ ID NO: 56, encoded by a polynucleotide having the nucleotide sequence of SEQ ID NO: 55;

His-NLS-MTD$_{41}$-p53-MTD$_{41}$ (HNM$_{41}$p53M$_{41}$), having the amino acid sequence of SEQ ID NO: 58, encoded by a polynucleotide having the nucleotide sequence of SEQ ID NO: 57.

Base sequencing identified truncated forms of p53 recombinant proteins constructed with JO-39 MTD ($MTD_{39}$), named:

His-$MTD_{39}$-Δp53 ($HM_{39}$Δp53), having the amino acid sequence of SEQ ID NO: 64, encoded by a polynucleotide having the nucleotide sequence of SEQ ID NO: 63;

His-Δp53-$MTD_{39}$ (HΔp53$M_{39}$), having the amino acid sequence of SEQ ID NO: 66, encoded by a polynucleotide having the nucleotide sequence of SEQ ID NO: 65;

His-NLS-$MTD_{39}$-Δp53 ($HNM_{39}$Δp53), having the amino acid sequence of SEQ ID NO: 68, encoded by a polynucleotide having the nucleotide sequence of SEQ ID NO: 67;

His-NLS-Δp53-$MTD_{39}$ (HNΔp53$M_{39}$), having the amino acid sequence of SEQ ID NO: 70, encoded by a polynucleotide having the nucleotide sequence of SEQ ID NO: 69;

Truncated forms of p53 recombinant proteins constructed with JO-41 MTD ($MTD_{41}$) were named and identified as follows:

His-$MTD_{41}$-Δp53 ($HM_{41}$Δp53), having the amino acid sequence of SEQ ID NO: 72, encoded by a polynucleotide having the nucleotide sequence of SEQ ID NO: 71;

His-Δp53-$MTD_{41}$ (HΔp53$M_{41}$), having the amino acid sequence of SEQ ID NO: 74, encoded by a polynucleotide having the nucleotide sequence of SEQ ID NO: 73;

His-NLS-$MTD_{41}$-Δp53 ($HNM_{41}$Δp53), having the amino acid sequence of SEQ ID NO: 76, encoded by a polynucleotide having the nucleotide sequence of SEQ ID NO: 75;

His-NLS-Δp53-$MTD_{41}$ (HNΔp53$M_{41}$), having the amino acid sequence of SEQ ID NO: 78, encoded by a polynucleotide having the nucleotide sequence of SEQ ID NO: 77.

For use as a control for the cell-permeable p53 recombinant proteins in the present invention, a p53 recombinant protein was constructed with a nuclear localization sequence, but without MTD, and named His-NLS-p53 (HNp53), which has the amino acid sequence of SEQ ID NO: 46, encoded by a polynucleotide having the nucleotide sequence of SEQ ID NO: 45.

For use an another control for the cell-permeable Δp53 recombinant proteins in the present invention, a Δp53 recombinant protein was constructed with a His-tag, but without MTD, and named His-Δp53 (HΔp53), which has the amino acid sequence of SEQ ID NO: 60, encoded by a polynucleotide having the nucleotide sequence of SEQ ID NO: 59.

Also, for use as a further control for the Δp53 recombinant proteins, a Δp53 recombinant protein was constructed with His-tag and NLS, but without MTD, and named His-NLS-Δp53 (HNΔp53), which has the amino acid sequence of SEQ ID NO: 62, encoded by a polypeptide having the nucleotide sequence of SEQ ID NO: 61.

Example 4

Expression of Recombinant Proteins

<4-1> Selection of Optimal Host Strain

To choose a host strain optimal for the expression of cell permeable p53 recombinant proteins, the following experiments were carried out in *E. coli* BL21(DE3), BL21 Gold (DE3), BL21 CodonPlus(DE3) and BL21 Gold(DE3) pLysS (Stratagene, USA), all containing a Lad promoter.

Each of the recombinant expression vectors constructed in Example 3-1 was transformed into the *E. coli* strains BL21 (DE3), BL21 Gold(DE3), BL21 CodonPlus(DE3) and BL21-Gold(DE3) pLysS by heat shock, followed by incubation on LB plates containing 50 μg/ml of kanamycin. Transformants formed on the LB plates were seed cultured overnight at 37° C. in 1 mL of LB broth and then mass cultured in 100 mL of LB broth at 37° C. until the optical density at 600 nm ($OD_{600}$) reached 0.6 to 0.7. To the cell culture was added 1 mM isopropyl-β-D-thiogalactoside (IPTG), followed by incubation at 37° C. for 3 hours to induce the expression of the recombinant proteins. The cells were harvested by centrifugation at 4° C., 7,000×g for 20 min. and the cell pellets thus obtained were resuspended in a lysis buffer (100 mM $NaH_2PO_4$, 10 mM Tris-HCl, 8 M urea, pH 8.0), and lyzed by ultrasonication. The cell lysates were centrifuged at 14,000×g for 15 min, so as to separate an insoluble fraction from a soluble fraction. The soluble and insoluble fractions were loaded on SDS-PAGE gel to analyze expression properties and amounts.

The analysis data allowed BL21 CodonPlus (DE3) to be selected as an optimal strain for the expression of the recombinant proteins of the present invention as the recombinant proteins were detected at the highest level in the strain.

<4-2> Expression of Recombinant Proteins

BL21 CodonPlus (DE3), identified as an optimal strain in Example 4-1, was transformed with each of the recombinant expression vectors pET28a(+)-HNp53, pET28a(+)-$HNM_{39}$p53, pET28a(+)-$HNM_{41}$p53, pET28a(+)-HNp53$M_{39}$, pET28a(+)-HNp53$M_{41}$, pET28a(+)-$HNM_{39}$p53$M_{39}$, pET28a(+)-$HNM_{41}$p53$M_{41}$, pET28a(+)-HNΔp53, pET28a(+)-$HNM_{39}$Δp53, pET28a(+)-$HNM_{41}$Δp53, pET28a(+)-HΔp53, pET28a(+)-H $M_{39}$Δp53, and pET28a(+)-$HM_{41}$Δp53 by heat shock and then incubated in LB plates containing 50 μg/mL kanamycin. The transformants formed on the plates were incubated overnight at 37° C. in 25 mL of LB broth and then amplified at 37° C. in 1 L of LB broth until $OD_{600}$ reached 0.6 to 0.7. Protein expression was induced by incubation at 37° C. for 3 hours in the presence of 0.65 mM IPTG. The cells were harvested by centrifugation at 4° C., 4,000×g for 20 min and the cell pellets thus obtained were resuspended in a lysis buffer (100 mM $NaH_2PO_4$, 10 mM Tris-HCl, 8 M urea, pH 8.0) and lyzed by ultrasonication. The cell lysates were centrifuged at 14,000×g for 15 min, so as to separate an insoluble fraction from a soluble fraction. The soluble and insoluble fractions were loaded on SDS-PAGE gel to analyze expression properties and amounts.

Figure 9:
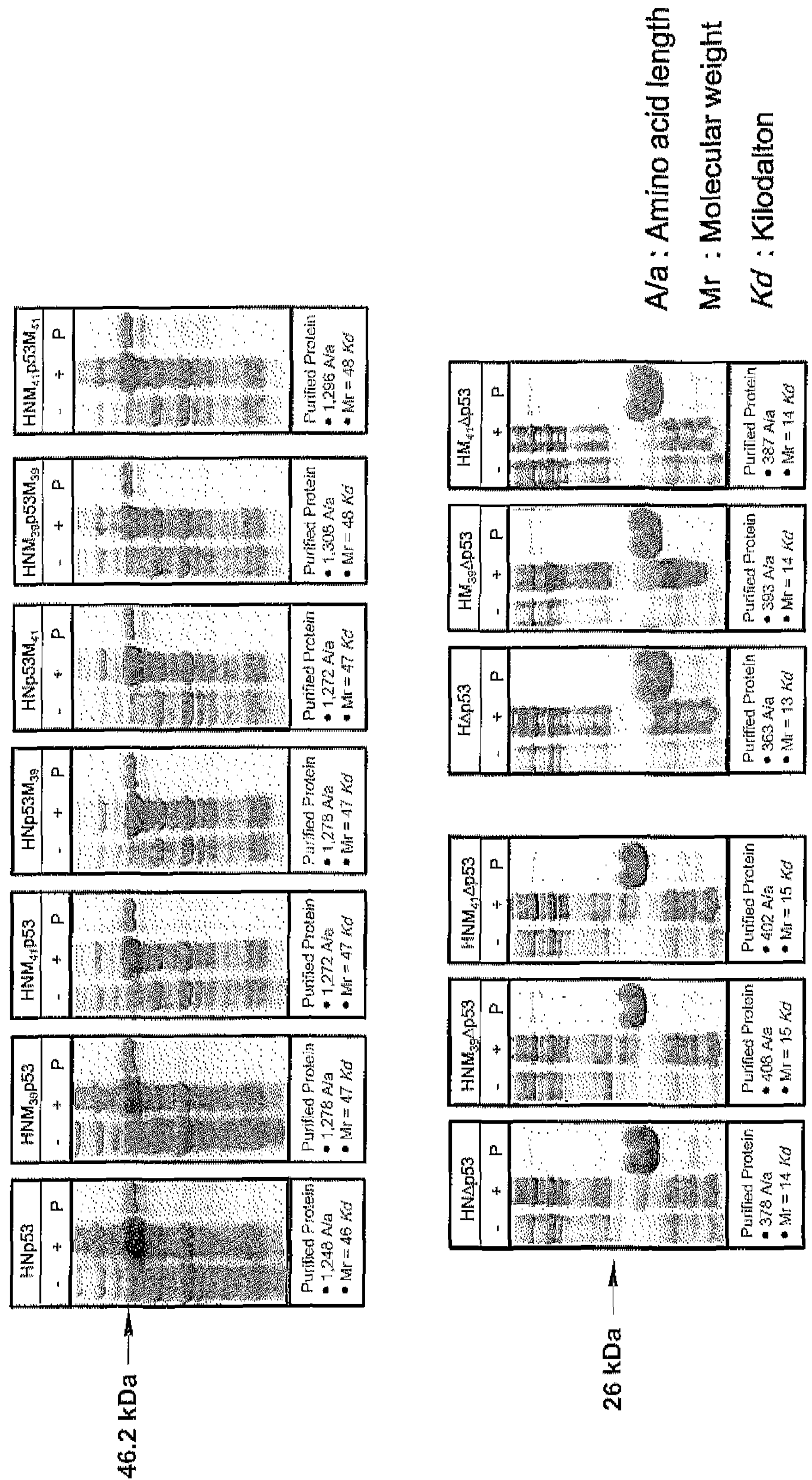
FIG. 9 shows the expression of the p53 recombinant protein of the present invention in the presence (+) or absence (−) of IPTG, an expression inducer.

As shown in FIG. 9, the cell-permeable p53 recombinant proteins with a molecular weight of about 53 kDa were present predominantly as an inclusion body in the insoluble fraction and their expression in the IPTG-treated culture (+) was significantly increased compared to that in the IPTG-non-treated culture (−).

Example 5

Purification of Recombinant Proteins

Because the cell-permeable p53 recombinant proteins of the present invention existed as inclusion bodies in insoluble fractions, they were solubilized under denaturing conditions with 8 M urea as a potent denaturant.

The BL21 Gold(DE3) strain transformed with each of the expression vectors of the present invention were cultured in 1 L of LB broth as described in Example 3. The cells were harvested by centrifugation, resuspended in 20 mL of a lysis buffer (100 mM $NaH_2PO_4$, 10 mM Tris-HCl, 8 M urea, pH 8.0) with care taken to avoid foaming. The cell lysate was homogenized using a sonicator equipped with a microtip. In this regard, the cells were sonicated for a total of 7 min at 25% of the maximal power of the apparatus, with cycles of sonication for 45 sec and intermittence for 10 sec. The sufficiently lyzed cells were centrifuged at 4° C. and 4,000×g for 20 min to pelletize cell debris. The supernatant thus obtained was placed onto a Ni-NTA agarose resin where nitrilotriacetic acid agarose was charged with nickel (Ni). The Ni-NTA agarose resin was previously equilibrated with the lysis buffer. The supernatant was allowed to be absorbed onto the resin by gently shaking at 4° C. for 8 hours or longer. The resin loaded with the inclusion bodies containing the recombinant protein was centrifuged at 4° C. and 1,000 rpm for 5 min, to remove the reaction solution, and was then washed five times with a washing buffer (100 mM $NaH_2PO_4$, 10 mM Tris-HCl, 8 M urea, pH 6.3) to remove non-specifically absorbed materials. To the cleaned resin were loaded two volumes of an elution buffer (100 mM $NaH_2PO_4$, 10 mM Tris-HCl, 8 M urea, pH 4.5) under acidic condition (pH 4.0), followed by shaking for 2 or 8 hours so as to elute the proteins from the resin. The eluted proteins were analyzed by 12% SDS-PAGE gel electrophoresis, stained with Coomassie Brilliant Blue R with gentle shaking, and destained with a destaining solution until bands of target proteins were clearly visualized.

As can be seen in FIG. 9, all of the cell permeable p53 recombinant proteins constructed with JO-39 MTD and JO-41 MTD were detected as a single band corresponding to about 53 kDa, with reference to the marker, indicating that the cell permeable p53 recombinant proteins of the present invention have been purified from the insoluble fraction.

Example 6

Refolding of Recombinant Proteins

Because the cell-permeable p53 recombinant proteins purified from the insoluble fraction as described in Example 5 were denatured by the potent denaturant 8 M urea, the denatured proteins were allowed to refold into their active forms, as follows.

To begin with, the dissolved recombinant proteins were renatured by removing the denaturant by means of dialysis against a refolding buffer (0.55 M guanidine HCl, 0.88 M L-arginine, 50 mM Tris-HCl, 150 mM NaCl, 1 mM EDTA, 100 mM NDSB, 1 mM glutathione oxidized, and 1 mM glutathione reduced) at 4° C. for 72 hours, with the exchange of the refolding buffer with a fresh one every 24 hours. Subsequently, the refolded recombinant proteins were again dialyzed against DMEM (Dulbecco's Modified Eagle Medium) containing 1% penicillin/streptomycin in dialysis tubing (Snakeskin pleated, PIERCE) at 4° C. for 9 hours with stirring. The medium was replaced with a fresh one every three hours. The cell permeable p53 recombinant proteins converted into their active form through the refolding process were used in subsequent experiments.

Example 7

Assay of Selected MTD for Cell Permeability

<7-1> Flow Cytometry

In order to quantitatively analyze the cell permeability of the cell permeable Δp53 recombinant proteins according to the present invention, the transduction of the proteins into the cell was monitored by FACS (fluorescence-activated cell sorting) in mammalian cells, as follows.

The cell permeable p53 recombinant proteins purified as soluble forms were conjugated with FITC (fluorescein-5-isothiocyanate, Molecular Probe). In this regard, 2 to 20 mg of the recombinant protein was mixed and reacted with 1 μL of 333 mg/mL FITC under a condition of darkness at room temperature for 1 hour with stirring. The reaction solution was subjected to dialysis against DMEM at 4° C. for 1 day to remove the unreacted FITC. Each of the FITC-conjugated recombinant proteins thus obtained was found to have a concentration of approximately 1 μg/μL as quantitatively analyzed by Bradford protein assay.

Meanwhile, RAW 264.7 cells (the Korean Cell Line Bank, Seoul, Korea), derived from mouse macrophage, were maintained in DMEM supplemented with 10% fetal bovine serum (FBS) and 1% penicillin/streptomycin (500 mg/ml) and incubated at 37° C. in a moist, 5% $CO_2$ atmosphere.

After incubation, the cells were treated with 10 μM of each of the FITC-conjugated Δp53 recombinant proteins ($HM_{39}$Δp53, $HM_{41}$Δp53, $HNM_{39}$Δp53, $HNM_{41}$Δp53) and incubated at 37° C. for one hour. Subsequently, the cells were treated with trypsin/EDTA (T/E, Invitrogen) to remove free FITC exposed on the cell surface, and washed three times with cold PBS (phosphate buffered saline). The FITC-conjugated recombinant p53 proteins were subjected to FACScan (Becfkton-Dickinson, Calif.) for flow cytometry and analyzed with the aid of the CellQuest Pro software program. For each sample containing cells at a concentration of $1\times10^4$ cells/μL, two or more independent experiments were performed. The cell permeability of the cell permeable p53 recombinant proteins according to the present invention was determined in comparison with that of the control protein (Hp53) devoid of MTD.

Figure 10:
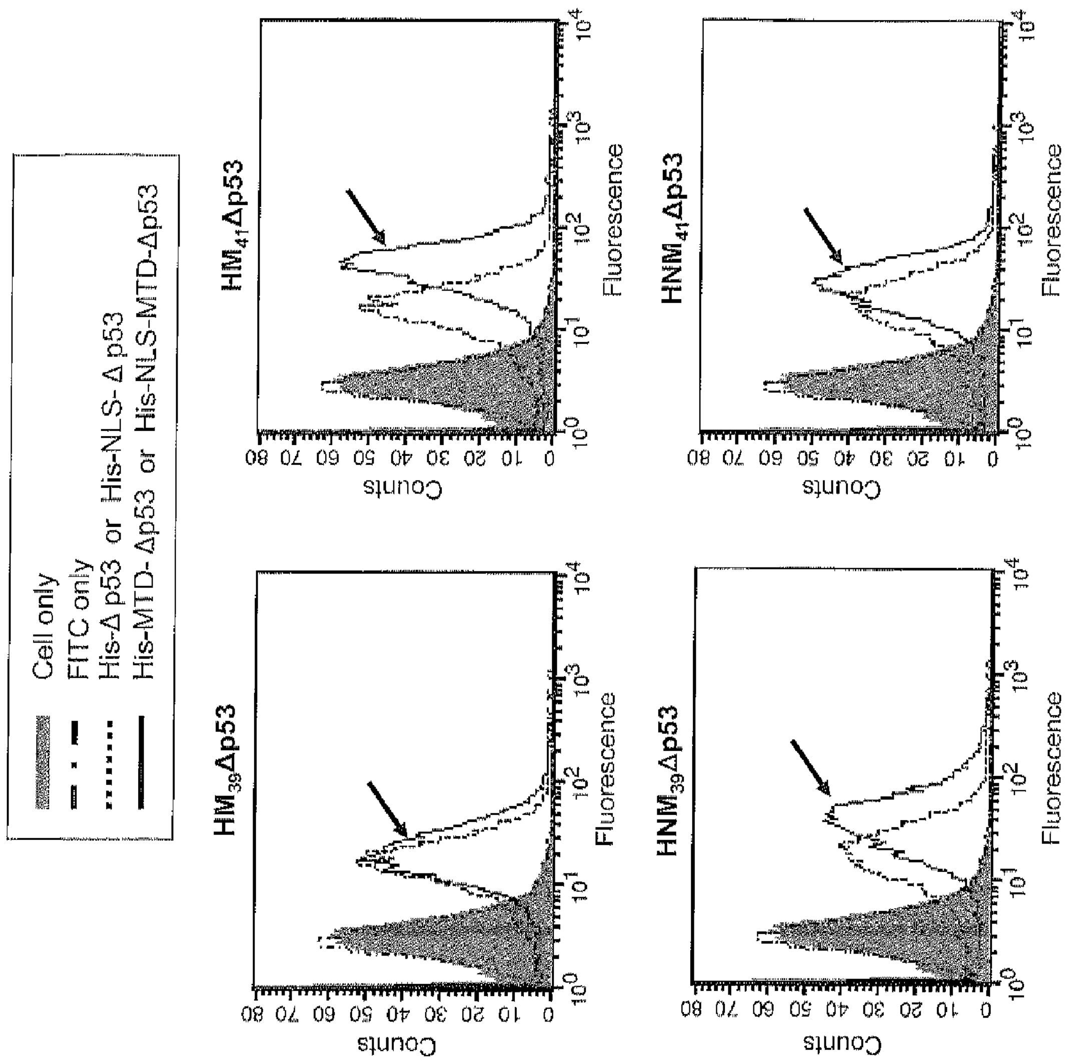
FIG. 10 is of graphs illustrating the results of flow cytometric analysis for the cell permeability of p53 recombinant proteins in which JO-39 MTD or JO-41 MTD is, together with a nuclear localization sequence (NLS), fused to truncated p53.

As is clearly understood from the data of FIG. 10, all of the cell-permeable p53 recombinant proteins according to the present invention are more able to transverse across the cell membrane, compared to the control. In FIG. 10, the gray filled curve accounts for cells only, the curve of black dotted line 1 (_ . _ .) for FITC alone, the curve of dotted line 2 (. . . . . . . .) for controls (HΔp53, HNΔp53) devoid of MTD, and the curve of solid line (__________) for the cell-permeable recombinant proteins $HM_{39}$Δp53, $HNM_{39}$Δp53, $HM_{41}$Δp53, and $HNM_{41}$Δp53.

<7-2> Confocal Laser Scanning Microscopy II

To visualize the intracellular localization of the cell-permeable p53 recombinant protein, identified as being permeable into cells in the flow cytometry of the previous Example Section, NIH 3T3 cells (Korean Cell Line Bank, Seoul, Korea), derived from mouse fibroblasts, were treated with 10 μM of the FITC-conjugated recombinant proteins ($HNM_{39}$p53, $HNM_{41}$p53, HNp53$M_{39}$, HNp53$M_{41}$, $HNM_{39}$p53$M_{39}$ and $HNM_{41}$p53$M_{41}$) and incubated at 37° C. for one hour before visualization under a confocal laser scanning microscope. In this context, NIH 3T3 cells were incubated using an 8-well chamber slide (LabTek, Nalgen Nunc) for 24 hours. The NIH3T3 cells were grown at 37° C. in DMEM supplemented with 10% FBS and 5% penicillin/streptomycin (500 mg/ml) under a 5% $CO_2$ atmosphere. The cells were washed three times with PBS and then incubated at 37° C. for one hour with serum-free DMEM, serum-free DMEM containing FITC, or serum-free DMEM containing 10 μM of each of the FITC-conjugated recombinant proteins under a 5% $CO_2$ atmosphere. Thereafter, the cells were fixed at room temperature for 20 min with 4% paraformaldehyde.

To examine nuclear translocation and cell permeability by discriminating intracellular localization sites of MTD that was internalized, nuclei of the fixed cells were counterstained with the nuclear fluorescent stain solution PI (propidium iodide, Sigma-Aldrich). After counterstaining for 5 min with 1 μg/mL PI, the cells were washed three times with PBS. In order to preserve the FITC fluorescence of the recombinant protein, the glass slide was fixed in 10 μL of a polyvinyl alcohol mounting medium containing DABCO (Fluca) for 15 min before making observations. The intracellular distribution of the fluorescence was visualized with a confocal laser scanning microscope equipped with a normaski filter. Cell morphology, FITC fluorescence and PI fluorescence were observed. FITC was excited at 488 nm and detected by means of a bandpass filter at 530 nm.

Figure 11:
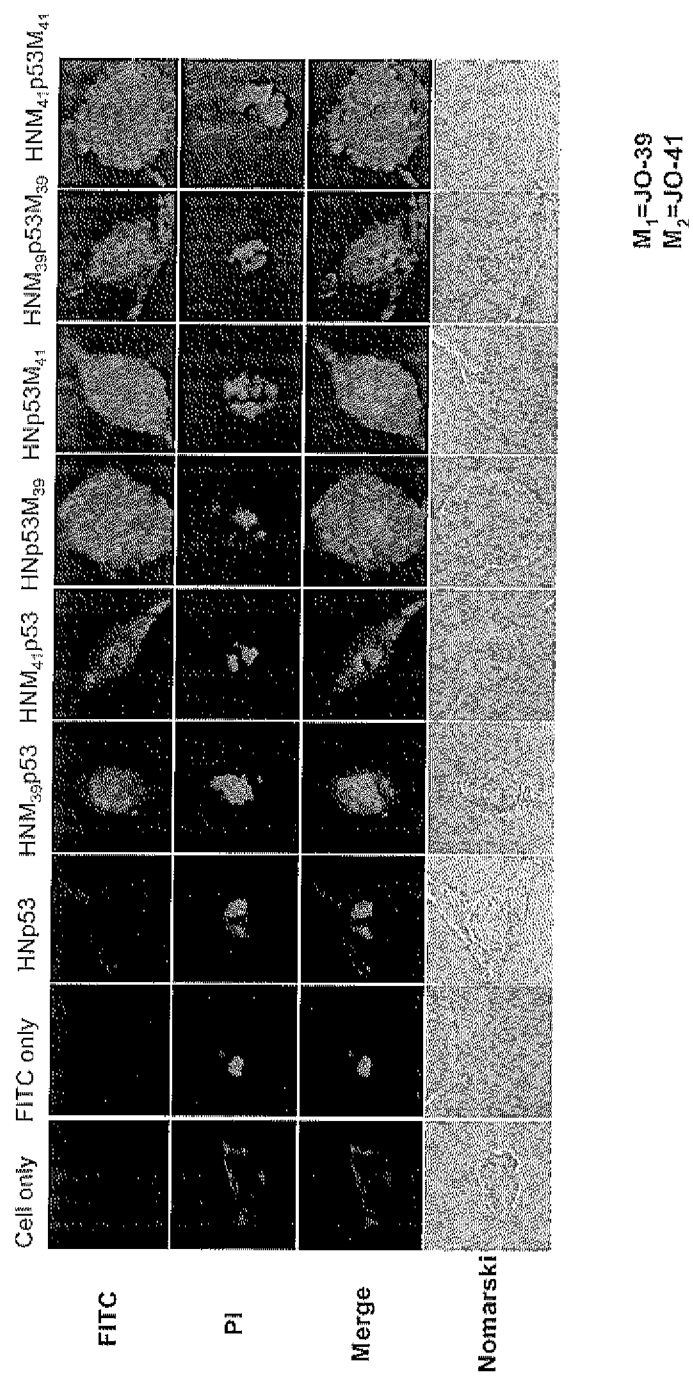
FIG. 11 is of confocal laser scanning microscopy photographs visualizing the cell permeability of p53 recombinant proteins in which JO-39 MTD or JO-41 MTD is fused, together with a nuclear localization sequence (NLS), to full-length p53.

As shown in FIG. 11, it was understood that the FITC-conjugated cell permeable proteins according to the present invention were clearly localized within the cell nucleus, as compared with the cell only, FITC only, and the control devoid of MTD (HNp53). The nuclear localization of the cell-permeable p53 recombinant proteins constructed with JO-39 MTD and JO-41 MTD was consistent with the relative cell permeability determined above by flow cytometry.

<7-3> Confocal Laser Scanning Microscopy III

For visual detection of the intracellular localization of the cell-permeable p53 recombinant protein, identified as being permeable into cells by means of the flow cytometry of the previous Example Section, NIH 3T3 cells (Korean Cell Line Bank, Seoul, Korea), derived from mouse fibroblasts, were treated with 10 μM of the FITC-conjugated truncated p53 recombinant proteins ($HNM_{39}\Delta p53$ and $HNM_{41}\Delta p53$) and incubated at 37° C. for one hour before visualization under a confocal laser scanning microscope. In this context, NIH 3T3 cells were incubated using an 8-well chamber slide (LabTek, Nalgen Nunc) for 24 hours. The NIH3T3 cells were maintained in DMEM supplemented with 10% FBS and 5% penicillin/streptomycin (500 mg/ml). The cells were washed three times with PBS and then incubated at 37° C. for one hour with serum-free DMEM, serum-free DMEM containing FITC, or serum-free DMEM containing 10 μM of each of the FITC-conjugated recombinant proteins under a 5% $CO_2$ atmosphere. Thereafter, the cells were fixed at room temperature for 20 min with 4% paraformaldehyde.

To examine nuclear translocation and cell permeability by discriminating intracellular localization sites of MTD that was internalized, nuclei of the fixed cells were counterstained with the nuclear fluorescent stain solution PI (propidium iodide, Sigma-Aldrich). After counterstaining for 5 min with 1 μg/mL PI, the cells were washed three times with PBS. In order to preserve the FITC fluorescence of the recombinant protein, the glass slide was fixed in 10 μL of a polyvinyl alcohol mounting medium containing DABCO (Fluca) for 15 min before making observations. The intracellular distribution of the fluorescence was visualized with a confocal laser scanning microscope equipped with a normaski filter. Cell morphology, FITC fluorescence and PI fluorescence were observed. FITC was excited at 488 nm and detected by means of a bandpass filter at 530 nm.

Figure 12:
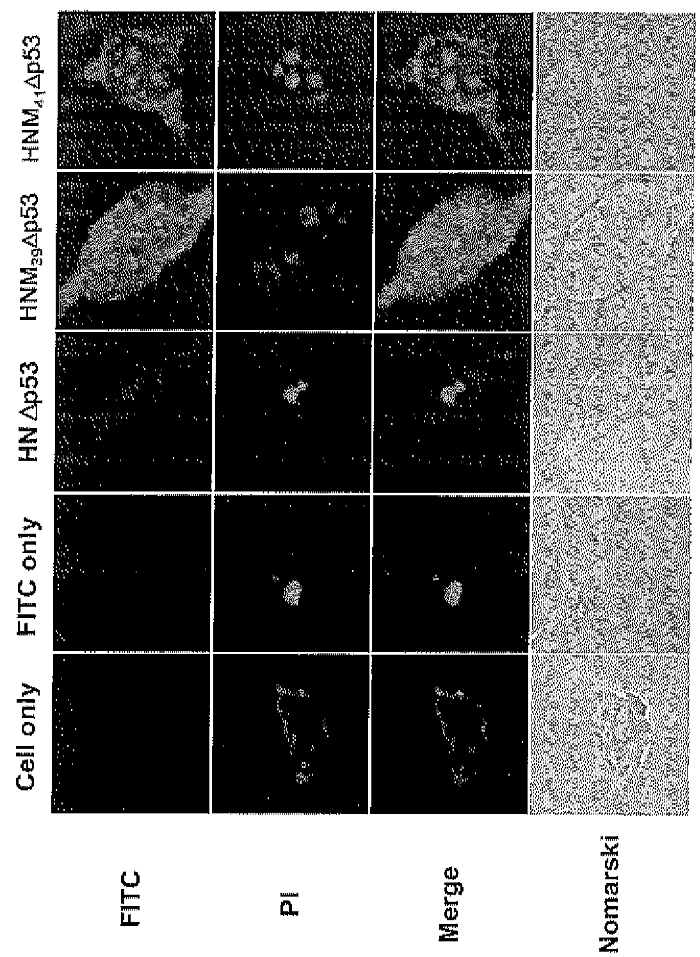
FIG. 12 is of confocal laser scanning microscopy photographs visualizing the cell permeability of p53 recombinant proteins in which JO-39 MTD or JO-41 MTD is fused, together with a nuclear localization sequence (NLS), to truncated p53.

As shown in FIG. 12, it was understood that the FITC-conjugated cell permeable Δp53 recombinant proteins according to the present invention were clearly localized within the cell nucleus, as compared with the cell only, FITC only, and the control devoid of MTD (HNΔp53). The nuclear localization of the cell-permeable Δp53 recombinant proteins constructed with JO-39 MTD and JO-41 MTD was consistent with the relative cell permeability determined above by flow cytometry.

Example 8

In Vitro Functionality of Cell-Permeable p53 Recombinant Protein

To evaluate the functionality of the cell-permeable recombinant p53 proteins, western blot analysis was carried out with a cancer cell line as follows. The colorectal tumor cell line HCT-116 was purchased from the Korean Cell Line Bank (Seoul, Korea). The cells were cultured in RPMI-1640 medium (300 mg/L L-glutamine, 89.3% 25 mM HEPES and 25 mM $NaHCO_3$, 9.8% heat inactivated fetal bovine serum, 0.9% streptomycin and penicillin) and maintained in an incubator at 37° C. in a 5% $CO_2$ incubator.

After 2 mL of RPMI 1640 medium supplemented with FBS was added to each well of 6-well plates, HCT-116 cells were plated at a density of $5\times10^6$ cells/ml into the plates and incubated at 37° C. for 1 day so as to allow the cells to grow as adherent monolayers. After aspiration of the medium, the cells adhering to the well plates were washed with cold PBS. Subsequently, the cells were treated with 500 μL of each of the cell permeable p53 recombinant proteins and MTD-devoid p53 control protein (Hp53), each protein having a concentration of 20 μM, and reacted in a 5% $CO_2$ incubator at 37° C. for 2 hours. Then, the cells were washed twice with PBS and cultured for 9 hours in the presence of serum under the same conditions as mentioned above.

After completion of the incubation, the cells were disrupted with 100 μL of a lysis buffer (20 mM HEPES, pH 7.2, 1% Triton-X, 10% glycerol and proteinase inhibitor) on ice for 30 min and the collected. The cell lysate thus obtained was heated at 100° C. for 10 min after which the recombinant protein was added at a concentration of 25 μM to an SDS-PAGE loading buffer to give a cell lysate sample which was then stored at −20° C. until use.

For western blot analysis, p21Waf1/Cip1 (21 kDa, Cell Signaling Technology) was used as a primary antibody while the secondary antibody was goat anti-mouse IgG-HRP (Santa Cruz Biotechnology). The quantified cell lysate sample was run on a SDS-PAGE gel at 100 V for 1.5 hours and then transferred for 1.5 hours onto a polyvinylidene fluoride (PDVF) membrane in the presence of 100 V. In order to block the nonspecific interaction between the blotted proteins and antibodies, the PVDF membrane was incubated for 1 hour with 5% non-fat dry milk in TBS/T buffer (10 mM Tris-Cl, pH 8.0, 150 mM NaCl, 0.05% Tween 20). The blocking buffer was removed, and the membrane was incubated overnight at 4° C. with the primary antibody. Then, the membrane was rinsed five times with TBS/T and incubated at room temperature for 1 hour with the secondary antibody. The membrane was again washed five times with TBS/T and the protein-antibody conjugates were detected and analyzed using enhanced chemiluminescence (ECL, GE Healthcare Amersham UK).

Figure 13:
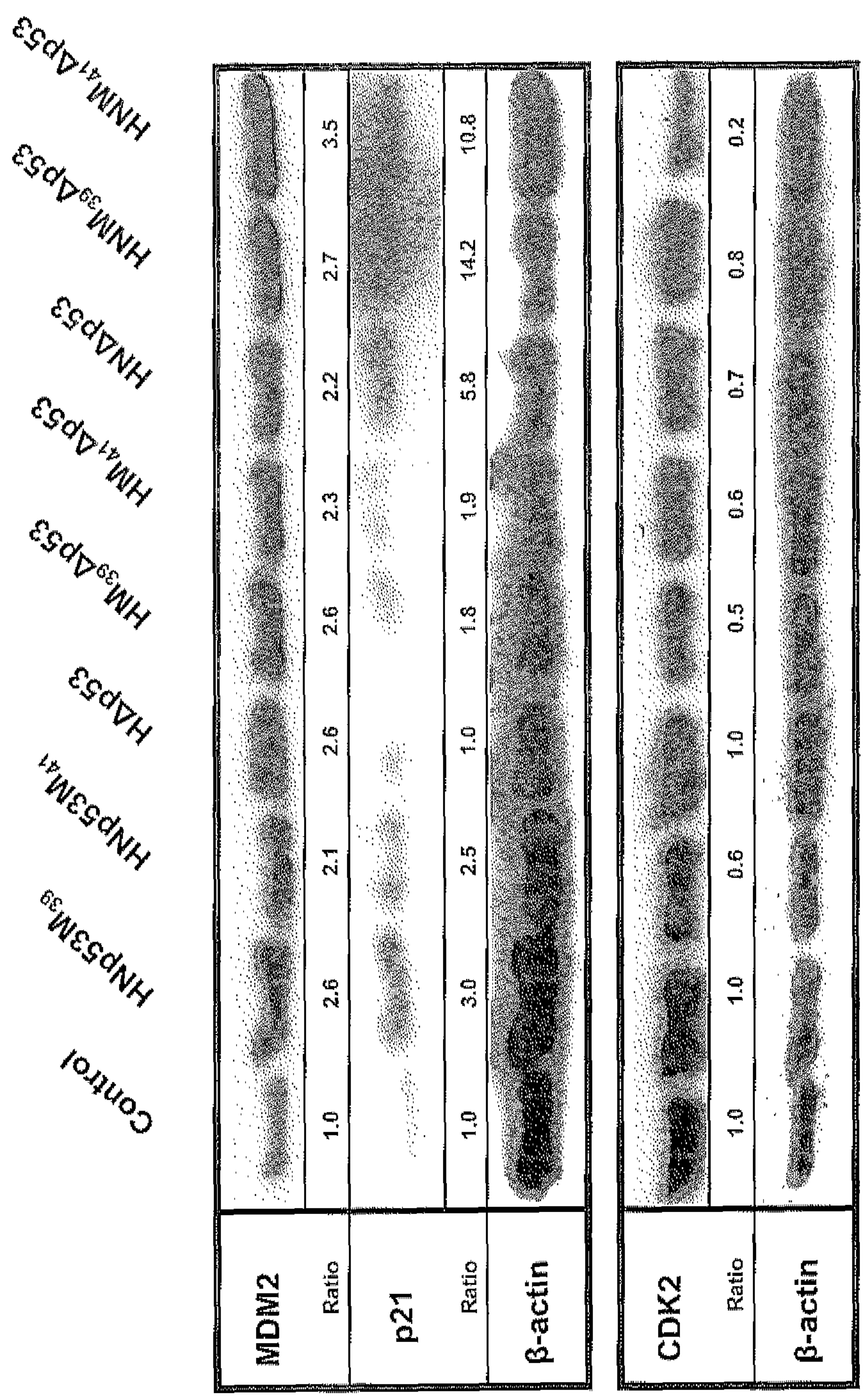
FIG. 13 is of photographs showing the in vitro activity of the cell-permeable truncated p53 recombinant proteins of the present invention as analyzed by Western blotting for the expression pattern of p21 in the human colorectal tumor cell line HCT-116.

As can be seen in FIG. 13, p53 increased the level of p21, which is responsible for cell cycle arrest. $HNM_{39}\Delta p53$ and $HNM_{41}\Delta p53$, constructed respectively with JO-39 MTD and JO-41 MTD, together with NLS, were observed to strongly halt the cell cycle of the cancer cells. Particularly, $HNM_{41}\Delta p53$ inhibited the activity of CDK2 in the cancer cell line, thus revealing its anticancer activity.

Example 9

In Vivo Functionality of Cell-Permeable p53 Recombinant Protein

In order to examine the in vivo functionality thereof, the cell permeable p53 recombinant proteins on tumor metastasis was assayed for anticancer activity in an animal model, as follows.

Figure 14:
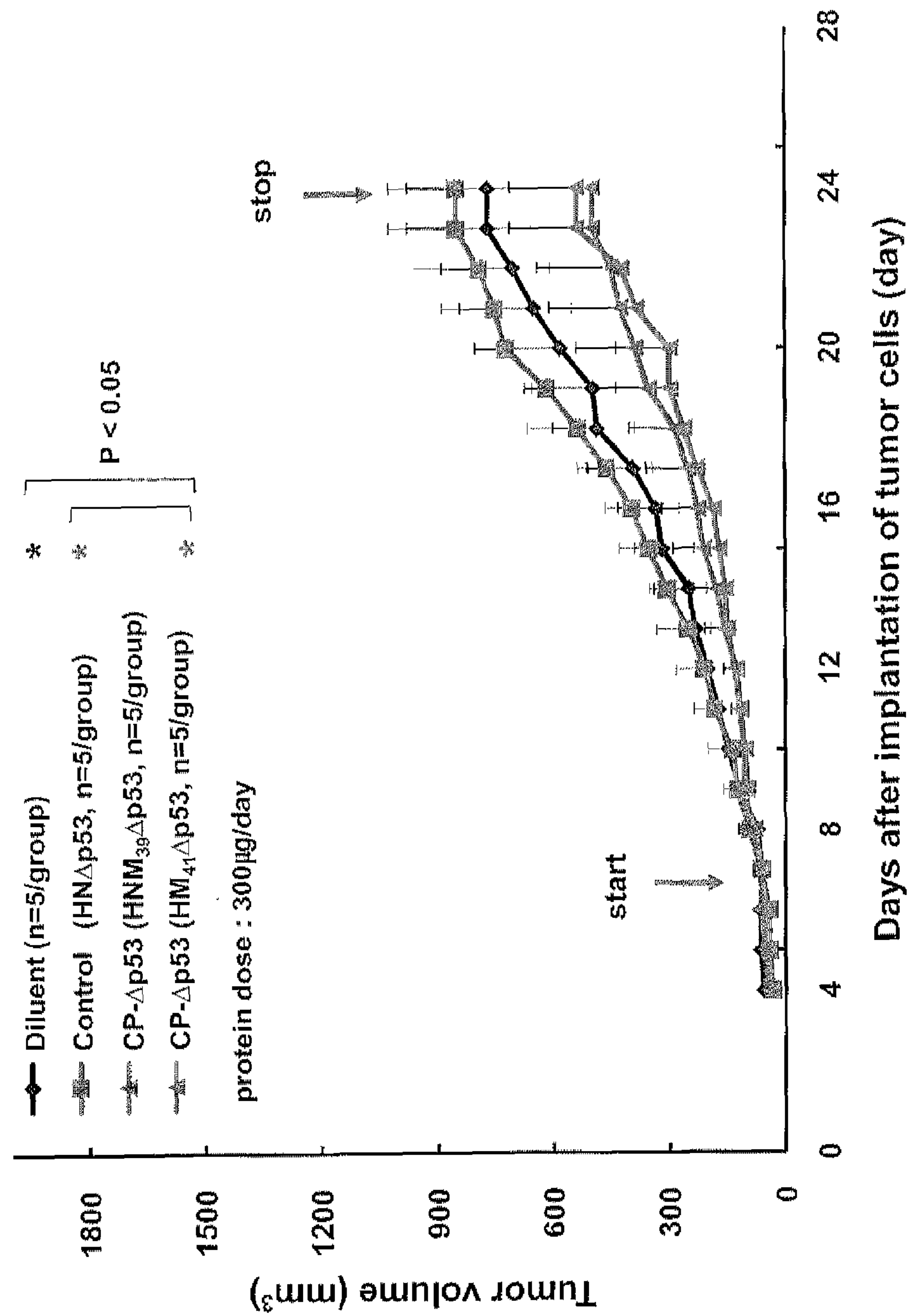
FIG. 14 is a graph in which tumor sizes of mice with tumors are plotted against time while they are intradermally injected with the truncated p53 recombinant proteins of the present invention every day for 17 days.

In this experiment, 7-week-old nude mice (Balb/c nu/nu mice, Central Lab Animal Inc. Seoul) deficient in immunity due to mutant MHC (major histocompatibility complex) was used as animal models. A suspension of HCT-116 cells (Korean Cell Line Bank) at a concentration of $1\times10^7$ cells/mL was subcutaneously injected into the right leg of the animal model using a syringe (omnican, Germany, B. BRAUN). From the day when tumors reached about 50~60 $mm^3$ ($width^2 \times length/2$) as measured using a vernier caliper, 1 μg/μL of each of the cell-permeable p53 recombinant proteins $HNM_{39}\Delta p53$ (n=5 mice/group) and $HM_{41}\Delta p53$ (n=5 mice/group) was intradermally injected at a daily dose of 300 μg for 17 days. As a control, vehicle (RPMI 1640, Group 1) or MTD-devoid HNΔp53 (n=5 mice/group) was intradermally injected at a daily dose of 300 μL for 17 days. After treatment with the proteins, tumor size was monitored every day, and the results are depicted in FIG. 14. Also, FIG. 15 shows photographs of the tumors.

As can be seen in FIG. 14, the tumor size of the groups treated with the cell-permeable p53 recombinant protein $HNM_{39}\Delta p53$ (n=5 mice/group) and $HM_{41}\Delta p53$ (n=5 mice/group) were significantly recessed, compared to that of the control groups (5 mice/group), with no significant change of weight in either of the control group and the cell-permeable p53 recombinant protein-treated groups. Specifically, $HNM_{39}\Delta p53$ and $HM_{41}\Delta p53$ showed effects of inhibiting tumor growth 40% and 42%, respectively, compared to that of the control groups.

Figure 15:
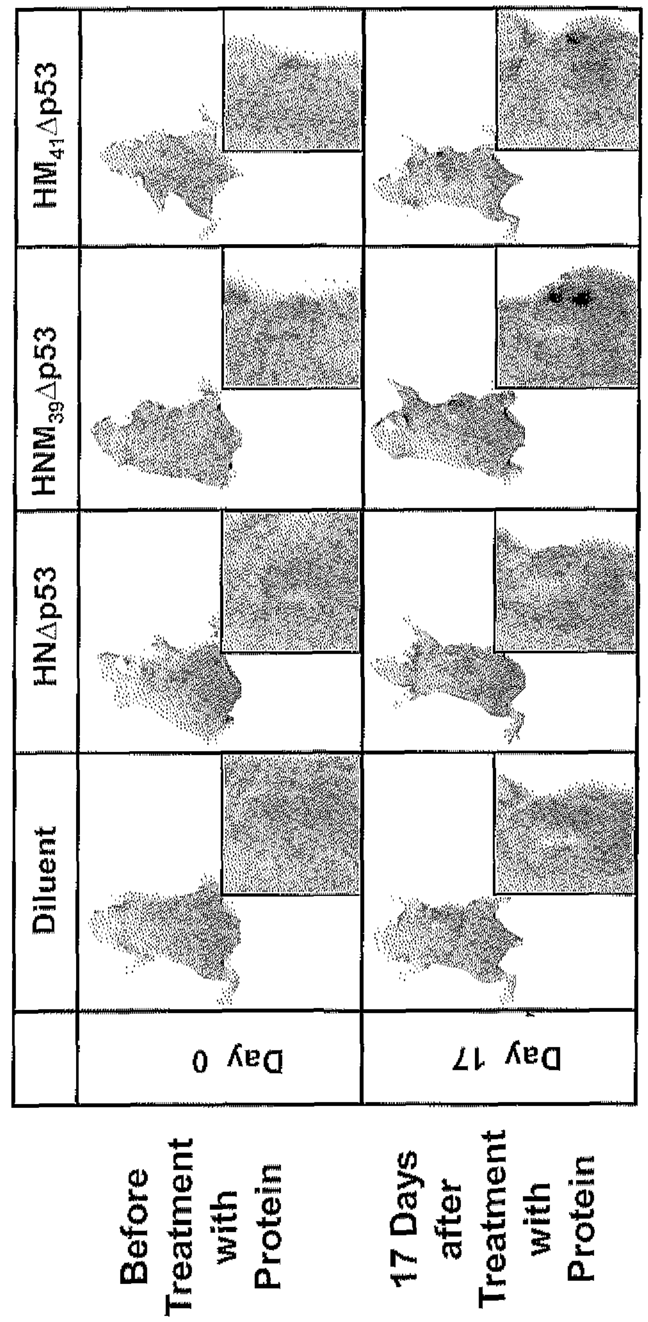
FIG. 15 is of photographs showing tumor sizes before and after the intradermal injection of the truncated p53 recombinant proteins of the present invention every day for 17 days.

During treatment, as shown in FIG. 15, tumor growth for both the $HNM_{39}\Delta p53$- and the $HM_{41}\Delta p53$-treated groups was significantly low, compared to the other group. These results demonstrate that the cell-permeable p53 recombinant proteins $HNM_{39}\Delta p53$ and $HM_{41}\Delta p53$ effectively work with stability.

With high cell permeability, the p53 recombinant protein of the present invention is effectively transduced into cells so that the tumor suppressor p53 can be translocated into cell nuclei. Within nuclei, p53 inhibits the formation of cyclin-CDK complexes to halt the cell cycle, thus suppressing excessive cell proliferation and inducing apoptosis of tumor cells. Therefore, the p53 recombinant protein of the present invention can be useful as an anticancer agent in the treatment of various cancers.

Although the invention has been described in detail for the sake of illustration, it is understood that such detail is provided solely for that purpose, and variations can be made therein by those skilled in the art without departing from the spirit and scope of the invention which is defined by the following claims.

What is claimed is:

1. A cell-permeable p53 recombinant protein, comprising a macromolecule transduction domain (MTD) and a p53 protein, said MTD having an amino acid sequence of SEQ ID NO: 6 or 8 and being fused to either or both termini of the p53 protein having an amino acid sequence of SEQ ID NO: 2.

2. The cell-permeable p53 recombinant protein of claim 1, wherein said MTD is selected from the group consisting of JO-39 MTD having an amino acid sequence of SEQ ID NO: 6 and JO-41 MTD having an amino acid sequence of SEQ ID NO: 8.

3. The cell-permeable p53 recombinant protein of claim 1, further comprising a nuclear localization sequence (NLS) and/or a histidine-tag affinity domain, wherein either or both said NLS and said histidine-tag affinity domains being fused to one end of the recombinant protein.

4. The cell-permeable p53 recombinant protein of claim 1, being selected from the group consisting of:

a recombinant protein wherein JO-39 MTD having an amino acid sequence of SEQ ID NO: 6 is fused to an N-terminus of a full-length p53 having an amino acid sequence of SEQ ID NO: 2;

a recombinant protein wherein JO-39 MTD having an amino acid sequence of SEQ ID NO: 6 is fused to a C-terminus of a full-length p53 having an amino acid sequence of SEQ ID NO: 2;

a recombinant protein wherein JO-39 MTD having an amino acid sequence of SEQ ID NO: 6 is fused to both termini of a full-length p53 having an amino acid sequence of SEQ ID NO: 2;

a recombinant protein wherein JO-41 MTD having an amino acid sequence of SEQ ID NO:8 is fused to an N-terminus of a full-length p53 having an amino acid sequence of SEQ ID NO: 2 a recombinant protein wherein JO-41 MTD having an amino acid sequence of SEQ ID NO:8 is fused to a C-terminus of a full-length p53 having an amino acid sequence of SEQ ID NO: 2; and a recombinant protein wherein JO-41 MTD having an amino acid sequence of SEQ ID NO: 8 is fused to both termini of a full-length p53 having an amino acid sequence of SEQ ID NO: 2.

5. The cell-permeable p53 recombinant protein of claim 1, wherein the recombinant protein has an amino acid sequence selected from the group consisting of SEQ ID NOS: 14, 16, 18, 20, 22 and 24.

6. The cell-permeable p53 recombinant protein of claim 1, wherein the recombinant protein has an amino acid sequence selected from the group consisting of SEQ ID NOS: 48, 50, 52, 54, 56 and 58.

7. A polynucleotide, encoding the cell-permeable p53 recombinant protein of claim 1.

8. The polynucleotide of claim 7, having a nucleotide sequence selected from the group consisting of SEQ ID NO: 13, 15, 17, 19, 21 and 23.

9. The polynucleotide of claim 7, having a nucleotide sequence selected from the group consisting of SEQ ID NO: 47, 49, 51, 53, 55 and 57.

10. A recombinant expression vector, carrying the polynucleotide of claim 7.

11. The recombinant expression vector of claim 10, being selected from the group consisting of pET28a(+)-$HNM_{39}$p53, pET28a(+)-$HNM_{41}$p53, pET28a(+)-HNp53 $M_{39}$, pET28a(+)-HNp53 $M_{41}$, pET28a(+)-$HNM_{39}$p53 $M_{39}$ and pET28a(+)-$HNM_{41}$p53 $M_{41}$.

12. A microorganism, transformed with the recombinant expression vector of claim 10.

13. A method for producing the cell-permeable p53 recombinant protein of claim 1, comprising 1) transforming a microorganism with a recombinant vector carrying the polynucleotide encoding the cell-permeable p53 recombinant protein of claim 1 to form a transformed microorganism;

2) culturing the transformed microorganism obtained from step (1) in a medium to express the cell-permeable p53 recombinant protein; and 3) harvesting the expressed cell-permeable p53 recombinant protein obtained from step (2) from the culture medium to obtain the cell-permeable p53 recombinant protein of claim 1.

14. A pharmaceutical composition for treatment of cancer caused by p53 deficiency or loss of p53 function, comprising the p53 recombinant protein of claim 1 as an active ingredient, and a pharmaceutically acceptable vehicle.

15. A cell-permeable p53 recombinant protein, comprising a macromolecule transduction domain (MTD) and a truncated p53 protein, said MTD having an amino acid sequence of SEQ ID NO: 6 or 8 and being fused to either or both termini of the truncated p53 protein having an amino acid sequence of SEQ ID NO: 4.

16. The cell-permeable p53 recombinant protein of claim 15, wherein said MTD is selected from the group consisting of JO-39 MTD having an amino acid sequence of SEQ ID NO: 6 and JO-41 MTD having an amino acid sequence of SEQ ID NO: 8.

17. The cell-permeable p53 recombinant protein of claim 15, further comprising a nuclear localization sequence (NLS) and/or a histidine-tag affinity domain, wherein either or both said NLS and said histidine-tag affinity domains being fused to one end of the recombinant protein.

18. The cell-permeable p53 recombinant protein of claim 15, being selected from the group consisting of:

a recombinant protein wherein JO-39 MTD having an amino acid sequence of SEQ ID NO: 6 is fused to an N-terminus of a truncated p53 having an amino acid sequence of SEQ ID NO: 4;

a recombinant protein wherein JO-39 MTD having an amino acid sequence of SEQ ID NO: 6 is fused to a C-terminus of a truncated p53 having an amino acid sequence of SEQ ID NO: 4;

a recombinant protein wherein J0-41 MTD having an amino acid sequence of SEQ ID NO: 8 is fused to an N-terminus of a truncated p53 having an amino acid sequence of SEQ ID NO: 4; and a recombinant protein wherein J0-41 MTD having an amino acid sequence of SEQ ID NO: 8 is fused to a C-terminus of a truncated p53 having an amino acid sequence of SEQ ID NO: 4.

19. The cell-permeable p53 recombinant protein of claim 1, wherein the recombinant protein has an amino acid sequence selected from the group consisting of SEQ ID NOS: 28, 30, 32, 34, 38, 40, 42 and 44.

20. The cell-permeable p53 recombinant protein of claim 1, wherein the recombinant protein has an amino acid sequence selected from the group consisting of SEQ ID NOS: 64, 66, 68, 70, 72, 74, 76 and 78.

21. A polynucleotide, encoding the cell-permeable p53 recombinant protein of claim 15.

22. The polynucleotide of claim 21, having a nucleotide sequence selected from the group consisting of SEQ ID NOS: 27, 29, 31, 33, 37, 39, 41 and 43.

23. The polynucleotide of claim 21, having a nucleotide sequence selected from the group consisting of SEQ ID NOS: 63, 65, 67, 69, 71, 73, 75 and 77.

24. A recombinant expression vector, carrying the polynucleotide of claim 21.

25. The recombinant expression vector of claim 24, being selected from the group consisting of pET28a(+)-$HNM_{39}\Delta p53$, pET28a(+)-$HNM_{41}\Delta p53$, pET28a(+)-$HM_{39}\Delta p53$, and pET28a(+)-$HM_{41}\Delta p53$.

26. A microorganism, transformed with the recombinant expression vector of claim 24.

27. The microorganism of claim 26, being *E. coli* DH5α/$HNM_{39}\Delta p53$ (accession No: KCTC 11596BP).

28. The microorganism of claim 26, being *E. coli* DH5α/$HM_{39}\Delta p53$ (accession No: KCTC 11595BP).

29. A method for producing the cell-permeable p53 recombinant protein of claim 15, comprising 1) transforming a microorganism with a recombinant vector carrying the polynucleotide encoding the cell-permeable p53 recombinant protein of claim 15 to form a transformed microorganism;
2) culturing the transformed microorganism obtained from step (1) in a medium to express the cell-permeable p53 recombinant protein; and
3) harvesting the expressed cell-permeable p53 recombinant protein obtained from step (2) from the culture medium to obtain the cell-permeable p53 recombinant protein of claim 15.

30. A pharmaceutical composition for treatment of cancer caused by p53 deficiency or loss of p53 function, comprising the p53 recombinant protein of claim 15 as an active ingredient, and a pharmaceutically acceptable vehicle.

* * * * *

UNITED STATES PATENT AND TRADEMARK OFFICE

CERTIFICATE OF CORRECTION

PATENT NO. : 8,470,971 B2
APPLICATION NO. : 13/132202
DATED : June 25, 2013
INVENTOR(S) : Jo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 271 days.

Signed and Sealed this
Eighth Day of September, 2015

Michelle K. Lee

Michelle K. Lee
*Director of the United States Patent and Trademark Office*

SEQUENCE LISTING

```
<160> NUMBER OF SEQ ID NOS: 90

<210> SEQ ID NO 1
<211> LENGTH: 1182
<212> TYPE: DNA
<213> ORGANISM: Homo Sapiens
<220> FEATURE:
<223> OTHER INFORMATION: Human p53 cDNA Sequence

<400> SEQUENCE: 1

atggaggagc cgcagtcaga tcctagcgtc gagccccctc tgagtcagga aacattttca      60

gacctatgga aactacttcc tgaaaacaac gttctgtccc ccttgccgtc ccaagcaatg     120

gatgatttga tgctgtcccc ggacgatatt gaacaatggt tcactgaaga cccaggtcca     180

gatgaagctc ccagaatgcc agaggctgct ccccgcgtgg cccctgcacc agcagctcct     240

acaccggcgg cccctgcacc agccccctcc tggcccctgt catcttctgt cccttcccag     300

aaaacctacc agggcagcta cggtttccgt ctgggcttct tgcattctgg gacagccaag     360

tctgtgactt gcacgtactc ccctgccctc aacaagatgt tttgccaact ggccaagacc     420

tgccctgtgc agctgtgggt tgattccaca cccccgcccg gcacccgcgt ccgcgccatg     480

gccatctaca agcagtcaca gcacatgacg gaggttgtga ggcgctgccc ccaccatgag     540

cgctgctcag atagcgatgg tctggcccct cctcagcatc ttatccgagt ggaaggaaat     600

ttgcgtgtgg agtatttgga tgacagaaac acttttcgac atagtgtggt ggtgccctat     660

gagccgcctg aggttggctc tgactgtacc accatccact acaactacat gtgtaacagt     720

tcctgcatgg gcggcatgaa ccggaggccc atcctcacca tcatcacact ggaagactcc     780

agtggtaatc tactgggacg gaacagcttt gaggtgcgtg tttgtgcctg tcctgggaga     840

gaccggcgca cagaggaaga gaatctccgc aagaaagggg agcctcacca cgagctgccc     900

ccagggagca ctaagcgagc actgcccaac aacaccagct cctctcccca gccaaagaag     960

aaaccactgg atggaggata tttcaccctt cagatccgtg ggcgtgagcg cttcgagatg    1020

ttccgagagc tgattgaggc cttggaactc aaggatgccc aggctgggaa ggagccaggg    1080

gggagcaggg ctcactccag ccacctgaag tccaaaaagg gtcagtctac ctcccgccat    1140
```

```
aaaaaactca tgttcaagac agaagggcct gactcagact ga                    1182


<210> SEQ ID NO 2
<211> LENGTH: 393
<212> TYPE: PRT
<213> ORGANISM: Homo Sapiens
<220> FEATURE:
<223> OTHER INFORMATION: Human P53 Amino Acid Sequence

<400> SEQUENCE: 2

Met Glu Glu Pro Gln Ser Asp Pro Ser Val Glu Pro Pro Leu Ser Gln
  1               5                  10                  15

Glu Thr Phe Ser Asp Leu Trp Lys Leu Leu Pro Glu Asn Asn Val Leu
             20                  25                  30

Ser Pro Leu Pro Ser Gln Ala Met Asp Asp Leu Met Leu Ser Pro Asp
         35                  40                  45

Asp Ile Glu Gln Trp Phe Thr Glu Asp Pro Gly Pro Asp Glu Ala Pro
     50                  55                  60

Arg Met Pro Glu Ala Ala Pro Arg Val Ala Pro Ala Pro Ala Ala Pro
 65                  70                  75                  80

Thr Pro Ala Ala Pro Ala Pro Ala Pro Ser Trp Pro Leu Ser Ser Ser
                 85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Gly Tyr Phe Thr Leu Gln Ile Arg Gly Arg Glu
                325                 330                 335

Arg Phe Glu Met Phe Arg Glu Leu Ile Glu Ala Leu Glu Leu Lys Asp
            340                 345                 350

Ala Gln Ala Gly Lys Glu Pro Gly Gly Ser Arg Ala His Ser Ser His
        355                 360                 365
```

```
Leu Lys Ser Lys Lys Gly Gln Ser Thr Ser Arg His Lys Lys Leu Met
    370                 375                 380

Phe Lys Thr Glu Gly Pro Asp Ser Asp
385                 390


<210> SEQ ID NO 3
<211> LENGTH: 306
<212> TYPE: DNA
<213> ORGANISM: Artificial Sequence
<220> FEATURE:
<223> OTHER INFORMATION: Human deltap53 cDNA Sequence

<400> SEQUENCE: 3

atggaggagc cgcagtcaga tcctagcgtc gagccccctc tgagtcagga aacattttca      60

gacctatgga aactacttcc tgaaaacaac gttctgtccc ccttgccgtc ccaagcaatg     120

gatgatttga tgctgtcccc ggacgatatt gaacaatggt tcactgaaga cccaggtcca     180

gatgaagctc ccagaatgcc agaggctgct ccccgcgtgg cccctgcacc agcagctcct     240

acaccggcgg cccctgcacc agccccctcc tggcccctgt catcttctgt cccttcccag     300

aaaacc                                                                306


<210> SEQ ID NO 4
<211> LENGTH: 102
<212> TYPE: PRT
<213> ORGANISM: Artificial Sequence
<220> FEATURE:
<223> OTHER INFORMATION: Human deltap53 Amino Sequence

<400> SEQUENCE: 4

Met Glu Glu Pro Gln Ser Asp Pro Ser Val Glu Pro Pro Leu Ser Gln
  1               5                  10                  15

Glu Thr Phe Ser Asp Leu Trp Lys Leu Leu Pro Glu Asn Asn Val Leu
             20                  25                  30

Ser Pro Leu Pro Ser Gln Ala Met Asp Asp Leu Met Leu Ser Pro Asp
         35                  40                  45

Asp Ile Glu Gln Trp Phe Thr Glu Asp Pro Gly Pro Asp Glu Ala Pro
     50                  55                  60

Arg Met Pro Glu Ala Ala Pro Arg Val Ala Pro Ala Pro Ala Ala Pro
 65                  70                  75                  80

Thr Pro Ala Ala Pro Ala Pro Ala Pro Ser Trp Pro Leu Ser Ser Ser
                 85                  90                  95

Val Pro Ser Gln Lys Thr
            100


<210> SEQ ID NO 5
<211> LENGTH: 30
<212> TYPE: DNA
<213> ORGANISM: Artificial Sequence
<220> FEATURE:
<223> OTHER INFORMATION: JO-39 MTD cDNA Sequence

<400> SEQUENCE: 5

ccgctggtgc tggcgattgc ggcggtgctg                                       30


<210> SEQ ID NO 6
<211> LENGTH: 10
<212> TYPE: PRT
<213> ORGANISM: Artificial Sequence
<220> FEATURE:
<223> OTHER INFORMATION: JO-39 MTD Amino Acid Sequence
```

<400> SEQUENCE: 6

```
Pro Leu Val Leu Ala Ile Ala Ala Val Leu
1               5                   10
```

<210> SEQ ID NO 7
<211> LENGTH: 24
<212> TYPE: DNA
<213> ORGANISM: Artificial Sequence
<220> FEATURE:
<223> OTHER INFORMATION: JO-41 MTD cDNA Sequence

<400> SEQUENCE: 7

```
gcggcggcgc tgctggcggt ggcg                                            24
```

<210> SEQ ID NO 8
<211> LENGTH: 8
<212> TYPE: PRT
<213> ORGANISM: Artificial Sequence
<220> FEATURE:
<223> OTHER INFORMATION: JO-41 MTD Amino Acid Sequence

<400> SEQUENCE: 8

```
Ala Ala Ala Leu Leu Ala Val Ala
1               5
```

<210> SEQ ID NO 9
<211> LENGTH: 15
<212> TYPE: DNA
<213> ORGANISM: Artificial Sequence
<220> FEATURE:
<223> OTHER INFORMATION: SV40 large T antigen-derived NLS cDNA Sequence

<400> SEQUENCE: 9

```
aagaagaaga ggaag                                                      15
```

<210> SEQ ID NO 10
<211> LENGTH: 5
<212> TYPE: PRT
<213> ORGANISM: Artificial Sequence
<220> FEATURE:
<223> OTHER INFORMATION: SV40 large T antigen-derived NLS Amino Acid Sequence

<400> SEQUENCE: 10

```
Lys Lys Lys Arg Lys
  1               5
```

<210> SEQ ID NO 11
<211> LENGTH: 1197
<212> TYPE: DNA
<213> ORGANISM: Artificial Sequence
<220> FEATURE:
<223> OTHER INFORMATION: NLS-p53 cDNA Sequence

<400> SEQUENCE: 11

```
atgaagaaga agaggaagga ggagccgcag tcagatccta gcgtcgagcc ccctctgagt     60

caggaaacat tttcagacct atggaaacta cttcctgaaa acaacgttct gtcccccttg    120

ccgtcccaag caatggatga tttgatgctg tccccggacg atattgaaca atggttcact    180

gaagacccag gtccagatga agctcccaga atgccagagg ctgctccccg cgtggcccct    240

gcaccagcag ctcctacacc ggcggcccct gcaccagccc cctcctggcc cctgtcatct    300

tctgtccctt cccagaaaac ctaccagggc agctacggtt tccgtctggg cttcttgcat    360

tctgggacag ccaagtctgt gacttgcacg tactcccctg ccctcaacaa gatgttttgc    420
```

```
caactggcca agacctgccc tgtgcagctg tgggttgatt ccacaccccc gcccggcacc    480

cgcgtccgcg ccatggccat ctacaagcag tcacagcaca tgacggaggt tgtgaggcgc    540

tgcccccacc atgagcgctg ctcagatagc gatggtctgg cccctcctca gcatcttatc    600

cgagtggaag gaaatttgcg tgtggagtat ttggatgaca gaaacacttt tcgacatagt    660

gtggtggtgc cctatgagcc gcctgaggtt ggctctgact gtaccaccat ccactacaac    720

tacatgtgta acagttcctg catgggcggc atgaaccgga ggcccatcct caccatcatc    780

acactggaag actccagtgg taatctactg ggacggaaca gctttgaggt gcgtgtttgt    840

gcctgtcctg ggagagaccg gcgcacagag gaagagaatc tccgcaagaa aggggagcct    900

caccacgagc tgcccccagg gagcactaag cgagcactgc ccaacaacac cagctcctct    960

ccccagccaa agaagaaacc actggatgga ggatatttca cccttcagat ccgtgggcgt   1020

gagcgcttcg agatgttccg agagctgatt gaggccttgg aactcaagga tgcccaggct   1080

gggaaggagc cagggggggag cagggctcac tccagccacc tgaagtccaa aaagggtcag   1140

tctacctccc gccataaaaa actcatgttc aagacagaag ggcctgactc agactga      1197
```

```
<210> SEQ ID NO 12
<211> LENGTH: 398
<212> TYPE: PRT
<213> ORGANISM: Artificial Sequence
<220> FEATURE:
<223> OTHER INFORMATION: NLS-p53 Amino Acid Sequence

<400> SEQUENCE: 12

Met Lys Lys Lys Arg Lys Glu Glu Pro Gln Ser Asp Pro Ser Val Glu
  1               5                  10                  15

Pro Pro Leu Ser Gln Glu Thr Phe Ser Asp Leu Trp Lys Leu Leu Pro
             20                  25                  30

Glu Asn Asn Val Leu Ser Pro Leu Pro Ser Gln Ala Met Asp Asp Leu
         35                  40                  45

Met Leu Ser Pro Asp Asp Ile Glu Gln Trp Phe Thr Glu Asp Pro Gly
     50                  55                  60

Pro Asp Glu Ala Pro Arg Met Pro Glu Ala Ala Pro Arg Val Ala Pro
 65                  70                  75                  80

Ala Pro Ala Ala Pro Thr Pro Ala Ala Pro Ala Pro Ala Pro Ser Trp
                 85                  90                  95

Pro Leu Ser Ser Ser Val Pro Ser Gln Lys Thr Tyr Gln Gly Ser Tyr
            100                 105                 110

Gly Phe Arg Leu Gly Phe Leu His Ser Gly Thr Ala Lys Ser Val Thr
        115                 120                 125

Cys Thr Tyr Ser Pro Ala Leu Asn Lys Met Phe Cys Gln Leu Ala Lys
    130                 135                 140

Thr Cys Pro Val Gln Leu Trp Val Asp Ser Thr Pro Pro Pro Gly Thr
145                 150                 155                 160

Arg Val Arg Ala Met Ala Ile Tyr Lys Gln Ser Gln His Met Thr Glu
                165                 170                 175

Val Val Arg Arg Cys Pro His His Glu Arg Cys Ser Asp Ser Asp Gly
            180                 185                 190

Leu Ala Pro Pro Gln His Leu Ile Arg Val Glu Gly Asn Leu Arg Val
        195                 200                 205

Glu Tyr Leu Asp Asp Arg Asn Thr Phe Arg His Ser Val Val Val Pro
    210                 215                 220

Tyr Glu Pro Pro Glu Val Gly Ser Asp Cys Thr Thr Ile His Tyr Asn
225                 230                 235                 240
```

```
Tyr Met Cys Asn Ser Ser Cys Met Gly Gly Met Asn Arg Arg Pro Ile
                245                 250                 255

Leu Thr Ile Ile Thr Leu Glu Asp Ser Ser Gly Asn Leu Leu Gly Arg
            260                 265                 270

Asn Ser Phe Glu Val Arg Val Cys Ala Cys Pro Gly Arg Asp Arg Arg
        275                 280                 285

Thr Glu Glu Glu Asn Leu Arg Lys Lys Gly Glu Pro His His Glu Leu
    290                 295                 300

Pro Pro Gly Ser Thr Lys Arg Ala Leu Pro Asn Asn Thr Ser Ser Ser
305                 310                 315                 320

Pro Gln Pro Lys Lys Lys Pro Leu Asp Gly Gly Tyr Phe Thr Leu Gln
                325                 330                 335

Ile Arg Gly Arg Glu Arg Phe Glu Met Phe Arg Glu Leu Ile Glu Ala
            340                 345                 350

Leu Glu Leu Lys Asp Ala Gln Ala Gly Lys Glu Pro Gly Gly Ser Arg
        355                 360                 365

Ala His Ser Ser His Leu Lys Ser Lys Lys Gly Gln Ser Thr Ser Arg
    370                 375                 380

His Lys Lys Leu Met Phe Lys Thr Glu Gly Pro Asp Ser Asp
385                 390                 395


<210> SEQ ID NO 13
<211> LENGTH: 1227
<212> TYPE: DNA
<213> ORGANISM: Artificial Sequence
<220> FEATURE:
<223> OTHER INFORMATION: NLS-JO-39 MTD-p53 cDNA Sequence

<400> SEQUENCE: 13

atgaagaaga agaggaagcc gctggtgctg gcgattgcgg cggtgctgga ggagccgcag     60

tcagatccta gcgtcgagcc ccctctgagt caggaaacat tttcagacct atggaaacta    120

cttcctgaaa acaacgttct gtcccccttg ccgtcccaag caatggatga tttgatgctg    180

tccccggacg atattgaaca atggttcact gaagacccag gtccagatga agctcccaga    240

atgccagagg ctgctccccg cgtggcccct gcaccagcag ctcctacacc ggcggcccct    300

gcaccagccc cctcctggcc cctgtcatct tctgtccctt cccagaaaac ctaccagggc    360

agctacggtt tccgtctggg cttcttgcat tctgggacag ccaagtctgt gacttgcacg    420

tactcccctg ccctcaacaa gatgttttgc caactggcca agacctgccc tgtgcagctg    480

tgggttgatt ccacaccccc gcccggcacc cgcgtccgcg ccatggccat ctacaagcag    540

tcacagcaca tgacggaggt tgtgaggcgc tgcccccacc atgagcgctg ctcagatagc    600

gatggtctgg cccctcctca gcatcttatc cgagtggaag gaaatttgcg tgtggagtat    660

ttggatgaca gaaacacttt tcgacatagt gtggtggtgc cctatgagcc gcctgaggtt    720

ggctctgact gtaccaccat ccactacaac tacatgtgta acagttcctg catgggcggc    780

atgaaccgga ggcccatcct caccatcatc acactggaag actccagtgg taatctactg    840

ggacggaaca gctttgaggt gcgtgtttgt gcctgtcctg ggagagaccg gcgcacagag    900

gaagagaatc tccgcaagaa aggggagcct caccacgagc tgcccccagg gagcactaag    960

cgagcactgc ccaacaacac cagctcctct ccccagccaa agaagaaacc actggatgga   1020

ggatatttca cccttcagat ccgtgggcgt gagcgcttcg agatgttccg agagctgatt   1080

gaggccttgg aactcaagga tgcccaggct gggaaggagc caggggggag cagggctcac   1140

tccagccacc tgaagtccaa aaagggtcag tctacctccc gccataaaaa actcatgttc   1200
```

```
aagacagaag ggcctgactc agactga                                         1227


<210> SEQ ID NO 14
<211> LENGTH: 408
<212> TYPE: PRT
<213> ORGANISM: Artificial Sequence
<220> FEATURE:
<223> OTHER INFORMATION: NLS-JO-39 MTD p53 Amino Acid Sequence

<400> SEQUENCE: 14

Met Lys Lys Lys Arg Lys Pro Leu Val Leu Ala Ile Ala Ala Val Leu
1               5                   10                  15

Glu Glu Pro Gln Ser Asp Pro Ser Val Glu Pro Pro Leu Ser Gln Glu
            20                  25                  30

Thr Phe Ser Asp Leu Trp Lys Leu Leu Pro Glu Asn Asn Val Leu Ser
        35                  40                  45

Pro Leu Pro Ser Gln Ala Met Asp Asp Leu Met Leu Ser Pro Asp Asp
    50                  55                  60

Ile Glu Gln Trp Phe Thr Glu Asp Pro Gly Pro Asp Glu Ala Pro Arg
65                  70                  75                  80

Met Pro Glu Ala Ala Pro Arg Val Ala Pro Ala Pro Ala Ala Pro Thr
                85                  90                  95

Pro Ala Ala Pro Ala Pro Ala Pro Ser Trp Pro Leu Ser Ser Ser Val
            100                 105                 110

Pro Ser Gln Lys Thr Tyr Gln Gly Ser Tyr Gly Phe Arg Leu Gly Phe
        115                 120                 125

Leu His Ser Gly Thr Ala Lys Ser Val Thr Cys Thr Tyr Ser Pro Ala
    130                 135                 140

Leu Asn Lys Met Phe Cys Gln Leu Ala Lys Thr Cys Pro Val Gln Leu
145                 150                 155                 160

Trp Val Asp Ser Thr Pro Pro Pro Gly Thr Arg Val Arg Ala Met Ala
                165                 170                 175

Ile Tyr Lys Gln Ser Gln His Met Thr Glu Val Val Arg Arg Cys Pro
            180                 185                 190

His His Glu Arg Cys Ser Asp Ser Asp Gly Leu Ala Pro Pro Gln His
        195                 200                 205

Leu Ile Arg Val Glu Gly Asn Leu Arg Val Glu Tyr Leu Asp Asp Arg
    210                 215                 220

Asn Thr Phe Arg His Ser Val Val Val Pro Tyr Glu Pro Pro Glu Val
225                 230                 235                 240

Gly Ser Asp Cys Thr Thr Ile His Tyr Asn Tyr Met Cys Asn Ser Ser
                245                 250                 255

Cys Met Gly Gly Met Asn Arg Arg Pro Ile Leu Thr Ile Ile Thr Leu
            260                 265                 270

Glu Asp Ser Ser Gly Asn Leu Leu Gly Arg Asn Ser Phe Glu Val Arg
        275                 280                 285

Val Cys Ala Cys Pro Gly Arg Asp Arg Arg Thr Glu Glu Glu Asn Leu
    290                 295                 300

Arg Lys Lys Gly Glu Pro His His Glu Leu Pro Pro Gly Ser Thr Lys
305                 310                 315                 320

Arg Ala Leu Pro Asn Asn Thr Ser Ser Ser Pro Gln Pro Lys Lys Lys
                325                 330                 335

Pro Leu Asp Gly Gly Tyr Phe Thr Leu Gln Ile Arg Gly Arg Glu Arg
            340                 345                 350

Phe Glu Met Phe Arg Glu Leu Ile Glu Ala Leu Glu Leu Lys Asp Ala
```

-continued

```
        355                 360                 365

Gln Ala Gly Lys Glu Pro Gly Gly Ser Arg Ala His Ser Ser His Leu
    370                 375                 380

Lys Ser Lys Lys Gly Gln Ser Thr Ser Arg His Lys Lys Leu Met Phe
385                 390                 395                 400

Lys Thr Glu Gly Pro Asp Ser Asp
                405


<210> SEQ ID NO 15
<211> LENGTH: 1227
<212> TYPE: DNA
<213> ORGANISM: Artificial Sequence
<220> FEATURE:
<223> OTHER INFORMATION: NLS-p53-JO-39 MTD cDNA Sequence

<400> SEQUENCE: 15

atgaagaaga agaggaagga ggagccgcag tcagatccta gcgtcgagcc ccctctgagt     60

caggaaacat tttcagacct atggaaacta cttcctgaaa acaacgttct gtcccccttg    120

ccgtcccaag caatggatga tttgatgctg tccccggacg atattgaaca atggttcact    180

gaagacccag gtccagatga agctcccaga atgccagagg ctgctccccg cgtggcccct    240

gcaccagcag ctcctacacc ggcggcccct gcaccagccc cctcctggcc cctgtcatct    300

tctgtccctt cccagaaaac ctaccagggc agctacggtt tccgtctggg cttcttgcat    360

tctgggacag ccaagtctgt gacttgcacg tactcccctg ccctcaacaa gatgttttgc    420

caactggcca agacctgccc tgtgcagctg tgggttgatt ccacaccccc gcccggcacc    480

cgcgtccgcg ccatggccat ctacaagcag tcacagcaca tgacggaggt tgtgaggcgc    540

tgcccccacc atgagcgctg ctcagatagc gatggtctgg cccctcctca gcatcttatc    600

cgagtggaag gaaatttgcg tgtggagtat ttggatgaca gaaacacttt tcgacatagt    660

gtggtggtgc cctatgagcc gcctgaggtt ggctctgact gtaccaccat ccactacaac    720

tacatgtgta acagttcctg catgggcggc atgaaccgga ggcccatcct caccatcatc    780

acactggaag actccagtgg taatctactg ggacggaaca gctttgaggt gcgtgtttgt    840

gcctgtcctg ggagagaccg gcgcacagag gaagagaatc tccgcaagaa aggggagcct    900

caccacgagc tgcccccagg gagcactaag cgagcactgc ccaacaacac cagctcctct    960

ccccagccaa agaagaaacc actggatgga ggatatttca cccttcagat ccgtgggcgt   1020

gagcgcttcg agatgttccg agagctgatt gaggccttgg aactcaagga tgcccaggct   1080

gggaaggagc caggggggag cagggctcac tccagccacc tgaagtccaa aaagggtcag   1140

tctacctccc gccataaaaa actcatgttc aagacagaag ggcctgactc agacccgctg   1200

gtgctggcga ttgcggcggt gctgtga                                        1227


<210> SEQ ID NO 16
<211> LENGTH: 408
<212> TYPE: PRT
<213> ORGANISM: Artificial Sequence
<220> FEATURE:
<223> OTHER INFORMATION: NLS p53-JO-39 MTD Amino Acid Sequence

<400> SEQUENCE: 16

Met Lys Lys Lys Arg Lys Glu Glu Pro Gln Ser Asp Pro Ser Val Glu
  1               5                  10                  15

Pro Pro Leu Ser Gln Glu Thr Phe Ser Asp Leu Trp Lys Leu Leu Pro
             20                  25                  30

Glu Asn Asn Val Leu Ser Pro Leu Pro Ser Gln Ala Met Asp Asp Leu
```

```
        35                  40                  45

Met Leu Ser Pro Asp Asp Ile Glu Gln Trp Phe Thr Glu Asp Pro Gly
    50                  55                  60

Pro Asp Glu Ala Pro Arg Met Pro Glu Ala Ala Pro Arg Val Ala Pro
65                  70                  75                  80

Ala Pro Ala Ala Pro Thr Pro Ala Ala Pro Ala Pro Ala Pro Ser Trp
                85                  90                  95

Pro Leu Ser Ser Ser Val Pro Ser Gln Lys Thr Tyr Gln Gly Ser Tyr
            100                 105                 110

Gly Phe Arg Leu Gly Phe Leu His Ser Gly Thr Ala Lys Ser Val Thr
        115                 120                 125

Cys Thr Tyr Ser Pro Ala Leu Asn Lys Met Phe Cys Gln Leu Ala Lys
    130                 135                 140

Thr Cys Pro Val Gln Leu Trp Val Asp Ser Thr Pro Pro Pro Gly Thr
145                 150                 155                 160

Arg Val Arg Ala Met Ala Ile Tyr Lys Gln Ser Gln His Met Thr Glu
                165                 170                 175

Val Val Arg Arg Cys Pro His His Glu Arg Cys Ser Asp Ser Asp Gly
            180                 185                 190

Leu Ala Pro Pro Gln His Leu Ile Arg Val Glu Gly Asn Leu Arg Val
        195                 200                 205

Glu Tyr Leu Asp Asp Arg Asn Thr Phe Arg His Ser Val Val Val Pro
    210                 215                 220

Tyr Glu Pro Pro Glu Val Gly Ser Asp Cys Thr Thr Ile His Tyr Asn
225                 230                 235                 240

Tyr Met Cys Asn Ser Ser Cys Met Gly Gly Met Asn Arg Arg Pro Ile
                245                 250                 255

Leu Thr Ile Ile Thr Leu Glu Asp Ser Ser Gly Asn Leu Leu Gly Arg
            260                 265                 270

Asn Ser Phe Glu Val Arg Val Cys Ala Cys Pro Gly Arg Asp Arg Arg
        275                 280                 285

Thr Glu Glu Glu Asn Leu Arg Lys Lys Gly Glu Pro His His Glu Leu
    290                 295                 300

Pro Pro Gly Ser Thr Lys Arg Ala Leu Pro Asn Asn Thr Ser Ser Ser
305                 310                 315                 320

Pro Gln Pro Lys Lys Lys Pro Leu Asp Gly Gly Tyr Phe Thr Leu Gln
                325                 330                 335

Ile Arg Gly Arg Glu Arg Phe Glu Met Phe Arg Glu Leu Ile Glu Ala
            340                 345                 350

Leu Glu Leu Lys Asp Ala Gln Ala Gly Lys Glu Pro Gly Gly Ser Arg
        355                 360                 365

Ala His Ser Ser His Leu Lys Ser Lys Lys Gly Gln Ser Thr Ser Arg
    370                 375                 380

His Lys Lys Leu Met Phe Lys Thr Glu Gly Pro Asp Ser Asp Pro Leu
385                 390                 395                 400

Val Leu Ala Ile Ala Ala Val Leu
                405
```

<210> SEQ ID NO 17
<211> LENGTH: 1257
<212> TYPE: DNA
<213> ORGANISM: Artificial Sequence
<220> FEATURE:
<223> OTHER INFORMATION: NLS-JO-39 MTD-p53-JO-39 MTD cDNA Sequence

<400> SEQUENCE: 17

```
atgaagaaga agaggaagcc gctggtgctg gcgattgcgg cggtgctgga ggagccgcag      60

tcagatccta gcgtcgagcc ccctctgagt caggaaacat tttcagacct atggaaacta     120

cttcctgaaa acaacgttct gtcccccttg ccgtcccaag caatggatga tttgatgctg     180

tccccggacg atattgaaca atggttcact gaagacccag gtccagatga agctcccaga     240

atgccagagg ctgctccccg cgtggcccct gcaccagcag ctcctacacc ggcggcccct     300

gcaccagccc cctcctggcc cctgtcatct tctgtccctt cccagaaaac ctaccagggc     360

agctacggtt tccgtctggg cttcttgcat tctgggacag ccaagtctgt gacttgcacg     420

tactcccctg ccctcaacaa gatgttttgc caactggcca agacctgccc tgtgcagctg     480

tgggttgatt ccacaccccc gcccggcacc cgcgtccgcg ccatggccat ctacaagcag     540

tcacagcaca tgacggaggt tgtgaggcgc tgcccccacc atgagcgctg ctcagatagc     600

gatggtctgg cccctcctca gcatcttatc cgagtggaag gaaatttgcg tgtggagtat     660

ttggatgaca gaaacacttt tcgacatagt gtggtggtgc cctatgagcc gcctgaggtt     720

ggctctgact gtaccaccat ccactacaac tacatgtgta acagttcctg catgggcggc     780

atgaaccgga ggcccatcct caccatcatc acactggaag actccagtgg taatctactg     840

ggacggaaca gctttgaggt gcgtgtttgt gcctgtcctg ggagagaccg gcgcacagag     900

gaagagaatc tccgcaagaa aggggagcct caccacgagc tgcccccagg gagcactaag     960

cgagcactgc ccaacaacac cagctcctct ccccagccaa agaagaaacc actggatgga    1020

ggatatttca cccttcagat ccgtgggcgt gagcgcttcg agatgttccg agagctgatt    1080

gaggccttgg aactcaagga tgcccaggct gggaaggagc caggggggag cagggctcac    1140

tccagccacc tgaagtccaa aaagggtcag tctacctccc gccataaaaa actcatgttc    1200

aagacagaag ggcctgactc agacccgctg gtgctggcga ttgcggcggt gctgtga       1257

<210> SEQ ID NO 18
<211> LENGTH: 418
<212> TYPE: PRT
<213> ORGANISM: Artificial Sequence
<220> FEATURE:
<223> OTHER INFORMATION: NLS-JO-39 MTD-p53-JO-39 MTD Amino Acid Sequence

<400> SEQUENCE: 18

Met Lys Lys Lys Arg Lys Pro Leu Val Leu Ala Ile Ala Ala Val Leu
1               5                   10                  15

Glu Glu Pro Gln Ser Asp Pro Ser Val Glu Pro Pro Leu Ser Gln Glu
            20                  25                  30

Thr Phe Ser Asp Leu Trp Lys Leu Leu Pro Glu Asn Asn Val Leu Ser
        35                  40                  45

Pro Leu Pro Ser Gln Ala Met Asp Asp Leu Met Leu Ser Pro Asp Asp
    50                  55                  60

Ile Glu Gln Trp Phe Thr Glu Asp Pro Gly Pro Asp Glu Ala Pro Arg
65                  70                  75                  80

Met Pro Glu Ala Ala Pro Arg Val Ala Pro Ala Pro Ala Ala Pro Thr
                85                  90                  95

Pro Ala Ala Pro Ala Pro Ala Pro Ser Trp Pro Leu Ser Ser Ser Val
            100                 105                 110

Pro Ser Gln Lys Thr Tyr Gln Gly Ser Tyr Gly Phe Arg Leu Gly Phe
        115                 120                 125

Leu His Ser Gly Thr Ala Lys Ser Val Thr Cys Thr Tyr Ser Pro Ala
    130                 135                 140
```

Leu Asn Lys Met Phe Cys Gln Leu Ala Lys Thr Cys Pro Val Gln Leu
145 150 155 160

Trp Val Asp Ser Thr Pro Pro Pro Gly Thr Arg Val Arg Ala Met Ala
165 170 175

Ile Tyr Lys Gln Ser Gln His Met Thr Glu Val Val Arg Arg Cys Pro
180 185 190

His His Glu Arg Cys Ser Asp Ser Asp Gly Leu Ala Pro Pro Gln His
195 200 205

Leu Ile Arg Val Glu Gly Asn Leu Arg Val Glu Tyr Leu Asp Asp Arg
210 215 220

Asn Thr Phe Arg His Ser Val Val Val Pro Tyr Glu Pro Pro Glu Val
225 230 235 240

Gly Ser Asp Cys Thr Thr Ile His Tyr Asn Tyr Met Cys Asn Ser Ser
245 250 255

Cys Met Gly Gly Met Asn Arg Arg Pro Ile Leu Thr Ile Ile Thr Leu
260 265 270

Glu Asp Ser Ser Gly Asn Leu Leu Gly Arg Asn Ser Phe Glu Val Arg
275 280 285

Val Cys Ala Cys Pro Gly Arg Asp Arg Arg Thr Glu Glu Glu Asn Leu
290 295 300

Arg Lys Lys Gly Glu Pro His His Glu Leu Pro Pro Gly Ser Thr Lys
305 310 315 320

Arg Ala Leu Pro Asn Asn Thr Ser Ser Ser Pro Gln Pro Lys Lys Lys
325 330 335

Pro Leu Asp Gly Gly Tyr Phe Thr Leu Gln Ile Arg Gly Arg Glu Arg
340 345 350

Phe Glu Met Phe Arg Glu Leu Ile Glu Ala Leu Glu Leu Lys Asp Ala
355 360 365

Gln Ala Gly Lys Glu Pro Gly Gly Ser Arg Ala His Ser Ser His Leu
370 375 380

Lys Ser Lys Lys Gly Gln Ser Thr Ser Arg His Lys Lys Leu Met Phe
385 390 395 400

Lys Thr Glu Gly Pro Asp Ser Asp Pro Leu Val Leu Ala Ile Ala Ala
405 410 415

Val Leu

<210> SEQ ID NO 19
<211> LENGTH: 1221
<212> TYPE: DNA
<213> ORGANISM: Artificial Sequence
<220> FEATURE:
<223> OTHER INFORMATION: NLS-JO-41 MTD-p53 cDNA Sequence

<400> SEQUENCE: 19
atgaagaaga agaggaaggc ggcggcgctg ctggcggtgg cggaggagcc gcagtcagat 60
cctagcgtcg agcccccctct gagtcaggaa acattttcag acctatggaa actacttcct 120
gaaaacaacg ttctgtcccc cttgccgtcc caagcaatgg atgatttgat gctgtccccg 180
gacgatattg aacaatggtt cactgaagac ccaggtccag atgaagctcc cagaatgcca 240
gaggctgctc cccgcgtggc ccctgcacca gcagctccta caccggcggc ccctgcacca 300
gccccctcct ggcccctgtc atcttctgtc ccttcccaga aaacctacca gggcagctac 360
ggtttccgtc tgggcttctt gcattctggg acagccaagt ctgtgacttg cacgtactcc 420
cctgccctca acaagatgtt ttgccaactg gccaagacct gccctgtgca gctgtgggtt 480
gattccacac ccccgcccgg cacccgcgtc cgcgccatgg ccatctacaa gcagtcacag 540

```
cacatgacgg aggttgtgag gcgctgcccc caccatgagc gctgctcaga tagcgatggt    600

ctggcccctc ctcagcatct tatccgagtg gaaggaaatt tgcgtgtgga gtatttggat    660

gacagaaaca cttttcgaca tagtgtggtg gtgccctatg agccgcctga ggttggctct    720

gactgtacca ccatccacta caactacatg tgtaacagtt cctgcatggg cggcatgaac    780

cggaggccca tcctcaccat catcacactg gaagactcca gtggtaatct actgggacgg    840

aacagctttg aggtgcgtgt ttgtgcctgt cctgggagag accggcgcac agaggaagag    900

aatctccgca agaaagggga gcctcaccac gagctgcccc cagggagcac taagcgagca    960

ctgcccaaca acaccagctc ctctccccag ccaaagaaga aaccactgga tggaggatat   1020

ttcacccttc agatccgtgg gcgtgagcgc ttcgagatgt tccgagagct gattgaggcc   1080

ttggaactca aggatgccca ggctgggaag gagccagggg ggagcagggc tcactccagc   1140

cacctgaagt ccaaaaaggg tcagtctacc tcccgccata aaaaactcat gttcaagaca   1200

gaagggcctg actcagactg a                                             1221
```

```
<210> SEQ ID NO 20
<211> LENGTH: 406
<212> TYPE: PRT
<213> ORGANISM: Artificial Sequence
<220> FEATURE:
<223> OTHER INFORMATION: NLS-JO-41 MTD-p53 Amino Acid Sequence

<400> SEQUENCE: 20

Met Lys Lys Lys Arg Lys Ala Ala Ala Leu Leu Ala Val Ala Glu Glu
  1               5                  10                  15

Pro Gln Ser Asp Pro Ser Val Glu Pro Pro Leu Ser Gln Glu Thr Phe
             20                  25                  30

Ser Asp Leu Trp Lys Leu Leu Pro Glu Asn Asn Val Leu Ser Pro Leu
         35                  40                  45

Pro Ser Gln Ala Met Asp Asp Leu Met Leu Ser Pro Asp Asp Ile Glu
     50                  55                  60

Gln Trp Phe Thr Glu Asp Pro Gly Pro Asp Glu Ala Pro Arg Met Pro
 65                  70                  75                  80

Glu Ala Ala Pro Arg Val Ala Pro Ala Pro Ala Ala Pro Thr Pro Ala
                 85                  90                  95

Ala Pro Ala Pro Ala Pro Ser Trp Pro Leu Ser Ser Ser Val Pro Ser
            100                 105                 110

Gln Lys Thr Tyr Gln Gly Ser Tyr Gly Phe Arg Leu Gly Phe Leu His
        115                 120                 125

Ser Gly Thr Ala Lys Ser Val Thr Cys Thr Tyr Ser Pro Ala Leu Asn
    130                 135                 140

Lys Met Phe Cys Gln Leu Ala Lys Thr Cys Pro Val Gln Leu Trp Val
145                 150                 155                 160

Asp Ser Thr Pro Pro Pro Gly Thr Arg Val Arg Ala Met Ala Ile Tyr
                165                 170                 175

Lys Gln Ser Gln His Met Thr Glu Val Val Arg Arg Cys Pro His His
            180                 185                 190

Glu Arg Cys Ser Asp Ser Asp Gly Leu Ala Pro Pro Gln His Leu Ile
        195                 200                 205

Arg Val Glu Gly Asn Leu Arg Val Glu Tyr Leu Asp Asp Arg Asn Thr
    210                 215                 220

Phe Arg His Ser Val Val Val Pro Tyr Glu Pro Pro Glu Val Gly Ser
225                 230                 235                 240
```

```
Asp Cys Thr Thr Ile His Tyr Asn Tyr Met Cys Asn Ser Ser Cys Met
                245                 250                 255

Gly Gly Met Asn Arg Arg Pro Ile Leu Thr Ile Ile Thr Leu Glu Asp
            260                 265                 270

Ser Ser Gly Asn Leu Leu Gly Arg Asn Ser Phe Glu Val Arg Val Cys
        275                 280                 285

Ala Cys Pro Gly Arg Asp Arg Arg Thr Glu Glu Glu Asn Leu Arg Lys
    290                 295                 300

Lys Gly Glu Pro His His Glu Leu Pro Pro Gly Ser Thr Lys Arg Ala
305                 310                 315                 320

Leu Pro Asn Asn Thr Ser Ser Ser Pro Gln Pro Lys Lys Lys Pro Leu
                325                 330                 335

Asp Gly Gly Tyr Phe Thr Leu Gln Ile Arg Gly Arg Glu Arg Phe Glu
            340                 345                 350

Met Phe Arg Glu Leu Ile Glu Ala Leu Glu Leu Lys Asp Ala Gln Ala
        355                 360                 365

Gly Lys Glu Pro Gly Gly Ser Arg Ala His Ser Ser His Leu Lys Ser
    370                 375                 380

Lys Lys Gly Gln Ser Thr Ser Arg His Lys Lys Leu Met Phe Lys Thr
385                 390                 395                 400

Glu Gly Pro Asp Ser Asp
                405
```

```
<210> SEQ ID NO 21
<211> LENGTH: 1221
<212> TYPE: DNA
<213> ORGANISM: Artificial Sequence
<220> FEATURE:
<223> OTHER INFORMATION: NLS-p53-JO-41 MTD cDNA Sequence

<400> SEQUENCE: 21

atgaagaaga agaggaagga ggagccgcag tcagatccta gcgtcgagcc ccctctgagt      60

caggaaacat tttcagacct atggaaacta cttcctgaaa acaacgttct gtcccccttg     120

ccgtcccaag caatggatga tttgatgctg tccccggacg atattgaaca atggttcact     180

gaagacccag gtccagatga agctcccaga atgccagagg ctgctccccg cgtggcccct     240

gcaccagcag ctcctacacc ggcggcccct gcaccagccc cctcctggcc cctgtcatct     300

tctgtccctt cccagaaaac ctaccagggc agctacggtt tccgtctggg cttcttgcat     360

tctgggacag ccaagtctgt gacttgcacg tactcccctg ccctcaacaa gatgttttgc     420

caactggcca agacctgccc tgtgcagctg tgggttgatt ccacaccccc gcccggcacc     480

cgcgtccgcg ccatggccat ctacaagcag tcacagcaca tgacggaggt tgtgaggcgc     540

tgcccccacc atgagcgctg ctcagatagc gatggtctgg cccctcctca gcatcttatc     600

cgagtggaag gaaatttgcg tgtggagtat ttggatgaca gaaacacttt tcgacatagt     660

gtggtggtgc cctatgagcc gcctgaggtt ggctctgact gtaccaccat ccactacaac     720

tacatgtgta acagttcctg catgggcggc atgaaccgga ggcccatcct caccatcatc     780

acactggaag actccagtgg taatctactg ggacggaaca gctttgaggt gcgtgtttgt     840

gcctgtcctg ggagagaccg gcgcacagag gaagagaatc tccgcaagaa aggggagcct     900

caccacgagc tgcccccagg gagcactaag cgagcactgc ccaacaacac cagctcctct     960

ccccagccaa agaagaaacc actggatgga ggatatttca cccttcagat ccgtgggcgt    1020

gagcgcttcg agatgttccg agagctgatt gaggccttgg aactcaagga tgcccaggct    1080

gggaaggagc caggggggag cagggctcac tccagccacc tgaagtccaa aaagggtcag    1140
```

```
tctacctccc gccataaaaa actcatgttc aagacagaag ggcctgactc agacgcggcg   1200

gcgctgctgg cggtggcgtg a                                              1221


<210> SEQ ID NO 22
<211> LENGTH: 406
<212> TYPE: PRT
<213> ORGANISM: Artificial Sequence
<220> FEATURE:
<223> OTHER INFORMATION: NLS-p53-JO-41 MTD Amino Acid Sequence

<400> SEQUENCE: 22

Met Lys Lys Lys Arg Lys Glu Glu Pro Gln Ser Asp Pro Ser Val Glu
  1               5                  10                  15

Pro Pro Leu Ser Gln Glu Thr Phe Ser Asp Leu Trp Lys Leu Leu Pro
            20                  25                  30

Glu Asn Asn Val Leu Ser Pro Leu Pro Ser Gln Ala Met Asp Asp Leu
        35                  40                  45

Met Leu Ser Pro Asp Asp Ile Glu Gln Trp Phe Thr Glu Asp Pro Gly
    50                  55                  60

Pro Asp Glu Ala Pro Arg Met Pro Glu Ala Ala Pro Arg Val Ala Pro
 65                  70                  75                  80

Ala Pro Ala Ala Pro Thr Pro Ala Ala Pro Ala Pro Ala Pro Ser Trp
                85                  90                  95

Pro Leu Ser Ser Ser Val Pro Ser Gln Lys Thr Tyr Gln Gly Ser Tyr
            100                 105                 110

Gly Phe Arg Leu Gly Phe Leu His Ser Gly Thr Ala Lys Ser Val Thr
        115                 120                 125

Cys Thr Tyr Ser Pro Ala Leu Asn Lys Met Phe Cys Gln Leu Ala Lys
    130                 135                 140

Thr Cys Pro Val Gln Leu Trp Val Asp Ser Thr Pro Pro Pro Gly Thr
145                 150                 155                 160

Arg Val Arg Ala Met Ala Ile Tyr Lys Gln Ser Gln His Met Thr Glu
                165                 170                 175

Val Val Arg Arg Cys Pro His His Glu Arg Cys Ser Asp Ser Asp Gly
            180                 185                 190

Leu Ala Pro Pro Gln His Leu Ile Arg Val Glu Gly Asn Leu Arg Val
        195                 200                 205

Glu Tyr Leu Asp Asp Arg Asn Thr Phe Arg His Ser Val Val Val Pro
    210                 215                 220

Tyr Glu Pro Pro Glu Val Gly Ser Asp Cys Thr Thr Ile His Tyr Asn
225                 230                 235                 240

Tyr Met Cys Asn Ser Ser Cys Met Gly Gly Met Asn Arg Arg Pro Ile
                245                 250                 255

Leu Thr Ile Ile Thr Leu Glu Asp Ser Ser Gly Asn Leu Leu Gly Arg
            260                 265                 270

Asn Ser Phe Glu Val Arg Val Cys Ala Cys Pro Gly Arg Asp Arg Arg
        275                 280                 285

Thr Glu Glu Glu Asn Leu Arg Lys Lys Gly Glu Pro His His Glu Leu
    290                 295                 300

Pro Pro Gly Ser Thr Lys Arg Ala Leu Pro Asn Asn Thr Ser Ser Ser
305                 310                 315                 320

Pro Gln Pro Lys Lys Lys Pro Leu Asp Gly Gly Tyr Phe Thr Leu Gln
                325                 330                 335

Ile Arg Gly Arg Glu Arg Phe Glu Met Phe Arg Glu Leu Ile Glu Ala
            340                 345                 350
```

```
Leu Glu Leu Lys Asp Ala Gln Ala Gly Lys Glu Pro Gly Gly Ser Arg
        355                 360                 365

Ala His Ser Ser His Leu Lys Ser Lys Lys Gly Gln Ser Thr Ser Arg
    370                 375                 380

His Lys Lys Leu Met Phe Lys Thr Glu Gly Pro Asp Ser Asp Ala Ala
385                 390                 395                 400

Ala Leu Leu Ala Val Ala
                405


<210> SEQ ID NO 23
<211> LENGTH: 1245
<212> TYPE: DNA
<213> ORGANISM: Artificial Sequence
<220> FEATURE:
<223> OTHER INFORMATION: NLS-JO-41 MTD-p53- JO-41 MTD cDNA Sequence

<400> SEQUENCE: 23

atgaagaaga agaggaaggc ggcggcgctg ctggcggtgg cggaggagcc gcagtcagat     60

cctagcgtcg agcccccctct gagtcaggaa acattttcag acctatggaa actacttcct    120

gaaaacaacg ttctgtcccc cttgccgtcc caagcaatgg atgatttgat gctgtccccg    180

gacgatattg aacaatggtt cactgaagac ccaggtccag atgaagctcc cagaatgcca    240

gaggctgctc cccgcgtggc ccctgcacca gcagctccta caccggcggc ccctgcacca    300

gccccctcct ggcccctgtc atcttctgtc ccttcccaga aaacctacca gggcagctac    360

ggtttccgtc tgggcttctt gcattctggg acagccaagt ctgtgacttg cacgtactcc    420

cctgccctca acaagatgtt ttgccaactg gccaagacct gccctgtgca gctgtgggtt    480

gattccacac ccccgcccgg cacccgcgtc cgcgccatgg ccatctacaa gcagtcacag    540

cacatgacgg aggttgtgag gcgctgcccc caccatgagc gctgctcaga tagcgatggt    600

ctggcccctc ctcagcatct tatccgagtg gaaggaaatt tgcgtgtgga gtatttggat    660

gacagaaaca cttttcgaca tagtgtggtg gtgccctatg agccgcctga ggttggctct    720

gactgtacca ccatccacta caactacatg tgtaacagtt cctgcatggg cggcatgaac    780

cggaggccca tcctcaccat catcacactg gaagactcca gtggtaatct actgggacgg    840

aacagctttg aggtgcgtgt ttgtgcctgt cctgggagag accggcgcac agaggaagag    900

aatctccgca agaaagggga gcctcaccac gagctgcccc cagggagcac taagcgagca    960

ctgcccaaca acaccagctc ctctccccag ccaaagaaga aaccactgga tggaggatat   1020

ttcacccttc agatccgtgg gcgtgagcgc ttcgagatgt tccgagagct gattgaggcc   1080

ttggaactca aggatgccca ggctgggaag gagccagggg ggagcagggc tcactccagc   1140

cacctgaagt ccaaaaaggg tcagtctacc tcccgccata aaaaactcat gttcaagaca   1200

gaagggcctg actcagacgc ggcggcgctg ctggcggtgg cgtga                   1245


<210> SEQ ID NO 24
<211> LENGTH: 414
<212> TYPE: PRT
<213> ORGANISM: Artificial Sequence
<220> FEATURE:
<223> OTHER INFORMATION: NLS-JO-41 MTD-p53-JO-41 MTD Amino Acid Sequence

<400> SEQUENCE: 24

Met Lys Lys Lys Arg Lys Ala Ala Ala Leu Leu Ala Val Ala Glu Glu
  1               5                  10                  15

Pro Gln Ser Asp Pro Ser Val Glu Pro Pro Leu Ser Gln Glu Thr Phe
             20                  25                  30
```

```
Ser Asp Leu Trp Lys Leu Leu Pro Glu Asn Asn Val Leu Ser Pro Leu
        35                  40                  45

Pro Ser Gln Ala Met Asp Asp Leu Met Leu Ser Pro Asp Asp Ile Glu
    50                  55                  60

Gln Trp Phe Thr Glu Asp Pro Gly Pro Asp Glu Ala Pro Arg Met Pro
65                  70                  75                  80

Glu Ala Ala Pro Arg Val Ala Pro Ala Pro Ala Ala Pro Thr Pro Ala
                85                  90                  95

Ala Pro Ala Pro Ala Pro Ser Trp Pro Leu Ser Ser Ser Val Pro Ser
            100                 105                 110

Gln Lys Thr Tyr Gln Gly Ser Tyr Gly Phe Arg Leu Gly Phe Leu His
        115                 120                 125

Ser Gly Thr Ala Lys Ser Val Thr Cys Thr Tyr Ser Pro Ala Leu Asn
    130                 135                 140

Lys Met Phe Cys Gln Leu Ala Lys Thr Cys Pro Val Gln Leu Trp Val
145                 150                 155                 160

Asp Ser Thr Pro Pro Pro Gly Thr Arg Val Arg Ala Met Ala Ile Tyr
                165                 170                 175

Lys Gln Ser Gln His Met Thr Glu Val Val Arg Arg Cys Pro His His
            180                 185                 190

Glu Arg Cys Ser Asp Ser Asp Gly Leu Ala Pro Pro Gln His Leu Ile
        195                 200                 205

Arg Val Glu Gly Asn Leu Arg Val Glu Tyr Leu Asp Asp Arg Asn Thr
    210                 215                 220

Phe Arg His Ser Val Val Val Pro Tyr Glu Pro Pro Glu Val Gly Ser
225                 230                 235                 240

Asp Cys Thr Thr Ile His Tyr Asn Tyr Met Cys Asn Ser Ser Cys Met
                245                 250                 255

Gly Gly Met Asn Arg Arg Pro Ile Leu Thr Ile Ile Thr Leu Glu Asp
            260                 265                 270

Ser Ser Gly Asn Leu Leu Gly Arg Asn Ser Phe Glu Val Arg Val Cys
        275                 280                 285

Ala Cys Pro Gly Arg Asp Arg Arg Thr Glu Glu Glu Asn Leu Arg Lys
    290                 295                 300

Lys Gly Glu Pro His His Glu Leu Pro Pro Gly Ser Thr Lys Arg Ala
305                 310                 315                 320

Leu Pro Asn Asn Thr Ser Ser Ser Pro Gln Pro Lys Lys Lys Pro Leu
                325                 330                 335

Asp Gly Gly Tyr Phe Thr Leu Gln Ile Arg Gly Arg Glu Arg Phe Glu
            340                 345                 350

Met Phe Arg Glu Leu Ile Glu Ala Leu Glu Leu Lys Asp Ala Gln Ala
        355                 360                 365

Gly Lys Glu Pro Gly Gly Ser Arg Ala His Ser Ser His Leu Lys Ser
    370                 375                 380

Lys Lys Gly Gln Ser Thr Ser Arg His Lys Lys Leu Met Phe Lys Thr
385                 390                 395                 400

Glu Gly Pro Asp Ser Asp Ala Ala Ala Leu Leu Ala Val Ala
                405                 410
```

```
<210> SEQ ID NO 25
<211> LENGTH: 309
<212> TYPE: DNA
<213> ORGANISM: Artificial Sequence
<220> FEATURE:
<223> OTHER INFORMATION: deltap53 cDNA Sequence
```

<400> SEQUENCE: 25

```
atggaggagc cgcagtcaga tcctagcgtc gagccccctc tgagtcagga aacattttca     60

gacctatgga aactacttcc tgaaaacaac gttctgtccc ccttgccgtc ccaagcaatg    120

gatgatttga tgctgtcccc ggacgatatt gaacaatggt tcactgaaga cccaggtcca    180

gatgaagctc ccagaatgcc agaggctgct ccccgcgtgg cccctgcacc agcagctcct    240

acaccggcgg cccctgcacc agccccctcc tggcccctgt catcttctgt cccttcccag    300

aaaacctga                                                             309
```

<210> SEQ ID NO 26
<211> LENGTH: 102
<212> TYPE: PRT
<213> ORGANISM: Artificial Sequence
<220> FEATURE:
<223> OTHER INFORMATION: deltap53 Amino Acid Sequence

<400> SEQUENCE: 26

```
Met Glu Glu Pro Gln Ser Asp Pro Ser Val Glu Pro Pro Leu Ser Gln
  1               5                  10                  15

Glu Thr Phe Ser Asp Leu Trp Lys Leu Leu Pro Glu Asn Asn Val Leu
             20                  25                  30

Ser Pro Leu Pro Ser Gln Ala Met Asp Asp Leu Met Leu Ser Pro Asp
         35                  40                  45

Asp Ile Glu Gln Trp Phe Thr Glu Asp Pro Gly Pro Asp Glu Ala Pro
     50                  55                  60

Arg Met Pro Glu Ala Ala Pro Arg Val Ala Pro Ala Pro Ala Ala Pro
 65                  70                  75                  80

Thr Pro Ala Ala Pro Ala Pro Ala Pro Ser Trp Pro Leu Ser Ser Ser
                 85                  90                  95

Val Pro Ser Gln Lys Thr
            100
```

<210> SEQ ID NO 27
<211> LENGTH: 339
<212> TYPE: DNA
<213> ORGANISM: Artificial Sequence
<220> FEATURE:
<223> OTHER INFORMATION: JO-39 MTD-deltap53 cDNA Sequence

<400> SEQUENCE: 27

```
atgccgctgg tgctggcgat tgcggcggtg ctggaggagc cgcagtcaga tcctagcgtc     60

gagccccctc tgagtcagga aacattttca gacctatgga aactacttcc tgaaaacaac    120

gttctgtccc ccttgccgtc ccaagcaatg gatgatttga tgctgtcccc ggacgatatt    180

gaacaatggt tcactgaaga cccaggtcca gatgaagctc ccagaatgcc agaggctgct    240

ccccgcgtgg cccctgcacc agcagctcct acaccggcgg cccctgcacc agccccctcc    300

tggcccctgt catcttctgt cccttcccag aaaacctga                            339
```

<210> SEQ ID NO 28
<211> LENGTH: 112
<212> TYPE: PRT
<213> ORGANISM: Artificial Sequence
<220> FEATURE:
<223> OTHER INFORMATION: JO-39 MTD-deltap53 Amino Acid Sequence

<400> SEQUENCE: 28

```
Met Pro Leu Val Leu Ala Ile Ala Ala Val Leu Glu Glu Pro Gln Ser
  1               5                  10                  15
```

```
Asp Pro Ser Val Glu Pro Pro Leu Ser Gln Glu Thr Phe Ser Asp Leu
            20                  25                  30

Trp Lys Leu Leu Pro Glu Asn Asn Val Leu Ser Pro Leu Pro Ser Gln
        35                  40                  45

Ala Met Asp Asp Leu Met Leu Ser Pro Asp Asp Ile Glu Gln Trp Phe
    50                  55                  60

Thr Glu Asp Pro Gly Pro Asp Glu Ala Pro Arg Met Pro Glu Ala Ala
65                  70                  75                  80

Pro Arg Val Ala Pro Ala Pro Ala Ala Pro Thr Pro Ala Ala Pro Ala
                85                  90                  95

Pro Ala Pro Ser Trp Pro Leu Ser Ser Ser Val Pro Ser Gln Lys Thr
            100                 105                 110


<210> SEQ ID NO 29
<211> LENGTH: 339
<212> TYPE: DNA
<213> ORGANISM: Artificial Sequence
<220> FEATURE:
<223> OTHER INFORMATION: deltap53-JO-39 MTD cDNA Sequence

<400> SEQUENCE: 29

atggaggagc cgcagtcaga tcctagcgtc gagccccctc tgagtcagga aacattttca     60

gacctatgga aactacttcc tgaaaacaac gttctgtccc ccttgccgtc ccaagcaatg    120

gatgatttga tgctgtcccc ggacgatatt gaacaatggt tcactgaaga cccaggtcca    180

gatgaagctc ccagaatgcc agaggctgct ccccgcgtgg cccctgcacc agcagctcct    240

acaccggcgg cccctgcacc agccccctcc tggcccctgt catcttctgt cccttcccag    300

aaaaccccgc tggtgctggc gattgcggcg gtgctgtga                           339


<210> SEQ ID NO 30
<211> LENGTH: 112
<212> TYPE: PRT
<213> ORGANISM: Artificial Sequence
<220> FEATURE:
<223> OTHER INFORMATION: deltap53-JO-39 MTD Amino Acid Sequence

<400> SEQUENCE: 30

Met Glu Glu Pro Gln Ser Asp Pro Ser Val Glu Pro Pro Leu Ser Gln
  1               5                  10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Arg Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Pro Leu Val Leu Ala Ile Ala Ala Val Leu
            100                 105                 110


<210> SEQ ID NO 31
<211> LENGTH: 333
<212> TYPE: DNA
<213> ORGANISM: Artificial Sequence
<220> FEATURE:
<223> OTHER INFORMATION: JO-41 MTD-deltap53 cDNA Sequence
```

<400> SEQUENCE: 31

```
atggcggcgg cgctgctggc ggtggcggag gagccgcagt cagatcctag cgtcgagccc      60
cctctgagtc aggaaacatt ttcagaccta tggaaactac ttcctgaaaa caacgttctg     120
tccccccttgc cgtcccaagc aatggatgat ttgatgctgt ccccggacga tattgaacaa    180
tggttcactg aagacccagg tccagatgaa gctcccagaa tgccagaggc tgctccccgc     240
gtggcccctg caccagcagc tcctacaccg gcggcccctg caccagcccc ctcctggccc     300
ctgtcatctt ctgtcccttc ccagaaaacc tga                                  333
```

<210> SEQ ID NO 32
<211> LENGTH: 110
<212> TYPE: PRT
<213> ORGANISM: Artificial Sequence
<220> FEATURE:
<223> OTHER INFORMATION: JO-41 MTD-deltap53 Amino Acid Sequence

<400> SEQUENCE: 32

```
Met Ala Ala Ala Leu Leu Ala Val Ala Glu Glu Pro Gln Ser Asp Pro
  1               5                  10                  15

Ser Val Glu Pro Pro Leu Ser Gln Glu Thr Phe Ser Asp Leu Trp Lys
             20                  25                  30

Leu Leu Pro Glu Asn Asn Val Leu Ser Pro Leu Pro Ser Gln Ala Met
         35                  40                  45

Asp Asp Leu Met Leu Ser Pro Asp Asp Ile Glu Gln Trp Phe Thr Glu
     50                  55                  60

Asp Pro Gly Pro Asp Glu Ala Pro Arg Met Pro Glu Ala Ala Pro Arg
 65                  70                  75                  80

Val Ala Pro Ala Pro Ala Ala Pro Thr Pro Ala Ala Pro Ala Pro Ala
                 85                  90                  95

Pro Ser Trp Pro Leu Ser Ser Ser Val Pro Ser Gln Lys Thr
            100                 105                 110
```

<210> SEQ ID NO 33
<211> LENGTH: 333
<212> TYPE: DNA
<213> ORGANISM: Artificial Sequence
<220> FEATURE:
<223> OTHER INFORMATION: deltap53-JO-41 MTD cDNA Sequence

<400> SEQUENCE: 33

```
atggaggagc cgcagtcaga tcctagcgtc gagccccctc tgagtcagga aacattttca      60
gacctatgga aactacttcc tgaaaacaac gttctgtccc ccttgccgtc ccaagcaatg     120
gatgatttga tgctgtcccc ggacgatatt gaacaatggt tcactgaaga cccaggtcca     180
gatgaagctc ccagaatgcc agaggctgct ccccgcgtgg cccctgcacc agcagctcct     240
acaccggcgg cccctgcacc agccccctcc tggcccctgt catcttctgt cccttcccag     300
aaaaccgcgg cggcgctgct ggcggtggcg tga                                  333
```

<210> SEQ ID NO 34
<211> LENGTH: 110
<212> TYPE: PRT
<213> ORGANISM: Artificial Sequence
<220> FEATURE:
<223> OTHER INFORMATION: deltap53-JO-41 MTD Amino Acid Sequence

<400> SEQUENCE: 34

```
Met Glu Glu Pro Gln Ser Asp Pro Ser Val Glu Pro Pro Leu Ser Gln
  1               5                  10                  15
```

```
Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Arg Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Ala Ala Ala Leu Leu Ala Val Ala
            100                 105                 110


<210> SEQ ID NO 35
<211> LENGTH: 324
<212> TYPE: DNA
<213> ORGANISM: Artificial Sequence
<220> FEATURE:
<223> OTHER INFORMATION: NLS-deltap53 cDNA Sequence

<400> SEQUENCE: 35

atgaagaaga agaggaagga ggagccgcag tcagatccta gcgtcgagcc ccctctgagt      60

caggaaacat tttcagacct atggaaacta cttcctgaaa acaacgttct gtcccccttg     120

ccgtcccaag caatggatga tttgatgctg tccccggacg atattgaaca atggttcact     180

gaagacccag gtccagatga agctcccaga atgccagagg ctgctccccg cgtggcccct     240

gcaccagcag ctcctacacc ggcggcccct gcaccagccc cctcctggcc cctgtcatct     300

tctgtccctt cccagaaaac ctga                                            324


<210> SEQ ID NO 36
<211> LENGTH: 107
<212> TYPE: PRT
<213> ORGANISM: Artificial Sequence
<220> FEATURE:
<223> OTHER INFORMATION: NLS-deltap53 Amino Acid Sequence

<400> SEQUENCE: 36

Met Lys Lys Lys Arg Lys Glu Glu Pro Gln Ser Asp Pro Ser Val Glu
1               5                   10                  15

Pro Pro Leu Ser Gln Glu Thr Phe Ser Asp Leu Trp Lys Leu Leu Pro
            20                  25                  30

Glu Asn Asn Val Leu Ser Pro Leu Pro Ser Gln Ala Met Asp Asp Leu
        35                  40                  45

Met Leu Ser Pro Asp Asp Ile Glu Gln Trp Phe Thr Glu Asp Pro Gly
    50                  55                  60

Pro Asp Glu Ala Pro Arg Met Pro Glu Ala Ala Pro Arg Val Ala Pro
65                  70                  75                  80

Ala Pro Ala Ala Pro Thr Pro Ala Ala Pro Ala Pro Ala Pro Ser Trp
                85                  90                  95

Pro Leu Ser Ser Ser Val Pro Ser Gln Lys Thr
            100                 105


<210> SEQ ID NO 37
<211> LENGTH: 354
<212> TYPE: DNA
<213> ORGANISM: Artificial Sequence
<220> FEATURE:
<223> OTHER INFORMATION: NLS-JO-39 MTD-deltap53 cDNA Sequence

<400> SEQUENCE: 37
```

```
atgaagaaga agaggaagcc gctggtgctg gcgattgcgg cggtgctgga ggagccgcag     60

tcagatccta gcgtcgagcc ccctctgagt caggaaacat tttcagacct atggaaacta    120

cttcctgaaa acaacgttct gtcccccttg ccgtcccaag caatggatga tttgatgctg    180

tccccggacg atattgaaca atggttcact gaagacccag gtccagatga agctcccaga    240

atgccagagg ctgctccccg cgtggcccct gcaccagcag ctcctacacc ggcggcccct    300

gcaccagccc cctcctggcc cctgtcatct tctgtccctt cccagaaaac ctga          354


<210> SEQ ID NO 38
<211> LENGTH: 117
<212> TYPE: PRT
<213> ORGANISM: Artificial Sequence
<220> FEATURE:
<223> OTHER INFORMATION: NLS-JO-39 MTD-deltap53 Amino Acid Sequence

<400> SEQUENCE: 38

Met Lys Lys Lys Arg Lys Pro Leu Val Leu Ala Ile Ala Ala Val Leu
  1               5                  10                  15

Glu Glu Pro Gln Ser Asp Pro Ser Val Glu Pro Pro Leu Ser Gln Glu
             20                  25                  30

Thr Phe Ser Asp Leu Trp Lys Leu Leu Pro Glu Asn Asn Val Leu Ser
         35                  40                  45

Pro Leu Pro Ser Gln Ala Met Asp Asp Leu Met Leu Ser Pro Asp Asp
     50                  55                  60

Ile Glu Gln Trp Phe Thr Glu Asp Pro Gly Pro Asp Glu Ala Pro Arg
 65                  70                  75                  80

Met Pro Glu Ala Ala Pro Arg Val Ala Pro Ala Pro Ala Ala Pro Thr
                 85                  90                  95

Pro Ala Ala Pro Ala Pro Ala Pro Ser Trp Pro Leu Ser Ser Ser Val
            100                 105                 110

Pro Ser Gln Lys Thr
        115


<210> SEQ ID NO 39
<211> LENGTH: 354
<212> TYPE: DNA
<213> ORGANISM: Artificial Sequence
<220> FEATURE:
<223> OTHER INFORMATION: NLS-deltap53-JO-39 MTD cDNA Sequence

<400> SEQUENCE: 39

atgaagaaga agaggaagga ggagccgcag tcagatccta gcgtcgagcc ccctctgagt     60

caggaaacat tttcagacct atggaaacta cttcctgaaa acaacgttct gtcccccttg    120

ccgtcccaag caatggatga tttgatgctg tccccggacg atattgaaca atggttcact    180

gaagacccag gtccagatga agctcccaga atgccagagg ctgctccccg cgtggcccct    240

gcaccagcag ctcctacacc ggcggcccct gcaccagccc cctcctggcc cctgtcatct    300

tctgtccctt cccagaaaac cccgctggtg ctggcgattg cggcggtgct gtga          354


<210> SEQ ID NO 40
<211> LENGTH: 117
<212> TYPE: PRT
<213> ORGANISM: Artificial Sequence
<220> FEATURE:
<223> OTHER INFORMATION: NLS-deltap53-JO-39 MTD Amino Acid Sequence

<400> SEQUENCE: 40

Met Lys Lys Lys Arg Lys Glu Glu Pro Gln Ser Asp Pro Ser Val Glu
```

```
  1               5                  10                  15

Pro Pro Leu Ser Gln Glu Thr Phe Ser Asp Leu Trp Lys Leu Leu Pro
            20                  25                  30

Glu Asn Asn Val Leu Ser Pro Leu Pro Ser Gln Ala Met Asp Asp Leu
        35                  40                  45

Met Leu Ser Pro Asp Asp Ile Glu Gln Trp Phe Thr Glu Asp Pro Gly
    50                  55                  60

Pro Asp Glu Ala Pro Arg Met Pro Glu Ala Ala Pro Arg Val Ala Pro
 65                  70                  75                  80

Ala Pro Ala Ala Pro Thr Pro Ala Ala Pro Ala Pro Ala Pro Ser Trp
                85                  90                  95

Pro Leu Ser Ser Ser Val Pro Ser Gln Lys Thr Pro Leu Val Leu Ala
            100                 105                 110

Ile Ala Ala Val Leu
        115


<210> SEQ ID NO 41
<211> LENGTH: 348
<212> TYPE: DNA
<213> ORGANISM: Artificial Sequence
<220> FEATURE:
<223> OTHER INFORMATION: NLS-JO-41 MTD-deltap53 cDNA Sequence

<400> SEQUENCE: 41

atgaagaaga agaggaaggc ggcggcgctg ctggcggtgg cggaggagcc gcagtcagat     60

cctagcgtcg agcccctct gagtcaggaa acattttcag acctatggaa actacttcct    120

gaaaacaacg ttctgtcccc cttgccgtcc caagcaatgg atgatttgat gctgtccccg    180

gacgatattg aacaatggtt cactgaagac ccaggtccag atgaagctcc cagaatgcca    240

gaggctgctc cccgcgtggc ccctgcacca gcagctccta caccggcggc ccctgcacca    300

gcccctcct ggcccctgtc atcttctgtc ccttcccaga aaacctga                  348


<210> SEQ ID NO 42
<211> LENGTH: 115
<212> TYPE: PRT
<213> ORGANISM: Artificial Sequence
<220> FEATURE:
<223> OTHER INFORMATION: NLS-JO-41 MTD-deltap53 Amino Acid Sequence

<400> SEQUENCE: 42

Met Lys Lys Lys Arg Lys Ala Ala Ala Leu Leu Ala Val Ala Glu Glu
  1               5                  10                  15

Pro Gln Ser Asp Pro Ser Val Glu Pro Pro Leu Ser Gln Glu Thr Phe
            20                  25                  30

Ser Asp Leu Trp Lys Leu Leu Pro Glu Asn Asn Val Leu Ser Pro Leu
        35                  40                  45

Pro Ser Gln Ala Met Asp Asp Leu Met Leu Ser Pro Asp Asp Ile Glu
    50                  55                  60

Gln Trp Phe Thr Glu Asp Pro Gly Pro Asp Glu Ala Pro Arg Met Pro
 65                  70                  75                  80

Glu Ala Ala Pro Arg Val Ala Pro Ala Pro Ala Ala Pro Thr Pro Ala
                85                  90                  95

Ala Pro Ala Pro Ala Pro Ser Trp Pro Leu Ser Ser Ser Val Pro Ser
            100                 105                 110

Gln Lys Thr
        115
```

```
<210> SEQ ID NO 43
<211> LENGTH: 348
<212> TYPE: DNA
<213> ORGANISM: Artificial Sequence
<220> FEATURE:
<223> OTHER INFORMATION: NLS-deltap53-JO-41 MTD cDNA Sequence

<400> SEQUENCE: 43

atgaagaaga agaggaagga ggagccgcag tcagatccta gcgtcgagcc ccctctgagt     60

caggaaacat tttcagacct atggaaacta cttcctgaaa acaacgttct gtcccccttg    120

ccgtcccaag caatggatga tttgatgctg tccccggacg atattgaaca atggttcact    180

gaagacccag gtccagatga agctcccaga atgccagagg ctgctccccg cgtggcccct    240

gcaccagcag ctcctacacc ggcggcccct gcaccagccc cctcctggcc cctgtcatct    300

tctgtccctt cccagaaaac cgcggcggcg ctgctggcgg tggcgtga                 348


<210> SEQ ID NO 44
<211> LENGTH: 115
<212> TYPE: PRT
<213> ORGANISM: Artificial Sequence
<220> FEATURE:
<223> OTHER INFORMATION: NLS-deltap53-JO-41 MTD Amino Acid Sequence

<400> SEQUENCE: 44

Met Lys Lys Lys Arg Lys Glu Glu Pro Gln Ser Asp Pro Ser Val Glu
  1               5                  10                  15

Pro Pro Leu Ser Gln Glu Thr Phe Ser Asp Leu Trp Lys Leu Leu Pro
             20                  25                  30

Glu Asn Asn Val Leu Ser Pro Leu Pro Ser Gln Ala Met Asp Asp Leu
         35                  40                  45

Met Leu Ser Pro Asp Asp Ile Glu Gln Trp Phe Thr Glu Asp Pro Gly
     50                  55                  60

Pro Asp Glu Ala Pro Arg Met Pro Glu Ala Ala Pro Arg Val Ala Pro
 65                  70                  75                  80

Ala Pro Ala Ala Pro Thr Pro Ala Ala Pro Ala Pro Ala Pro Ser Trp
                 85                  90                  95

Pro Leu Ser Ser Ser Val Pro Ser Gln Lys Thr Ala Ala Ala Leu Leu
            100                 105                 110

Ala Val Ala
        115


<210> SEQ ID NO 45
<211> LENGTH: 1257
<212> TYPE: DNA
<213> ORGANISM: Artificial Sequence
<220> FEATURE:
<223> OTHER INFORMATION: His-NLS-p53 cDNA Sequence

<400> SEQUENCE: 45

atgggcagca gccatcatca tcatcatcac agcagcggcc tggtgccgcg cggcagccat     60

atgaagaaga agaggaagga ggagccgcag tcagatccta gcgtcgagcc ccctctgagt    120

caggaaacat tttcagacct atggaaacta cttcctgaaa acaacgttct gtcccccttg    180

ccgtcccaag caatggatga tttgatgctg tccccggacg atattgaaca atggttcact    240

gaagacccag gtccagatga agctcccaga atgccagagg ctgctccccg cgtggcccct    300

gcaccagcag ctcctacacc ggcggcccct gcaccagccc cctcctggcc cctgtcatct    360

tctgtccctt cccagaaaac ctaccagggc agctacggtt tccgtctggg cttcttgcat    420

tctgggacag ccaagtctgt gacttgcacg tactcccctg ccctcaacaa gatgttttgc    480
```

```
caactggcca agacctgccc tgtgcagctg tgggttgatt ccacaccccc gcccggcacc    540

cgcgtccgcg ccatggccat ctacaagcag tcacagcaca tgacggaggt tgtgaggcgc    600

tgcccccacc atgagcgctg ctcagatagc gatggtctgg cccctcctca gcatcttatc    660

cgagtggaag gaaatttgcg tgtggagtat ttggatgaca gaaacacttt tcgacatagt    720

gtggtggtgc cctatgagcc gcctgaggtt ggctctgact gtaccaccat ccactacaac    780

tacatgtgta acagttcctg catgggcggc atgaaccgga ggcccatcct caccatcatc    840

acactggaag actccagtgg taatctactg ggacggaaca gctttgaggt gcgtgtttgt    900

gcctgtcctg ggagagaccg gcgcacagag gaagagaatc tccgcaagaa aggggagcct    960

caccacgagc tgcccccagg gagcactaag cgagcactgc ccaacaacac cagctcctct   1020

ccccagccaa agaagaaacc actggatgga ggatatttca cccttcagat ccgtgggcgt   1080

gagcgcttcg agatgttccg agagctgatt gaggccttgg aactcaagga tgcccaggct   1140

gggaaggagc caggggggag cagggctcac tccagccacc tgaagtccaa aaagggtcag   1200

tctacctccc gccataaaaa actcatgttc aagacagaag ggcctgactc agactga      1257
```

<210> SEQ ID NO 46
<211> LENGTH: 418
<212> TYPE: PRT
<213> ORGANISM: Artificial Sequence
<220> FEATURE:
<223> OTHER INFORMATION: His-NLS-p53 Amino Acid Sequence

<400> SEQUENCE: 46

```
Met Gly Ser Ser His His His His His His Ser Ser Gly Leu Val Pro
  1               5                  10                  15

Arg Gly Ser His Met Lys Lys Lys Arg Lys Glu Glu Pro Gln Ser Asp
             20                  25                  30

Pro Ser Val Glu Pro Pro Leu Ser Gln Glu Thr Phe Ser Asp Leu Trp
         35                  40                  45

Lys Leu Leu Pro Glu Asn Asn Val Leu Ser Pro Leu Pro Ser Gln Ala
     50                  55                  60

Met Asp Asp Leu Met Leu Ser Pro Asp Asp Ile Glu Gln Trp Phe Thr
 65                  70                  75                  80

Glu Asp Pro Gly Pro Asp Glu Ala Pro Arg Met Pro Glu Ala Ala Pro
                 85                  90                  95

Arg Val Ala Pro Ala Pro Ala Ala Pro Thr Pro Ala Ala Pro Ala Pro
            100                 105                 110

Ala Pro Ser Trp Pro Leu Ser Ser Ser Val Pro Ser Gln Lys Thr Tyr
        115                 120                 125

Gln Gly Ser Tyr Gly Phe Arg Leu Gly Phe Leu His Ser Gly Thr Ala
    130                 135                 140

Lys Ser Val Thr Cys Thr Tyr Ser Pro Ala Leu Asn Lys Met Phe Cys
145                 150                 155                 160

Gln Leu Ala Lys Thr Cys Pro Val Gln Leu Trp Val Asp Ser Thr Pro
                165                 170                 175

Pro Pro Gly Thr Arg Val Arg Ala Met Ala Ile Tyr Lys Gln Ser Gln
            180                 185                 190

His Met Thr Glu Val Val Arg Arg Cys Pro His His Glu Arg Cys Ser
        195                 200                 205

Asp Ser Asp Gly Leu Ala Pro Pro Gln His Leu Ile Arg Val Glu Gly
    210                 215                 220

Asn Leu Arg Val Glu Tyr Leu Asp Asp Arg Asn Thr Phe Arg His Ser
```

```
225                 230                 235                 240

Val Val Val Pro Tyr Glu Pro Pro Glu Val Gly Ser Asp Cys Thr Thr
                245                 250                 255

Ile His Tyr Asn Tyr Met Cys Asn Ser Ser Cys Met Gly Gly Met Asn
            260                 265                 270

Arg Arg Pro Ile Leu Thr Ile Ile Thr Leu Glu Asp Ser Ser Gly Asn
        275                 280                 285

Leu Leu Gly Arg Asn Ser Phe Glu Val Arg Val Cys Ala Cys Pro Gly
    290                 295                 300

Arg Asp Arg Arg Thr Glu Glu Glu Asn Leu Arg Lys Lys Gly Glu Pro
305                 310                 315                 320

His His Glu Leu Pro Pro Gly Ser Thr Lys Arg Ala Leu Pro Asn Asn
                325                 330                 335

Thr Ser Ser Ser Pro Gln Pro Lys Lys Lys Pro Leu Asp Gly Gly Tyr
            340                 345                 350

Phe Thr Leu Gln Ile Arg Gly Arg Glu Arg Phe Glu Met Phe Arg Glu
        355                 360                 365

Leu Ile Glu Ala Leu Glu Leu Lys Asp Ala Gln Ala Gly Lys Glu Pro
    370                 375                 380

Gly Gly Ser Arg Ala His Ser Ser His Leu Lys Ser Lys Lys Gly Gln
385                 390                 395                 400

Ser Thr Ser Arg His Lys Lys Leu Met Phe Lys Thr Glu Gly Pro Asp
                405                 410                 415

Ser Asp


<210> SEQ ID NO 47
<211> LENGTH: 1287
<212> TYPE: DNA
<213> ORGANISM: Artificial Sequence
<220> FEATURE:
<223> OTHER INFORMATION: His-NLS-JO-39 MTD- p53 cDNA Sequence

<400> SEQUENCE: 47

atgggcagca gccatcatca tcatcatcac agcagcggcc tggtgccgcg cggcagccat      60

atgaagaaga agaggaagcc gctggtgctg gcgattgcgg cggtgctgga ggagccgcag     120

tcagatccta gcgtcgagcc ccctctgagt caggaaacat tttcagacct atggaaacta     180

cttcctgaaa acaacgttct gtcccccttg ccgtcccaag caatggatga tttgatgctg     240

tccccggacg atattgaaca atggttcact gaagacccag gtccagatga agctcccaga     300

atgccagagg ctgctccccg cgtggcccct gcaccagcag ctcctacacc ggcggcccct     360

gcaccagccc cctcctggcc cctgtcatct tctgtccctt cccagaaaac ctaccagggc     420

agctacggtt tccgtctggg cttcttgcat tctgggacag ccaagtctgt gacttgcacg     480

tactcccctg ccctcaacaa gatgttttgc caactggcca agacctgccc tgtgcagctg     540

tgggttgatt ccacaccccc gcccggcacc cgcgtccgcg ccatggccat ctacaagcag     600

tcacagcaca tgacggaggt tgtgaggcgc tgcccccacc atgagcgctg ctcagatagc     660

gatggtctgg cccctcctca gcatcttatc cgagtggaag gaaatttgcg tgtggagtat     720

ttggatgaca gaaacacttt tcgacatagt gtggtggtgc cctatgagcc gcctgaggtt     780

ggctctgact gtaccaccat ccactacaac tacatgtgta acagttcctg catgggcggc     840

atgaaccgga ggcccatcct caccatcatc acactggaag actccagtgg taatctactg     900

ggacggaaca gctttgaggt gcgtgtttgt gcctgtcctg ggagagaccg gcgcacagag     960

gaagagaatc tccgcaagaa aggggagcct caccacgagc tgcccccagg gagcactaag    1020
```

```
cgagcactgc ccaacaacac cagctcctct ccccagccaa agaagaaacc actggatgga   1080

ggatatttca cccttcagat ccgtgggcgt gagcgcttcg agatgttccg agagctgatt   1140

gaggccttgg aactcaagga tgcccaggct gggaaggagc caggggggag cagggctcac   1200

tccagccacc tgaagtccaa aaagggtcag tctacctccc gccataaaaa actcatgttc   1260

aagacagaag ggcctgactc agactga                                       1287
```

<210> SEQ ID NO 48
<211> LENGTH: 428
<212> TYPE: PRT
<213> ORGANISM: Artificial Sequence
<220> FEATURE:
<223> OTHER INFORMATION: His-NLS-JO-39 MTD p53 Amino Acid Sequence

<400> SEQUENCE: 48

```
Met Gly Ser Ser His His His His His His Ser Ser Gly Leu Val Pro
  1               5                  10                  15

Arg Gly Ser His Met Lys Lys Lys Arg Lys Pro Leu Val Leu Ala Ile
             20                  25                  30

Ala Ala Val Leu Glu Glu Pro Gln Ser Asp Pro Ser Val Glu Pro Pro
        35                  40                  45

Leu Ser Gln Glu Thr Phe Ser Asp Leu Trp Lys Leu Leu Pro Glu Asn
     50                  55                  60

Asn Val Leu Ser Pro Leu Pro Ser Gln Ala Met Asp Asp Leu Met Leu
 65                  70                  75                  80

Ser Pro Asp Asp Ile Glu Gln Trp Phe Thr Glu Asp Pro Gly Pro Asp
                 85                  90                  95

Glu Ala Pro Arg Met Pro Glu Ala Ala Pro Arg Val Ala Pro Ala Pro
            100                 105                 110

Ala Ala Pro Thr Pro Ala Ala Pro Ala Pro Ala Pro Ser Trp Pro Leu
        115                 120                 125

Ser Ser Ser Val Pro Ser Gln Lys Thr Tyr Gln Gly Ser Tyr Gly Phe
    130                 135                 140

Arg Leu Gly Phe Leu His Ser Gly Thr Ala Lys Ser Val Thr Cys Thr
145                 150                 155                 160

Tyr Ser Pro Ala Leu Asn Lys Met Phe Cys Gln Leu Ala Lys Thr Cys
                165                 170                 175

Pro Val Gln Leu Trp Val Asp Ser Thr Pro Pro Pro Gly Thr Arg Val
            180                 185                 190

Arg Ala Met Ala Ile Tyr Lys Gln Ser Gln His Met Thr Glu Val Val
        195                 200                 205

Arg Arg Cys Pro His His Glu Arg Cys Ser Asp Ser Asp Gly Leu Ala
    210                 215                 220

Pro Pro Gln His Leu Ile Arg Val Glu Gly Asn Leu Arg Val Glu Tyr
225                 230                 235                 240

Leu Asp Asp Arg Asn Thr Phe Arg His Ser Val Val Val Pro Tyr Glu
                245                 250                 255

Pro Pro Glu Val Gly Ser Asp Cys Thr Thr Ile His Tyr Asn Tyr Met
            260                 265                 270

Cys Asn Ser Ser Cys Met Gly Gly Met Asn Arg Arg Pro Ile Leu Thr
        275                 280                 285

Ile Ile Thr Leu Glu Asp Ser Ser Gly Asn Leu Leu Gly Arg Asn Ser
    290                 295                 300

Phe Glu Val Arg Val Cys Ala Cys Pro Gly Arg Asp Arg Arg Thr Glu
305                 310                 315                 320
```

```
Glu Glu Asn Leu Arg Lys Lys Gly Glu Pro His His Glu Leu Pro Pro
                325                 330                 335

Gly Ser Thr Lys Arg Ala Leu Pro Asn Asn Thr Ser Ser Ser Pro Gln
            340                 345                 350

Pro Lys Lys Lys Pro Leu Asp Gly Gly Tyr Phe Thr Leu Gln Ile Arg
        355                 360                 365

Gly Arg Glu Arg Phe Glu Met Phe Arg Glu Leu Ile Glu Ala Leu Glu
    370                 375                 380

Leu Lys Asp Ala Gln Ala Gly Lys Glu Pro Gly Gly Ser Arg Ala His
385                 390                 395                 400

Ser Ser His Leu Lys Ser Lys Lys Gly Gln Ser Thr Ser Arg His Lys
                405                 410                 415

Lys Leu Met Phe Lys Thr Glu Gly Pro Asp Ser Asp
            420                 425
```

<210> SEQ ID NO 49
<211> LENGTH: 1287
<212> TYPE: DNA
<213> ORGANISM: Artificial Sequence
<220> FEATURE:
<223> OTHER INFORMATION: His-NLS-p53-JO-39 MTD cDNA Sequence

<400> SEQUENCE: 49

```
atgggcagca gccatcatca tcatcatcac agcagcggcc tggtgccgcg cggcagccat      60

atgaagaaga agaggaagga ggagccgcag tcagatccta gcgtcgagcc ccctctgagt     120

caggaaacat tttcagacct atggaaacta cttcctgaaa acaacgttct gtcccccttg     180

ccgtcccaag caatggatga tttgatgctg tccccggacg atattgaaca atggttcact     240

gaagacccag gtccagatga agctcccaga atgccagagg ctgctccccg cgtggcccct     300

gcaccagcag ctcctacacc ggcggcccct gcaccagccc cctcctggcc cctgtcatct     360

tctgtccctt cccagaaaac ctaccagggc agctacggtt tccgtctggg cttcttgcat     420

tctgggacag ccaagtctgt gacttgcacg tactcccctg ccctcaacaa gatgttttgc     480

caactggcca agacctgccc tgtgcagctg tgggttgatt ccacaccccc gcccggcacc     540

cgcgtccgcg ccatggccat ctacaagcag tcacagcaca tgacggaggt tgtgaggcgc     600

tgcccccacc atgagcgctg ctcagatagc gatggtctgg cccctcctca gcatcttatc     660

cgagtggaag gaaatttgcg tgtggagtat ttggatgaca gaaacacttt tcgacatagt     720

gtggtggtgc cctatgagcc gcctgaggtt ggctctgact gtaccaccat ccactacaac     780

tacatgtgta acagttcctg catgggcggc atgaaccgga ggcccatcct caccatcatc     840

acactggaag actccagtgg taatctactg ggacggaaca gctttgaggt gcgtgtttgt     900

gcctgtcctg ggagagaccg gcgcacagag gaagagaatc tccgcaagaa aggggagcct     960

caccacgagc tgcccccagg gagcactaag cgagcactgc ccaacaacac cagctcctct    1020

ccccagccaa agaagaaacc actggatgga ggatatttca cccttcagat ccgtgggcgt    1080

gagcgcttcg agatgttccg agagctgatt gaggccttgg aactcaagga tgcccaggct    1140

gggaaggagc caggggggag cagggctcac tccagccacc tgaagtccaa aaagggtcag    1200

tctacctccc gccataaaaa actcatgttc aagacagaag ggcctgactc agacccgctg    1260

gtgctggcga ttgcggcggt gctgtga                                        1287
```

<210> SEQ ID NO 50
<211> LENGTH: 428
<212> TYPE: PRT

```
<213> ORGANISM: Artificial Sequence
<220> FEATURE:
<223> OTHER INFORMATION: His-NLS-p53-JO-39 MTD Amino Acid Sequence

<400> SEQUENCE: 50

Met Gly Ser Ser His His His His His His Ser Ser Gly Leu Val Pro
1               5                   10                  15

Arg Gly Ser His Met Lys Lys Lys Arg Lys Glu Glu Pro Gln Ser Asp
            20                  25                  30

Pro Ser Val Glu Pro Pro Leu Ser Gln Glu Thr Phe Ser Asp Leu Trp
        35                  40                  45

Lys Leu Leu Pro Glu Asn Asn Val Leu Ser Pro Leu Pro Ser Gln Ala
    50                  55                  60

Met Asp Asp Leu Met Leu Ser Pro Asp Asp Ile Glu Gln Trp Phe Thr
65                  70                  75                  80

Glu Asp Pro Gly Pro Asp Glu Ala Pro Arg Met Pro Glu Ala Ala Pro
                85                  90                  95

Arg Val Ala Pro Ala Pro Ala Ala Pro Thr Pro Ala Ala Pro Ala Pro
            100                 105                 110

Ala Pro Ser Trp Pro Leu Ser Ser Ser Val Pro Ser Gln Lys Thr Tyr
        115                 120                 125

Gln Gly Ser Tyr Gly Phe Arg Leu Gly Phe Leu His Ser Gly Thr Ala
    130                 135                 140

Lys Ser Val Thr Cys Thr Tyr Ser Pro Ala Leu Asn Lys Met Phe Cys
145                 150                 155                 160

Gln Leu Ala Lys Thr Cys Pro Val Gln Leu Trp Val Asp Ser Thr Pro
                165                 170                 175

Pro Pro Gly Thr Arg Val Arg Ala Met Ala Ile Tyr Lys Gln Ser Gln
            180                 185                 190

His Met Thr Glu Val Val Arg Arg Cys Pro His His Glu Arg Cys Ser
        195                 200                 205

Asp Ser Asp Gly Leu Ala Pro Pro Gln His Leu Ile Arg Val Glu Gly
    210                 215                 220

Asn Leu Arg Val Glu Tyr Leu Asp Asp Arg Asn Thr Phe Arg His Ser
225                 230                 235                 240

Val Val Val Pro Tyr Glu Pro Pro Glu Val Gly Ser Asp Cys Thr Thr
                245                 250                 255

Ile His Tyr Asn Tyr Met Cys Asn Ser Ser Cys Met Gly Gly Met Asn
            260                 265                 270

Arg Arg Pro Ile Leu Thr Ile Ile Thr Leu Glu Asp Ser Ser Gly Asn
        275                 280                 285

Leu Leu Gly Arg Asn Ser Phe Glu Val Arg Val Cys Ala Cys Pro Gly
    290                 295                 300

Arg Asp Arg Arg Thr Glu Glu Glu Asn Leu Arg Lys Lys Gly Glu Pro
305                 310                 315                 320

His His Glu Leu Pro Pro Gly Ser Thr Lys Arg Ala Leu Pro Asn Asn
                325                 330                 335

Thr Ser Ser Ser Pro Gln Pro Lys Lys Lys Pro Leu Asp Gly Gly Tyr
            340                 345                 350

Phe Thr Leu Gln Ile Arg Gly Arg Glu Arg Phe Glu Met Phe Arg Glu
        355                 360                 365

Leu Ile Glu Ala Leu Glu Leu Lys Asp Ala Gln Ala Gly Lys Glu Pro
    370                 375                 380

Gly Gly Ser Arg Ala His Ser Ser His Leu Lys Ser Lys Lys Gly Gln
385                 390                 395                 400
```

```
Ser Thr Ser Arg His Lys Lys Leu Met Phe Lys Thr Glu Gly Pro Asp
                405                 410                 415

Ser Asp Pro Leu Val Leu Ala Ile Ala Ala Val Leu
            420                 425


<210> SEQ ID NO 51
<211> LENGTH: 1317
<212> TYPE: DNA
<213> ORGANISM: Artificial Sequence
<220> FEATURE:
<223> OTHER INFORMATION: His-NLS-JO-39 MTD-p53-JO-39 MTD cDNA Sequence

<400> SEQUENCE: 51

atgggcagca gccatcatca tcatcatcac agcagcggcc tggtgccgcg cggcagccat     60

atgaagaaga agaggaagcc gctggtgctg gcgattgcgg cggtgctgga ggagccgcag    120

tcagatccta gcgtcgagcc ccctctgagt caggaaacat tttcagacct atggaaacta    180

cttcctgaaa acaacgttct gtcccccttg ccgtcccaag caatggatga tttgatgctg    240

tccccggacg atattgaaca atggttcact gaagacccag gtccagatga agctcccaga    300

atgccagagg ctgctccccg cgtggcccct gcaccagcag ctcctacacc ggcggcccct    360

gcaccagccc cctcctggcc cctgtcatct tctgtccctt cccagaaaac ctaccagggc    420

agctacggtt tccgtctggg cttcttgcat tctgggacag ccaagtctgt gacttgcacg    480

tactcccctg ccctcaacaa gatgttttgc caactggcca agacctgccc tgtgcagctg    540

tgggttgatt ccacaccccc gcccggcacc cgcgtccgcg ccatggccat ctacaagcag    600

tcacagcaca tgacggaggt tgtgaggcgc tgcccccacc atgagcgctg ctcagatagc    660

gatggtctgg cccctcctca gcatcttatc cgagtggaag gaaatttgcg tgtggagtat    720

ttggatgaca gaaacacttt tcgacatagt gtggtggtgc cctatgagcc gcctgaggtt    780

ggctctgact gtaccaccat ccactacaac tacatgtgta acagttcctg catgggcggc    840

atgaaccgga ggcccatcct caccatcatc acactggaag actccagtgg taatctactg    900

ggacggaaca gctttgaggt gcgtgtttgt gcctgtcctg ggagagaccg gcgcacagag    960

gaagagaatc tccgcaagaa aggggagcct caccacgagc tgcccccagg gagcactaag   1020

cgagcactgc ccaacaacac cagctcctct ccccagccaa agaagaaacc actggatgga   1080

ggatatttca cccttcagat ccgtgggcgt gagcgcttcg agatgttccg agagctgatt   1140

gaggccttgg aactcaagga tgcccaggct gggaaggagc caggggggag cagggctcac   1200

tccagccacc tgaagtccaa aaagggtcag tctacctccc gccataaaaa actcatgttc   1260

aagacagaag ggcctgactc agacccgctg gtgctggcga ttgcggcggt gctgtga      1317


<210> SEQ ID NO 52
<211> LENGTH: 438
<212> TYPE: PRT
<213> ORGANISM: Artificial Sequence
<220> FEATURE:
<223> OTHER INFORMATION: His-NLS-JO-39 MTD-p53-JO-39 MTD Amino Acid
      Sequence

<400> SEQUENCE: 52

Met Gly Ser Ser His His His His His His Ser Ser Gly Leu Val Pro
  1               5                  10                  15

Arg Gly Ser His Met Lys Lys Lys Arg Lys Pro Leu Val Leu Ala Ile
             20                  25                  30

Ala Ala Val Leu Glu Glu Pro Gln Ser Asp Pro Ser Val Glu Pro Pro
         35                  40                  45
```

```
Leu Ser Gln Glu Thr Phe Ser Asp Leu Trp Lys Leu Leu Pro Glu Asn
    50                  55                  60

Asn Val Leu Ser Pro Leu Pro Ser Gln Ala Met Asp Asp Leu Met Leu
65                  70                  75                  80

Ser Pro Asp Asp Ile Glu Gln Trp Phe Thr Glu Asp Pro Gly Pro Asp
                85                  90                  95

Glu Ala Pro Arg Met Pro Glu Ala Ala Pro Arg Val Ala Pro Ala Pro
            100                 105                 110

Ala Ala Pro Thr Pro Ala Ala Pro Ala Pro Ala Pro Ser Trp Pro Leu
        115                 120                 125

Ser Ser Ser Val Pro Ser Gln Lys Thr Tyr Gln Gly Ser Tyr Gly Phe
    130                 135                 140

Arg Leu Gly Phe Leu His Ser Gly Thr Ala Lys Ser Val Thr Cys Thr
145                 150                 155                 160

Tyr Ser Pro Ala Leu Asn Lys Met Phe Cys Gln Leu Ala Lys Thr Cys
                165                 170                 175

Pro Val Gln Leu Trp Val Asp Ser Thr Pro Pro Pro Gly Thr Arg Val
            180                 185                 190

Arg Ala Met Ala Ile Tyr Lys Gln Ser Gln His Met Thr Glu Val Val
        195                 200                 205

Arg Arg Cys Pro His His Glu Arg Cys Ser Asp Ser Asp Gly Leu Ala
    210                 215                 220

Pro Pro Gln His Leu Ile Arg Val Glu Gly Asn Leu Arg Val Glu Tyr
225                 230                 235                 240

Leu Asp Asp Arg Asn Thr Phe Arg His Ser Val Val Val Pro Tyr Glu
                245                 250                 255

Pro Pro Glu Val Gly Ser Asp Cys Thr Thr Ile His Tyr Asn Tyr Met
            260                 265                 270

Cys Asn Ser Ser Cys Met Gly Gly Met Asn Arg Arg Pro Ile Leu Thr
        275                 280                 285

Ile Ile Thr Leu Glu Asp Ser Ser Gly Asn Leu Leu Gly Arg Asn Ser
    290                 295                 300

Phe Glu Val Arg Val Cys Ala Cys Pro Gly Arg Asp Arg Arg Thr Glu
305                 310                 315                 320

Glu Glu Asn Leu Arg Lys Lys Gly Glu Pro His His Glu Leu Pro Pro
                325                 330                 335

Gly Ser Thr Lys Arg Ala Leu Pro Asn Asn Thr Ser Ser Ser Pro Gln
            340                 345                 350

Pro Lys Lys Lys Pro Leu Asp Gly Gly Tyr Phe Thr Leu Gln Ile Arg
        355                 360                 365

Gly Arg Glu Arg Phe Glu Met Phe Arg Glu Leu Ile Glu Ala Leu Glu
    370                 375                 380

Leu Lys Asp Ala Gln Ala Gly Lys Glu Pro Gly Gly Ser Arg Ala His
385                 390                 395                 400

Ser Ser His Leu Lys Ser Lys Lys Gly Gln Ser Thr Ser Arg His Lys
                405                 410                 415

Lys Leu Met Phe Lys Thr Glu Gly Pro Asp Ser Asp Pro Leu Val Leu
            420                 425                 430

Ala Ile Ala Ala Val Leu
        435
```

<210> SEQ ID NO 53
<211> LENGTH: 1281
<212> TYPE: DNA

<213> ORGANISM: Artificial Sequence
<220> FEATURE:
<223> OTHER INFORMATION: His-NLS-JO-41 MTD-p53 cDNA Sequence

<400> SEQUENCE: 53

```
atgggcagca gccatcatca tcatcatcac agcagcggcc tggtgccgcg cggcagccat     60

atgaagaaga agaggaaggc ggcggcgctg ctggcggtgg cggaggagcc gcagtcagat    120

cctagcgtcg agccccctct gagtcaggaa acattttcag acctatggaa actacttcct    180

gaaaacaacg ttctgtcccc cttgccgtcc caagcaatgg atgatttgat gctgtccccg    240

gacgatattg aacaatggtt cactgaagac ccaggtccag atgaagctcc cagaatgcca    300

gaggctgctc cccgcgtggc ccctgcacca gcagctccta caccggcggc ccctgcacca    360

gcccctcct ggcccctgtc atcttctgtc ccttcccaga aaacctacca gggcagctac    420

ggtttccgtc tgggcttctt gcattctggg acagccaagt ctgtgacttg cacgtactcc    480

cctgccctca acaagatgtt ttgccaactg gccaagacct gccctgtgca gctgtgggtt    540

gattccacac ccccgcccgg cacccgcgtc cgcgccatgg ccatctacaa gcagtcacag    600

cacatgacgg aggttgtgag gcgctgcccc caccatgagc gctgctcaga tagcgatggt    660

ctggcccctc ctcagcatct tatccgagtg gaaggaaatt tgcgtgtgga gtatttggat    720

gacagaaaca cttttcgaca tagtgtggtg gtgccctatg agccgcctga ggttggctct    780

gactgtacca ccatccacta caactacatg tgtaacagtt cctgcatggg cggcatgaac    840

cggaggccca tcctcaccat catcacactg gaagactcca gtggtaatct actgggacgg    900

aacagctttg aggtgcgtgt ttgtgcctgt cctgggagag accggcgcac agaggaagag    960

aatctccgca agaaagggga gcctcaccac gagctgcccc cagggagcac taagcgagca   1020

ctgcccaaca acaccagctc ctctccccag ccaaagaaga aaccactgga tggaggatat   1080

ttcacccttc agatccgtgg gcgtgagcgc ttcgagatgt tccgagagct gattgaggcc   1140

ttggaactca aggatgccca ggctgggaag gagccagggg ggagcagggc tcactccagc   1200

cacctgaagt ccaaaaaggg tcagtctacc tcccgccata aaaaactcat gttcaagaca   1260

gaagggcctg actcagactg a                                              1281
```

<210> SEQ ID NO 54
<211> LENGTH: 426
<212> TYPE: PRT
<213> ORGANISM: Artificial Sequence
<220> FEATURE:
<223> OTHER INFORMATION: His-NLS-JO-41 MTD-p53 Amino Acid Sequence

<400> SEQUENCE: 54

```
Met Gly Ser Ser His His His His His His Ser Ser Gly Leu Val Pro
  1               5                  10                  15

Arg Gly Ser His Met Lys Lys Lys Arg Lys Ala Ala Ala Leu Leu Ala
             20                  25                  30

Val Ala Glu Glu Pro Gln Ser Asp Pro Ser Val Glu Pro Pro Leu Ser
         35                  40                  45

Gln Glu Thr Phe Ser Asp Leu Trp Lys Leu Leu Pro Glu Asn Asn Val
     50                  55                  60

Leu Ser Pro Leu Pro Ser Gln Ala Met Asp Asp Leu Met Leu Ser Pro
 65                  70                  75                  80

Asp Asp Ile Glu Gln Trp Phe Thr Glu Asp Pro Gly Pro Asp Glu Ala
                 85                  90                  95

Pro Arg Met Pro Glu Ala Ala Pro Arg Val Ala Pro Ala Pro Ala Ala
            100                 105                 110
```

```
Pro Thr Pro Ala Ala Pro Ala Pro Ala Pro Ser Trp Pro Leu Ser Ser
        115                 120                 125

Ser Val Pro Ser Gln Lys Thr Tyr Gln Gly Ser Tyr Gly Phe Arg Leu
    130                 135                 140

Gly Phe Leu His Ser Gly Thr Ala Lys Ser Val Thr Cys Thr Tyr Ser
145                 150                 155                 160

Pro Ala Leu Asn Lys Met Phe Cys Gln Leu Ala Lys Thr Cys Pro Val
                165                 170                 175

Gln Leu Trp Val Asp Ser Thr Pro Pro Pro Gly Thr Arg Val Arg Ala
            180                 185                 190

Met Ala Ile Tyr Lys Gln Ser Gln His Met Thr Glu Val Val Arg Arg
        195                 200                 205

Cys Pro His His Glu Arg Cys Ser Asp Ser Asp Gly Leu Ala Pro Pro
    210                 215                 220

Gln His Leu Ile Arg Val Glu Gly Asn Leu Arg Val Glu Tyr Leu Asp
225                 230                 235                 240

Asp Arg Asn Thr Phe Arg His Ser Val Val Val Pro Tyr Glu Pro Pro
                245                 250                 255

Glu Val Gly Ser Asp Cys Thr Thr Ile His Tyr Asn Tyr Met Cys Asn
            260                 265                 270

Ser Ser Cys Met Gly Gly Met Asn Arg Arg Pro Ile Leu Thr Ile Ile
        275                 280                 285

Thr Leu Glu Asp Ser Ser Gly Asn Leu Leu Gly Arg Asn Ser Phe Glu
    290                 295                 300

Val Arg Val Cys Ala Cys Pro Gly Arg Asp Arg Arg Thr Glu Glu Glu
305                 310                 315                 320

Asn Leu Arg Lys Lys Gly Glu Pro His His Glu Leu Pro Pro Gly Ser
                325                 330                 335

Thr Lys Arg Ala Leu Pro Asn Asn Thr Ser Ser Ser Pro Gln Pro Lys
            340                 345                 350

Lys Lys Pro Leu Asp Gly Gly Tyr Phe Thr Leu Gln Ile Arg Gly Arg
        355                 360                 365

Glu Arg Phe Glu Met Phe Arg Glu Leu Ile Glu Ala Leu Glu Leu Lys
    370                 375                 380

Asp Ala Gln Ala Gly Lys Glu Pro Gly Gly Ser Arg Ala His Ser Ser
385                 390                 395                 400

His Leu Lys Ser Lys Lys Gly Gln Ser Thr Ser Arg His Lys Lys Leu
                405                 410                 415

Met Phe Lys Thr Glu Gly Pro Asp Ser Asp
            420                 425
```

<210> SEQ ID NO 55
<211> LENGTH: 1281
<212> TYPE: DNA
<213> ORGANISM: Artificial Sequence
<220> FEATURE:
<223> OTHER INFORMATION: His-NLS-p53-JO-41 MTD cDNA Sequence

<400> SEQUENCE: 55

```
atgggcagca gccatcatca tcatcatcac agcagcggcc tggtgccgcg cggcagccat     60

atgaagaaga agaggaagga ggagccgcag tcagatccta gcgtcgagcc ccctctgagt    120

caggaaacat tttcagacct atggaaacta cttcctgaaa acaacgttct gtcccccttg    180

ccgtcccaag caatggatga tttgatgctg tccccggacg atattgaaca atggttcact    240

gaagacccag gtccagatga agctcccaga atgccagagg ctgctccccg cgtggcccct    300
```

```
gcaccagcag ctcctacacc ggcggcccct gcaccagccc cctcctggcc cctgtcatct    360

tctgtccctt cccagaaaac ctaccagggc agctacggtt tccgtctggg cttcttgcat    420

tctgggacag ccaagtctgt gacttgcacg tactcccctg ccctcaacaa gatgttttgc    480

caactggcca agacctgccc tgtgcagctg tgggttgatt ccacaccccc gcccggcacc    540

cgcgtccgcg ccatggccat ctacaagcag tcacagcaca tgacggaggt tgtgaggcgc    600

tgcccccacc atgagcgctg ctcagatagc gatggtctgg cccctcctca gcatcttatc    660

cgagtggaag gaaatttgcg tgtggagtat ttggatgaca gaaacacttt tcgacatagt    720

gtggtggtgc cctatgagcc gcctgaggtt ggctctgact gtaccaccat ccactacaac    780

tacatgtgta acagttcctg catgggcggc atgaaccgga ggcccatcct caccatcatc    840

acactggaag actccagtgg taatctactg ggacggaaca gctttgaggt gcgtgtttgt    900

gcctgtcctg ggagagaccg gcgcacagag gaagagaatc tccgcaagaa aggggagcct    960

caccacgagc tgcccccagg gagcactaag cgagcactgc ccaacaacac cagctcctct   1020

ccccagccaa agaagaaacc actggatgga ggatatttca cccttcagat ccgtgggcgt   1080

gagcgcttcg agatgttccg agagctgatt gaggccttgg aactcaagga tgcccaggct   1140

gggaaggagc caggggggag cagggctcac tccagccacc tgaagtccaa aaagggtcag   1200

tctacctccc gccataaaaa actcatgttc aagacagaag ggcctgactc agacgcggcg   1260

gcgctgctgg cggtggcgtg a                                              1281
```

<210> SEQ ID NO 56
<211> LENGTH: 426
<212> TYPE: PRT
<213> ORGANISM: Artificial Sequence
<220> FEATURE:
<223> OTHER INFORMATION: His-NLS-p53-JO-41 MTD Amino Acid Sequence

<400> SEQUENCE: 56

```
Met Gly Ser Ser His His His His His His Ser Ser Gly Leu Val Pro
  1               5                  10                  15

Arg Gly Ser His Met Lys Lys Lys Arg Lys Glu Glu Pro Gln Ser Asp
             20                  25                  30

Pro Ser Val Glu Pro Pro Leu Ser Gln Glu Thr Phe Ser Asp Leu Trp
         35                  40                  45

Lys Leu Leu Pro Glu Asn Asn Val Leu Ser Pro Leu Pro Ser Gln Ala
     50                  55                  60

Met Asp Asp Leu Met Leu Ser Pro Asp Asp Ile Glu Gln Trp Phe Thr
 65                  70                  75                  80

Glu Asp Pro Gly Pro Asp Glu Ala Pro Arg Met Pro Glu Ala Ala Pro
                 85                  90                  95

Arg Val Ala Pro Ala Pro Ala Ala Pro Thr Pro Ala Ala Pro Ala Pro
            100                 105                 110

Ala Pro Ser Trp Pro Leu Ser Ser Ser Val Pro Ser Gln Lys Thr Tyr
        115                 120                 125

Gln Gly Ser Tyr Gly Phe Arg Leu Gly Phe Leu His Ser Gly Thr Ala
    130                 135                 140

Lys Ser Val Thr Cys Thr Tyr Ser Pro Ala Leu Asn Lys Met Phe Cys
145                 150                 155                 160

Gln Leu Ala Lys Thr Cys Pro Val Gln Leu Trp Val Asp Ser Thr Pro
                165                 170                 175

Pro Pro Gly Thr Arg Val Arg Ala Met Ala Ile Tyr Lys Gln Ser Gln
            180                 185                 190
```

```
His Met Thr Glu Val Val Arg Arg Cys Pro His His Glu Arg Cys Ser
        195                 200                 205

Asp Ser Asp Gly Leu Ala Pro Pro Gln His Leu Ile Arg Val Glu Gly
    210                 215                 220

Asn Leu Arg Val Glu Tyr Leu Asp Asp Arg Asn Thr Phe Arg His Ser
225                 230                 235                 240

Val Val Val Pro Tyr Glu Pro Pro Glu Val Gly Ser Asp Cys Thr Thr
                245                 250                 255

Ile His Tyr Asn Tyr Met Cys Asn Ser Ser Cys Met Gly Gly Met Asn
            260                 265                 270

Arg Arg Pro Ile Leu Thr Ile Ile Thr Leu Glu Asp Ser Ser Gly Asn
        275                 280                 285

Leu Leu Gly Arg Asn Ser Phe Glu Val Arg Val Cys Ala Cys Pro Gly
    290                 295                 300

Arg Asp Arg Arg Thr Glu Glu Glu Asn Leu Arg Lys Lys Gly Glu Pro
305                 310                 315                 320

His His Glu Leu Pro Pro Gly Ser Thr Lys Arg Ala Leu Pro Asn Asn
                325                 330                 335

Thr Ser Ser Ser Pro Gln Pro Lys Lys Lys Pro Leu Asp Gly Gly Tyr
            340                 345                 350

Phe Thr Leu Gln Ile Arg Gly Arg Glu Arg Phe Glu Met Phe Arg Glu
        355                 360                 365

Leu Ile Glu Ala Leu Glu Leu Lys Asp Ala Gln Ala Gly Lys Glu Pro
    370                 375                 380

Gly Gly Ser Arg Ala His Ser Ser His Leu Lys Ser Lys Lys Gly Gln
385                 390                 395                 400

Ser Thr Ser Arg His Lys Lys Leu Met Phe Lys Thr Glu Gly Pro Asp
                405                 410                 415

Ser Asp Ala Ala Ala Leu Leu Ala Val Ala
            420                 425


<210> SEQ ID NO 57
<211> LENGTH: 1305
<212> TYPE: DNA
<213> ORGANISM: Artificial Sequence
<220> FEATURE:
<223> OTHER INFORMATION: His-NLS-JO-41 MTD-p53- JO-41 MTD cDNA Sequence

<400> SEQUENCE: 57

atgggcagca gccatcatca tcatcatcac agcagcggcc tggtgccgcg cggcagccat     60

atgaagaaga agaggaaggc ggcggcgctg ctggcggtgg cggaggagcc gcagtcagat    120

cctagcgtcg agccccctct gagtcaggaa acattttcag acctatggaa actacttcct    180

gaaaacaacg ttctgtcccc cttgccgtcc caagcaatgg atgatttgat gctgtccccg    240

gacgatattg aacaatggtt cactgaagac ccaggtccag atgaagctcc cagaatgcca    300

gaggctgctc cccgcgtggc ccctgcacca gcagctccta caccggcggc ccctgcacca    360

gcccccctcct ggcccctgtc atcttctgtc ccttcccaga aaacctacca gggcagctac    420

ggtttccgtc tgggcttctt gcattctggg acagccaagt ctgtgacttg cacgtactcc    480

cctgccctca acaagatgtt ttgccaactg gccaagacct gccctgtgca gctgtgggtt    540

gattccacac ccccgcccgg cacccgcgtc cgcgccatgg ccatctacaa gcagtcacag    600

cacatgacgg aggttgtgag gcgctgcccc caccatgagc gctgctcaga tagcgatggt    660

ctggcccctc ctcagcatct tatccgagtg gaaggaaatt tgcgtgtgga gtatttggat    720
```

```
gacagaaaca cttttcgaca tagtgtggtg gtgccctatg agccgcctga ggttggctct    780

gactgtacca ccatccacta caactacatg tgtaacagtt cctgcatggg cggcatgaac    840

cggaggccca tcctcaccat catcacactg gaagactcca gtggtaatct actgggacgg    900

aacagctttg aggtgcgtgt ttgtgcctgt cctgggagag accggcgcac agaggaagag    960

aatctccgca agaaagggga gcctcaccac gagctgcccc cagggagcac taagcgagca   1020

ctgcccaaca acaccagctc ctctccccag ccaaagaaga aaccactgga tggaggatat   1080

ttcacccttc agatccgtgg gcgtgagcgc ttcgagatgt tccgagagct gattgaggcc   1140

ttggaactca aggatgccca ggctgggaag gagccagggg ggagcagggc tcactccagc   1200

cacctgaagt ccaaaaaggg tcagtctacc tcccgccata aaaaactcat gttcaagaca   1260

gaagggcctg actcagacgc ggcggcgctg ctggcggtgg cgtga                   1305
```

<210> SEQ ID NO 58
<211> LENGTH: 434
<212> TYPE: PRT
<213> ORGANISM: Artificial Sequence
<220> FEATURE:
<223> OTHER INFORMATION: His-NLS-JO-41 MTD-p53-JO-41 MTD Amino Acid Sequence

<400> SEQUENCE: 58

```
Met Gly Ser Ser His His His His His His Ser Ser Gly Leu Val Pro
  1               5                  10                  15

Arg Gly Ser His Met Lys Lys Lys Arg Lys Ala Ala Ala Leu Leu Ala
             20                  25                  30

Val Ala Glu Glu Pro Gln Ser Asp Pro Ser Val Glu Pro Pro Leu Ser
         35                  40                  45

Gln Glu Thr Phe Ser Asp Leu Trp Lys Leu Leu Pro Glu Asn Asn Val
     50                  55                  60

Leu Ser Pro Leu Pro Ser Gln Ala Met Asp Asp Leu Met Leu Ser Pro
 65                  70                  75                  80

Asp Asp Ile Glu Gln Trp Phe Thr Glu Asp Pro Gly Pro Asp Glu Ala
                 85                  90                  95

Pro Arg Met Pro Glu Ala Ala Pro Arg Val Ala Pro Ala Pro Ala Ala
            100                 105                 110

Pro Thr Pro Ala Ala Pro Ala Pro Ala Pro Ser Trp Pro Leu Ser Ser
        115                 120                 125

Ser Val Pro Ser Gln Lys Thr Tyr Gln Gly Ser Tyr Gly Phe Arg Leu
    130                 135                 140

Gly Phe Leu His Ser Gly Thr Ala Lys Ser Val Thr Cys Thr Tyr Ser
145                 150                 155                 160

Pro Ala Leu Asn Lys Met Phe Cys Gln Leu Ala Lys Thr Cys Pro Val
                165                 170                 175

Gln Leu Trp Val Asp Ser Thr Pro Pro Pro Gly Thr Arg Val Arg Ala
            180                 185                 190

Met Ala Ile Tyr Lys Gln Ser Gln His Met Thr Glu Val Val Arg Arg
        195                 200                 205

Cys Pro His His Glu Arg Cys Ser Asp Ser Asp Gly Leu Ala Pro Pro
    210                 215                 220

Gln His Leu Ile Arg Val Glu Gly Asn Leu Arg Val Glu Tyr Leu Asp
225                 230                 235                 240

Asp Arg Asn Thr Phe Arg His Ser Val Val Val Pro Tyr Glu Pro Pro
                245                 250                 255

Glu Val Gly Ser Asp Cys Thr Thr Ile His Tyr Asn Tyr Met Cys Asn
```

```
        260                 265                 270

Ser Ser Cys Met Gly Gly Met Asn Arg Arg Pro Ile Leu Thr Ile Ile
        275                 280                 285

Thr Leu Glu Asp Ser Ser Gly Asn Leu Leu Gly Arg Asn Ser Phe Glu
    290                 295                 300

Val Arg Val Cys Ala Cys Pro Gly Arg Asp Arg Arg Thr Glu Glu Glu
305                 310                 315                 320

Asn Leu Arg Lys Lys Gly Glu Pro His His Glu Leu Pro Pro Gly Ser
                325                 330                 335

Thr Lys Arg Ala Leu Pro Asn Asn Thr Ser Ser Ser Pro Gln Pro Lys
            340                 345                 350

Lys Lys Pro Leu Asp Gly Gly Tyr Phe Thr Leu Gln Ile Arg Gly Arg
        355                 360                 365

Glu Arg Phe Glu Met Phe Arg Glu Leu Ile Glu Ala Leu Glu Leu Lys
    370                 375                 380

Asp Ala Gln Ala Gly Lys Glu Pro Gly Gly Ser Arg Ala His Ser Ser
385                 390                 395                 400

His Leu Lys Ser Lys Lys Gly Gln Ser Thr Ser Arg His Lys Lys Leu
                405                 410                 415

Met Phe Lys Thr Glu Gly Pro Asp Ser Asp Ala Ala Ala Leu Leu Ala
            420                 425                 430

Val Ala


<210> SEQ ID NO 59
<211> LENGTH: 369
<212> TYPE: DNA
<213> ORGANISM: Artificial Sequence
<220> FEATURE:
<223> OTHER INFORMATION: His-deltap53 cDNA Sequence

<400> SEQUENCE: 59

atgggcagca gccatcatca tcatcatcac agcagcggcc tggtgccgcg cggcagccat     60

atggaggagc cgcagtcaga tcctagcgtc gagccccctc tgagtcagga aacattttca    120

gacctatgga aactacttcc tgaaaacaac gttctgtccc ccttgccgtc ccaagcaatg    180

gatgatttga tgctgtcccc ggacgatatt gaacaatggt tcactgaaga cccaggtcca    240

gatgaagctc ccagaatgcc agaggctgct ccccgcgtgg cccctgcacc agcagctcct    300

acaccggcgg cccctgcacc agccccctcc tggcccctgt catcttctgt cccttcccag    360

aaaacctga                                                             369


<210> SEQ ID NO 60
<211> LENGTH: 122
<212> TYPE: PRT
<213> ORGANISM: Artificial Sequence
<220> FEATURE:
<223> OTHER INFORMATION: His-deltap53 Amino Acid Sequence

<400> SEQUENCE: 60

Met Gly Ser Ser His His His His His His Ser Ser Gly Leu Val Pro
  1               5                  10                  15

Arg Gly Ser His Met Glu Glu Pro Gln Ser Asp Pro Ser Val Glu Pro
             20                  25                  30

Pro Leu Ser Gln Glu Thr Phe Ser Asp Leu Trp Lys Leu Leu Pro Glu
         35                  40                  45

Asn Asn Val Leu Ser Pro Leu Pro Ser Gln Ala Met Asp Asp Leu Met
     50                  55                  60
```

```
Leu Ser Pro Asp Asp Ile Glu Gln Trp Phe Thr Glu Asp Pro Gly Pro
 65                  70                  75                  80

Asp Glu Ala Pro Arg Met Pro Glu Ala Ala Pro Arg Val Ala Pro Ala
                 85                  90                  95

Pro Ala Ala Pro Thr Pro Ala Ala Pro Ala Pro Ala Pro Ser Trp Pro
            100                 105                 110

Leu Ser Ser Ser Val Pro Ser Gln Lys Thr
        115                 120
```

<210> SEQ ID NO 61
<211> LENGTH: 384
<212> TYPE: DNA
<213> ORGANISM: Artificial Sequence
<220> FEATURE:
<223> OTHER INFORMATION: His-NLS-deltap53 cDNA Sequence

<400> SEQUENCE: 61

```
atgggcagca gccatcatca tcatcatcac agcagcggcc tggtgccgcg cggcagccat     60

atgaagaaga agaggaagga ggagccgcag tcagatccta gcgtcgagcc ccctctgagt    120

caggaaacat tttcagacct atggaaacta cttcctgaaa acaacgttct gtcccccttg    180

ccgtcccaag caatggatga tttgatgctg tccccggacg atattgaaca atggttcact    240

gaagacccag gtccagatga agctcccaga atgccagagg ctgctccccg cgtggcccct    300

gcaccagcag ctcctacacc ggcggcccct gcaccagccc cctcctggcc cctgtcatct    360

tctgtccctt cccagaaaac ctga                                           384
```

<210> SEQ ID NO 62
<211> LENGTH: 127
<212> TYPE: PRT
<213> ORGANISM: Artificial Sequence
<220> FEATURE:
<223> OTHER INFORMATION: His-NLS-deltap53 Amino Acid Sequence

<400> SEQUENCE: 62

```
Met Gly Ser Ser His His His His His His Ser Ser Gly Leu Val Pro
  1               5                  10                  15

Arg Gly Ser His Met Lys Lys Lys Arg Lys Glu Glu Pro Gln Ser Asp
            20                  25                  30

Pro Ser Val Glu Pro Pro Leu Ser Gln Glu Thr Phe Ser Asp Leu Trp
        35                  40                  45

Lys Leu Leu Pro Glu Asn Asn Val Leu Ser Pro Leu Pro Ser Gln Ala
     50                  55                  60

Met Asp Asp Leu Met Leu Ser Pro Asp Asp Ile Glu Gln Trp Phe Thr
 65                  70                  75                  80

Glu Asp Pro Gly Pro Asp Glu Ala Pro Arg Met Pro Glu Ala Ala Pro
                 85                  90                  95

Arg Val Ala Pro Ala Pro Ala Ala Pro Thr Pro Ala Ala Pro Ala Pro
            100                 105                 110

Ala Pro Ser Trp Pro Leu Ser Ser Ser Val Pro Ser Gln Lys Thr
        115                 120                 125
```

<210> SEQ ID NO 63
<211> LENGTH: 399
<212> TYPE: DNA
<213> ORGANISM: Artificial Sequence
<220> FEATURE:
<223> OTHER INFORMATION: His-JO-39 MTD-deltap53 cDNA Sequence

<400> SEQUENCE: 63

```
atgggcagca gccatcatca tcatcatcac agcagcggcc tggtgccgcg cggcagccat     60

atgccgctgg tgctggcgat tgcggcggtg ctggaggagc cgcagtcaga tcctagcgtc    120

gagccccctc tgagtcagga aacattttca gacctatgga aactacttcc tgaaaacaac    180

gttctgtccc ccttgccgtc ccaagcaatg gatgatttga tgctgtcccc ggacgatatt    240

gaacaatggt tcactgaaga cccaggtcca gatgaagctc ccagaatgcc agaggctgct    300

ccccgcgtgg cccctgcacc agcagctcct acaccggcgg cccctgcacc agccccctcc    360

tggcccctgt catcttctgt cccttcccag aaaacctga                           399
```

<210> SEQ ID NO 64
<211> LENGTH: 132
<212> TYPE: PRT
<213> ORGANISM: Artificial Sequence
<220> FEATURE:
<223> OTHER INFORMATION: His-JO-39 MTD-deltap53 Amino Acid Sequence

<400> SEQUENCE: 64

```
Met Gly Ser Ser His His His His His His Ser Ser Gly Leu Val Pro
  1               5                  10                  15

Arg Gly Ser His Met Pro Leu Val Leu Ala Ile Ala Ala Val Leu Glu
             20                  25                  30

Glu Pro Gln Ser Asp Pro Ser Val Glu Pro Pro Leu Ser Gln Glu Thr
         35                  40                  45

Phe Ser Asp Leu Trp Lys Leu Leu Pro Glu Asn Asn Val Leu Ser Pro
     50                  55                  60

Leu Pro Ser Gln Ala Met Asp Asp Leu Met Leu Ser Pro Asp Asp Ile
 65                  70                  75                  80

Glu Gln Trp Phe Thr Glu Asp Pro Gly Pro Asp Glu Ala Pro Arg Met
                 85                  90                  95

Pro Glu Ala Ala Pro Arg Val Ala Pro Ala Pro Ala Ala Pro Thr Pro
            100                 105                 110

Ala Ala Pro Ala Pro Ala Pro Ser Trp Pro Leu Ser Ser Ser Val Pro
        115                 120                 125

Ser Gln Lys Thr
    130
```

<210> SEQ ID NO 65
<211> LENGTH: 399
<212> TYPE: DNA
<213> ORGANISM: Artificial Sequence
<220> FEATURE:
<223> OTHER INFORMATION: His-deltap53-JO-39 MTD cDNA Sequence

<400> SEQUENCE: 65

```
atgggcagca gccatcatca tcatcatcac agcagcggcc tggtgccgcg cggcagccat     60

atggaggagc cgcagtcaga tcctagcgtc gagccccctc tgagtcagga aacattttca    120

gacctatgga aactacttcc tgaaaacaac gttctgtccc ccttgccgtc ccaagcaatg    180

gatgatttga tgctgtcccc ggacgatatt gaacaatggt tcactgaaga cccaggtcca    240

gatgaagctc ccagaatgcc agaggctgct ccccgcgtgg cccctgcacc agcagctcct    300

acaccggcgg cccctgcacc agccccctcc tggcccctgt catcttctgt cccttcccag    360

aaaaccccgc tggtgctggc gattgcggcg gtgctgtga                           399
```

<210> SEQ ID NO 66
<211> LENGTH: 132
<212> TYPE: PRT
<213> ORGANISM: Artificial Sequence
<220> FEATURE:
<223> OTHER INFORMATION: His-deltap53-JO-39 MTD Amino Acid Sequence

<400> SEQUENCE: 66

```
Met Gly Ser Ser His His His His His His Ser Ser Gly Leu Val Pro
  1               5                  10                  15

Arg Gly Ser His Met Glu Glu Pro Gln Ser Asp Pro Ser Val Glu Pro
             20                  25                  30

Pro Leu Ser Gln Glu Thr Phe Ser Asp Leu Trp Lys Leu Leu Pro Glu
         35                  40                  45

Asn Asn Val Leu Ser Pro Leu Pro Ser Gln Ala Met Asp Asp Leu Met
     50                  55                  60

Leu Ser Pro Asp Asp Ile Glu Gln Trp Phe Thr Glu Asp Pro Gly Pro
 65                  70                  75                  80

Asp Glu Ala Pro Arg Met Pro Glu Ala Ala Pro Arg Val Ala Pro Ala
                 85                  90                  95

Pro Ala Ala Pro Thr Pro Ala Ala Pro Ala Pro Ala Pro Ser Trp Pro
            100                 105                 110

Leu Ser Ser Ser Val Pro Ser Gln Lys Thr Pro Leu Val Leu Ala Ile
        115                 120                 125

Ala Ala Val Leu
    130
```

<210> SEQ ID NO 67
<211> LENGTH: 414
<212> TYPE: DNA
<213> ORGANISM: Artificial Sequence
<220> FEATURE:
<223> OTHER INFORMATION: His-NLS-JO-39 MTD-deltap53 cDNA Sequence

<400> SEQUENCE: 67

```
atgggcagca gccatcatca tcatcatcac agcagcggcc tggtgccgcg cggcagccat      60

atgaagaaga agaggaagcc gctggtgctg gcgattgcgg cggtgctgga ggagccgcag     120

tcagatccta gcgtcgagcc ccctctgagt caggaaacat tttcagacct atggaaacta     180

cttcctgaaa acaacgttct gtcccccttg ccgtcccaag caatggatga tttgatgctg     240

tccccggacg atattgaaca atggttcact gaagacccag gtccagatga agctcccaga     300

atgccagagg ctgctccccg cgtggcccct gcaccagcag ctcctacacc ggcggcccct     360

gcaccagccc cctcctggcc cctgtcatct tctgtccctt cccagaaaac ctga           414
```

<210> SEQ ID NO 68
<211> LENGTH: 137
<212> TYPE: PRT
<213> ORGANISM: Artificial Sequence
<220> FEATURE:
<223> OTHER INFORMATION: His-NLS-JO-39 MTD-deltap53 Amino Acid Sequence

<400> SEQUENCE: 68

```
Met Gly Ser Ser His His His His His His Ser Ser Gly Leu Val Pro
  1               5                  10                  15

Arg Gly Ser His Met Lys Lys Lys Arg Lys Pro Leu Val Leu Ala Ile
             20                  25                  30

Ala Ala Val Leu Glu Glu Pro Gln Ser Asp Pro Ser Val Glu Pro Pro
         35                  40                  45

Leu Ser Gln Glu Thr Phe Ser Asp Leu Trp Lys Leu Leu Pro Glu Asn
     50                  55                  60

Asn Val Leu Ser Pro Leu Pro Ser Gln Ala Met Asp Asp Leu Met Leu
 65                  70                  75                  80
```

```
Ser Pro Asp Asp Ile Glu Gln Trp Phe Thr Glu Asp Pro Gly Pro Asp
                85                  90                  95

Glu Ala Pro Arg Met Pro Glu Ala Ala Pro Arg Val Ala Pro Ala Pro
            100                 105                 110

Ala Ala Pro Thr Pro Ala Ala Pro Ala Pro Ala Pro Ser Trp Pro Leu
        115                 120                 125

Ser Ser Ser Val Pro Ser Gln Lys Thr
    130                 135


<210> SEQ ID NO 69
<211> LENGTH: 414
<212> TYPE: DNA
<213> ORGANISM: Artificial Sequence
<220> FEATURE:
<223> OTHER INFORMATION: His-NLS-deltap53-JO-39 MTD cDNA Sequence

<400> SEQUENCE: 69

atgggcagca gccatcatca tcatcatcac agcagcggcc tggtgccgcg cggcagccat      60

atgaagaaga agaggaagga ggagccgcag tcagatccta gcgtcgagcc ccctctgagt     120

caggaaacat tttcagacct atggaaacta cttcctgaaa acaacgttct gtcccccttg     180

ccgtcccaag caatggatga tttgatgctg tccccggacg atattgaaca atggttcact     240

gaagacccag gtccagatga agctcccaga atgccagagg ctgctccccg cgtggcccct     300

gcaccagcag ctcctacacc ggcggcccct gcaccagccc cctcctggcc cctgtcatct     360

tctgtccctt cccagaaaac ccgctggtg ctggcgattg cggcggtgct gtga            414


<210> SEQ ID NO 70
<211> LENGTH: 137
<212> TYPE: PRT
<213> ORGANISM: Artificial Sequence
<220> FEATURE:
<223> OTHER INFORMATION: His-NLS-deltap53-JO-39 MTD Amino Acid Sequence

<400> SEQUENCE: 70

Met Gly Ser Ser His His His His His His Ser Ser Gly Leu Val Pro
  1               5                  10                  15

Arg Gly Ser His Met Lys Lys Lys Arg Lys Glu Glu Pro Gln Ser Asp
            20                  25                  30

Pro Ser Val Glu Pro Pro Leu Ser Gln Glu Thr Phe Ser Asp Leu Trp
        35                  40                  45

Lys Leu Leu Pro Glu Asn Asn Val Leu Ser Pro Leu Pro Ser Gln Ala
     50                  55                  60

Met Asp Asp Leu Met Leu Ser Pro Asp Asp Ile Glu Gln Trp Phe Thr
 65                  70                  75                  80

Glu Asp Pro Gly Pro Asp Glu Ala Pro Arg Met Pro Glu Ala Ala Pro
                85                  90                  95

Arg Val Ala Pro Ala Pro Ala Ala Pro Thr Pro Ala Ala Pro Ala Pro
            100                 105                 110

Ala Pro Ser Trp Pro Leu Ser Ser Ser Val Pro Ser Gln Lys Thr Pro
        115                 120                 125

Leu Val Leu Ala Ile Ala Ala Val Leu
    130                 135


<210> SEQ ID NO 71
<211> LENGTH: 393
<212> TYPE: DNA
<213> ORGANISM: Artificial Sequence
<220> FEATURE:
```

<223> OTHER INFORMATION: His-JO-41 MTD-deltap53 cDNA Sequence

<400> SEQUENCE: 71

```
atgggcagca gccatcatca tcatcatcac agcagcggcc tggtgccgcg cggcagccat     60

atggcggcgg cgctgctggc ggtggcggag gagccgcagt cagatcctag cgtcgagccc    120

cctctgagtc aggaaacatt ttcagaccta tggaaactac ttcctgaaaa caacgttctg    180

tccccccttgc cgtcccaagc aatggatgat ttgatgctgt ccccggacga tattgaacaa   240

tggttcactg aagacccagg tccagatgaa gctcccagaa tgccagaggc tgctccccgc    300

gtggcccctg caccagcagc tcctacaccg gcggcccctg caccagcccc ctcctggccc    360

ctgtcatctt ctgtcccttc ccagaaaacc tga                                 393
```

<210> SEQ ID NO 72
<211> LENGTH: 130
<212> TYPE: PRT
<213> ORGANISM: Artificial Sequence
<220> FEATURE:
<223> OTHER INFORMATION: His-JO-41 MTD-deltap53 Amino Acid Sequence

<400> SEQUENCE: 72

```
Met Gly Ser Ser His His His His His His Ser Ser Gly Leu Val Pro
  1               5                  10                  15

Arg Gly Ser His Met Ala Ala Ala Leu Leu Ala Val Ala Glu Glu Pro
             20                  25                  30

Gln Ser Asp Pro Ser Val Glu Pro Pro Leu Ser Gln Glu Thr Phe Ser
         35                  40                  45

Asp Leu Trp Lys Leu Leu Pro Glu Asn Asn Val Leu Ser Pro Leu Pro
     50                  55                  60

Ser Gln Ala Met Asp Asp Leu Met Leu Ser Pro Asp Asp Ile Glu Gln
 65                  70                  75                  80

Trp Phe Thr Glu Asp Pro Gly Pro Asp Glu Ala Pro Arg Met Pro Glu
                 85                  90                  95

Ala Ala Pro Arg Val Ala Pro Ala Pro Ala Ala Pro Thr Pro Ala Ala
            100                 105                 110

Pro Ala Pro Ala Pro Ser Trp Pro Leu Ser Ser Ser Val Pro Ser Gln
        115                 120                 125

Lys Thr
    130
```

<210> SEQ ID NO 73
<211> LENGTH: 393
<212> TYPE: DNA
<213> ORGANISM: Artificial Sequence
<220> FEATURE:
<223> OTHER INFORMATION: His-deltap53-JO-41 MTD cDNA Sequence

<400> SEQUENCE: 73

```
atgggcagca gccatcatca tcatcatcac agcagcggcc tggtgccgcg cggcagccat     60

atggaggagc cgcagtcaga tcctagcgtc gagccccctc tgagtcagga aacattttca    120

gacctatgga aactacttcc tgaaaacaac gttctgtccc ccttgccgtc ccaagcaatg    180

gatgatttga tgctgtcccc ggacgatatt gaacaatggt tcactgaaga cccaggtcca    240

gatgaagctc ccagaatgcc agaggctgct ccccgcgtgg cccctgcacc agcagctcct    300

acaccggcgg cccctgcacc agccccctcc tggcccctgt catcttctgt cccttcccag    360

aaaaccgcgg cggcgctgct ggcggtggcg tga                                 393
```

<210> SEQ ID NO 74
<211> LENGTH: 130
<212> TYPE: PRT
<213> ORGANISM: Artificial Sequence
<220> FEATURE:
<223> OTHER INFORMATION: His-deltap53-JO-41 MTD Amino Acid Sequence

<400> SEQUENCE: 74

```
Met Gly Ser Ser His His His His His His Ser Ser Gly Leu Val Pro
  1               5                  10                  15

Arg Gly Ser His Met Glu Glu Pro Gln Ser Asp Pro Ser Val Glu Pro
             20                  25                  30

Pro Leu Ser Gln Glu Thr Phe Ser Asp Leu Trp Lys Leu Leu Pro Glu
         35                  40                  45

Asn Asn Val Leu Ser Pro Leu Pro Ser Gln Ala Met Asp Asp Leu Met
     50                  55                  60

Leu Ser Pro Asp Asp Ile Glu Gln Trp Phe Thr Glu Asp Pro Gly Pro
 65                  70                  75                  80

Asp Glu Ala Pro Arg Met Pro Glu Ala Ala Pro Arg Val Ala Pro Ala
                 85                  90                  95

Pro Ala Ala Pro Thr Pro Ala Ala Pro Ala Pro Ala Pro Ser Trp Pro
            100                 105                 110

Leu Ser Ser Ser Val Pro Ser Gln Lys Thr Ala Ala Ala Leu Leu Ala
        115                 120                 125

Val Ala
    130
```

<210> SEQ ID NO 75
<211> LENGTH: 408
<212> TYPE: DNA
<213> ORGANISM: Artificial Sequence
<220> FEATURE:
<223> OTHER INFORMATION: His-NLS-JO-41 MTD-deltap53 cDNA Sequence

<400> SEQUENCE: 75

```
atgggcagca gccatcatca tcatcatcac agcagcggcc tggtgccgcg cggcagccat      60

atgaagaaga agaggaaggc ggcggcgctg ctggcggtgg cggaggagcc gcagtcagat     120

cctagcgtcg agccccctct gagtcaggaa acattttcag acctatggaa actacttcct     180

gaaaacaacg ttctgtcccc cttgccgtcc caagcaatgg atgatttgat gctgtccccg     240

gacgatattg aacaatggtt cactgaagac ccaggtccag atgaagctcc cagaatgcca     300

gaggctgctc cccgcgtggc ccctgcacca gcagctccta caccggcggc ccctgcacca     360

gcccccctcct ggcccctgtc atcttctgtc ccttcccaga aaacctga                 408
```

<210> SEQ ID NO 76
<211> LENGTH: 135
<212> TYPE: PRT
<213> ORGANISM: Artificial Sequence
<220> FEATURE:
<223> OTHER INFORMATION: His-NLS-JO-41 MTD-deltap53 Amino Acid Sequence

<400> SEQUENCE: 76

```
Met Gly Ser Ser His His His His His His Ser Ser Gly Leu Val Pro
  1               5                  10                  15

Arg Gly Ser His Met Lys Lys Lys Arg Lys Ala Ala Ala Leu Leu Ala
             20                  25                  30

Val Ala Glu Glu Pro Gln Ser Asp Pro Ser Val Glu Pro Pro Leu Ser
         35                  40                  45

Gln Glu Thr Phe Ser Asp Leu Trp Lys Leu Leu Pro Glu Asn Asn Val
```

```
     50                  55                  60

Leu Ser Pro Leu Pro Ser Gln Ala Met Asp Asp Leu Met Leu Ser Pro
 65                  70                  75                  80

Asp Asp Ile Glu Gln Trp Phe Thr Glu Asp Pro Gly Pro Asp Glu Ala
                 85                  90                  95

Pro Arg Met Pro Glu Ala Ala Pro Arg Val Ala Pro Ala Pro Ala Ala
            100                 105                 110

Pro Thr Pro Ala Ala Pro Ala Pro Ala Pro Ser Trp Pro Leu Ser Ser
        115                 120                 125

Ser Val Pro Ser Gln Lys Thr
    130                 135


<210> SEQ ID NO 77
<211> LENGTH: 408
<212> TYPE: DNA
<213> ORGANISM: Artificial Sequence
<220> FEATURE:
<223> OTHER INFORMATION: His-NLS-deltap53-JO-41 MTD cDNA Sequence

<400> SEQUENCE: 77

atgggcagca gccatcatca tcatcatcac agcagcggcc tggtgccgcg cggcagccat      60

atgaagaaga agaggaagga ggagccgcag tcagatccta gcgtcgagcc ccctctgagt     120

caggaaacat tttcagacct atggaaacta cttcctgaaa acaacgttct gtcccccttg     180

ccgtcccaag caatggatga tttgatgctg tccccggacg atattgaaca atggttcact     240

gaagacccag gtccagatga agctcccaga atgccagagg ctgctccccg cgtggcccct     300

gcaccagcag ctcctacacc ggcggcccct gcaccagccc cctcctggcc cctgtcatct     360

tctgtccctt cccagaaaac cgcggcggcg ctgctggcgg tggcgtga                  408


<210> SEQ ID NO 78
<211> LENGTH: 135
<212> TYPE: PRT
<213> ORGANISM: Artificial Sequence
<220> FEATURE:
<223> OTHER INFORMATION: His-NLS-deltap53-JO-41 MTD Amino Acid Sequence

<400> SEQUENCE: 78

Met Gly Ser Ser His His His His His His Ser Ser Gly Leu Val Pro
  1               5                  10                  15

Arg Gly Ser His Met Lys Lys Lys Arg Lys Glu Glu Pro Gln Ser Asp
            20                  25                  30

Pro Ser Val Glu Pro Pro Leu Ser Gln Glu Thr Phe Ser Asp Leu Trp
        35                  40                  45

Lys Leu Leu Pro Glu Asn Asn Val Leu Ser Pro Leu Pro Ser Gln Ala
     50                  55                  60

Met Asp Asp Leu Met Leu Ser Pro Asp Asp Ile Glu Gln Trp Phe Thr
 65                  70                  75                  80

Glu Asp Pro Gly Pro Asp Glu Ala Pro Arg Met Pro Glu Ala Ala Pro
                 85                  90                  95

Arg Val Ala Pro Ala Pro Ala Ala Pro Thr Pro Ala Ala Pro Ala Pro
            100                 105                 110

Ala Pro Ser Trp Pro Leu Ser Ser Ser Val Pro Ser Gln Lys Thr Ala
        115                 120                 125

Ala Ala Leu Leu Ala Val Ala
    130                 135


<210> SEQ ID NO 79
```

<211> LENGTH: 48
<212> TYPE: DNA
<213> ORGANISM: Artificial Sequence
<220> FEATURE:
<223> OTHER INFORMATION: 5'-HNp53

<400> SEQUENCE: 79
ccgcatatga agaagaagag gaaggaggag ccgcagtcag atcctagc 48

<210> SEQ ID NO 80
<211> LENGTH: 78
<212> TYPE: DNA
<213> ORGANISM: Artificial Sequence
<220> FEATURE:
<223> OTHER INFORMATION: 5'-HNM41p53

<400> SEQUENCE: 80
ccgcatatga agaagaagag gaagccgctg gtgctggcga ttgcggcggt gctggaggag 60
ccgcagtcag atcctagc 78

<210> SEQ ID NO 81
<211> LENGTH: 72
<212> TYPE: DNA
<213> ORGANISM: Artificial Sequence
<220> FEATURE:
<223> OTHER INFORMATION: 5'-HNM41p53

<400> SEQUENCE: 81
ccgcatatga agaagaagag gaaggcggcg gcgctgctgg cggtggcgga ggagccgcag 60
tcagatccta gc 72

<210> SEQ ID NO 82
<211> LENGTH: 36
<212> TYPE: DNA
<213> ORGANISM: Artificial Sequence
<220> FEATURE:
<223> OTHER INFORMATION: 3'-HNp53

<400> SEQUENCE: 82
ccgcatatgt cagtctgagt caggcccttc tgtctt 36

<210> SEQ ID NO 83
<211> LENGTH: 66
<212> TYPE: DNA
<213> ORGANISM: Artificial Sequence
<220> FEATURE:
<223> OTHER INFORMATION: 3'-HNp53M39

<400> SEQUENCE: 83
ccgcatatgt cacagcaccg ccgcaatcgc cagcaccagc gggtctgagt caggcccttc 60
tgtctt 66

<210> SEQ ID NO 84
<211> LENGTH: 60
<212> TYPE: DNA
<213> ORGANISM: Artificial Sequence
<220> FEATURE:
<223> OTHER INFORMATION: 3'-HNp53M41

<400> SEQUENCE: 84
ccgcatatgt cacgccaccg ccagcagcgc cgccgcgtct gagtcaggcc cttctgtctt 60

<210> SEQ ID NO 85
<211> LENGTH: 33
<212> TYPE: DNA

<213> ORGANISM: Artificial Sequence
<220> FEATURE:
<223> OTHER INFORMATION: 5'-Hdeltap53

<400> SEQUENCE: 85
ccgcatatgg aggagccgca gtcagatcct agc 33

<210> SEQ ID NO 86
<211> LENGTH: 63
<212> TYPE: DNA
<213> ORGANISM: Artificial Sequence
<220> FEATURE:
<223> OTHER INFORMATION: 5'-HM39deltap53

<400> SEQUENCE: 86
ccgcatatgc cgctggtgct ggcgattgcg gcggtgctgg aggagccgca gtcagatcct 60
agc 63

<210> SEQ ID NO 87
<211> LENGTH: 57
<212> TYPE: DNA
<213> ORGANISM: Artificial Sequence
<220> FEATURE:
<223> OTHER INFORMATION: 5'-HM41deltap53

<400> SEQUENCE: 87
ccgcatatgg cggcggcgct gctggcggtg gcggaggagc cgcagtcaga tcctagc 57

<210> SEQ ID NO 88
<211> LENGTH: 36
<212> TYPE: DNA
<213> ORGANISM: Artificial Sequence
<220> FEATURE:
<223> OTHER INFORMATION: 3'-HNdeltap53

<400> SEQUENCE: 88
ccgcatatgt caggttttct gggaagggac agaaga 36

<210> SEQ ID NO 89
<211> LENGTH: 66
<212> TYPE: DNA
<213> ORGANISM: Artificial Sequence
<220> FEATURE:
<223> OTHER INFORMATION: 3'-HNdeltap53M39

<400> SEQUENCE: 89
ccgcatatgt cacagcaccg ccgcaatcgc cagcaccagc ggggttttct gggaagggac 60
agaaga 66

<210> SEQ ID NO 90
<211> LENGTH: 60
<212> TYPE: DNA
<213> ORGANISM: Artificial Sequence
<220> FEATURE:
<223> OTHER INFORMATION: 3'-HNdeltap53M41

<400> SEQUENCE: 90
ccgcatatgt cacgccaccg ccagcagcgc cgccgcggtt ttctgggaag ggacagaaga 60